US011091517B2

(12) United States Patent
Katagiri et al.

(10) Patent No.: US 11,091,517 B2
(45) Date of Patent: Aug. 17, 2021

(54) PEPTIDE DERIVATIVE AND PHARMACEUTICAL COMPOSITION CONTAINING SAME

(71) Applicants: TOKUSHIMA UNIVERSITY, Tokushima (JP); ONCOTHERAPY SCIENCE, INC., Kawasaki (JP)

(72) Inventors: Toyomasa Katagiri, Tokushima (JP); Tetsuro Yoshimaru, Tokushima (JP); Takashi Miyamoto, Kawasaki (JP); Yasuhide Okamoto, Kawasaki (JP)

(73) Assignees: TOKUSHIMA UNIVERSITY, Tokushima (JP); ONCOTHERAPY SCIENCE, INC., Kawasaki (JP)

( * ) Notice: Subject to any disclaimer, the term of this patent is extended or adjusted under 35 U.S.C. 154(b) by 0 days.

(21) Appl. No.: 16/631,141

(22) PCT Filed: Jul. 18, 2018

(86) PCT No.: PCT/JP2018/026904
§ 371 (c)(1),
(2) Date: Jan. 14, 2020

(87) PCT Pub. No.: WO2019/017384
PCT Pub. Date: Jan. 24, 2019

(65) Prior Publication Data
US 2020/0255474 A1 Aug. 13, 2020

(30) Foreign Application Priority Data
Jul. 19, 2017 (JP) .............................. JP2017-140101

(51) Int. Cl.
C07K 7/08 (2006.01)
A61K 47/65 (2017.01)
A61P 35/00 (2006.01)
A61K 38/00 (2006.01)

(52) U.S. Cl.
CPC ............... C07K 7/08 (2013.01); A61K 47/65 (2017.08); A61P 35/00 (2018.01); A61K 38/00 (2013.01)

(58) Field of Classification Search
CPC ........ A61K 38/00; A61K 38/10; A61K 47/65; A61P 13/08; A61P 15/08; A61P 15/14; A61P 35/00; A61P 43/00; C07K 7/08
See application file for complete search history.

(56) References Cited

U.S. PATENT DOCUMENTS

| | | | |
|---|---|---|---|
| 10,669,310 B2 * | 6/2020 | Katagiri ................. | A61K 38/00 |
| 2009/0175844 A1 | 7/2009 | Nakamura et al. | |
| 2011/0135647 A1 | 6/2011 | Nakamura et al. | |
| 2012/0014996 A1 | 1/2012 | Nakamura et al. | |
| 2013/0011933 A1 | 1/2013 | Nakamura et al. | |
| 2014/0162952 A1 | 6/2014 | Katagiri et al. | |
| 2019/0023739 A1 | 1/2019 | Katagiri et al. | |

FOREIGN PATENT DOCUMENTS

| | | |
|---|---|---|
| JP | 2016-523241 A | 8/2016 |
| WO | WO 2006/085684 A2 | 8/2006 |
| WO | WO 2008/018642 A2 | 2/2008 |
| WO | WO 2013/018690 A1 | 2/2013 |
| WO | WO 2014/201370 A1 | 12/2014 |
| WO | WO 2017/126461 A1 | 7/2017 |

OTHER PUBLICATIONS

Chlebowski, et al; Clinical perspectives on the utility of aromatase inhibitors for the adjuvant treatment of breast cancer; Breast; Aug. 2009:18 Suppl 2:S1-11.
Chumsri, et al; Aromatase, Aromatase Inhibitors, and Breast Cancer; J. Steroid Biochem Mol Biol.; May 2011; 125(1-2):13-22.
Clarke, et al; Cellular and Molecular Pharmacology of Antiestrogen Action and Resistance; Pharmacol Rev.; Mar. 2001; 53(1):25-71.
Fisher, et al; Five Versus More Than Five Years of Tamoxifen for Lymph Node-Negatiave Breast Cancer, etc.; J Natl Cancer Inst.; May 2, 2001; 93(9):684-90.
Fisher, et al; Tamoxifen for the Prevention of Breast Cancer: Current Status, etc; J Natl Cancer Inst.; Nov. 16, 2005; 97(22):1652-62.
Johnston; New Strategies in Estrogen Receptor-Positive Breast Cancer; Clin Cancer Res. Apr. 1, 2010; 16(7):1979-87.
Jordan; Tamoxifen: A Most Unlikely Pioneering Medicine; Nat Rev Drug Discov.; Mar. 2003; 2(3):205-13.
Kim, et al; Activation of an estrogen/estrogen receptor signaling by BIG3 through its inhibitory effect, etc.; Cancer Sci.; Aug. 2009; 100(8):1468-78.
Kim, et al; Identification and characterization of ERAP1 as a novel molecular target for breast cancer ther.;Abst. annual meeting of Japanese Cancer Assoc.; 2008;67;309;0-414.
Kim, et al; BIG3 Inhibits the Estrogen-Dependent Nuclear Translocation of PHB2 via Multiple Karyopherin-Alpha Proteins, etc.; PLoS One; Jun. 8, 2015; 10(6):1-16.
Walensky, et al; Hydrocarbon-Stapled Peptides: Principles, Practice and Progress; J Med chem.; Aug. 14, 2014; 57(15):6275-88.
Yoshimaru, et al; Stapled BIG3 helical peptide Erap potentiates anti-tumour activity for breast cancer therapeutics; Sci Rep.; May 12, 2017; 7(1):1821.
Yoshimaru, et al; Targeting BIG3-PHB2 interaction to overcome tamoxifen resistance in breast cancer cells; Nat Commun.; Sep. 20, 2013; 4:2443; 1-13.

(Continued)

*Primary Examiner* — Marcela M Cordero Garcia
(74) *Attorney, Agent, or Firm* — Kilpatrick Townsend & Stockton LLP

(57) ABSTRACT

The present invention provides peptides having a structure in which portions of a dominant-negative peptide of BIG3 which inhibits the interaction between BIG3 and PHB2 are replaced by at least two stapling structures. The peptides of the present invention have excellent cell growth inhibiting activity. The cell growth inhibiting activity lasts longer, compared to a single-stapled peptide. Therefore, the peptides of the present invention have a feature suitable for clinical applications in cancer therapy.

13 Claims, 34 Drawing Sheets

Specification includes a Sequence Listing.

(56) References Cited

OTHER PUBLICATIONS

Yoshimaru, et al; Therapeutic advances in BIG3-PHB2 inhibition targeting the crosstalk between estrogen and growth factors in breast cancer; Cancer Sci.;May 2015;106(5):550-8.
Yoshimaru, et al; Xanthohumol suppresses oestrogen-signalling in breast cancer through the inhibition of BIG3-PHB2 interactions; Sci Rep.; Dec. 8, 2014; 4:7355; 1-9.
Japan Patent Office; International Search Report of PCT/JP2018/026904 dated Aug. 28, 2018.

* cited by examiner

Double stapled ERAP No. 45 : QMXSDLXXQLRXR (SEQ ID NO: 2)

Double stapled ERAP No. 46 : QMXSDLXLQXRQRX (SEQ ID NO: 3)

FIG. 1

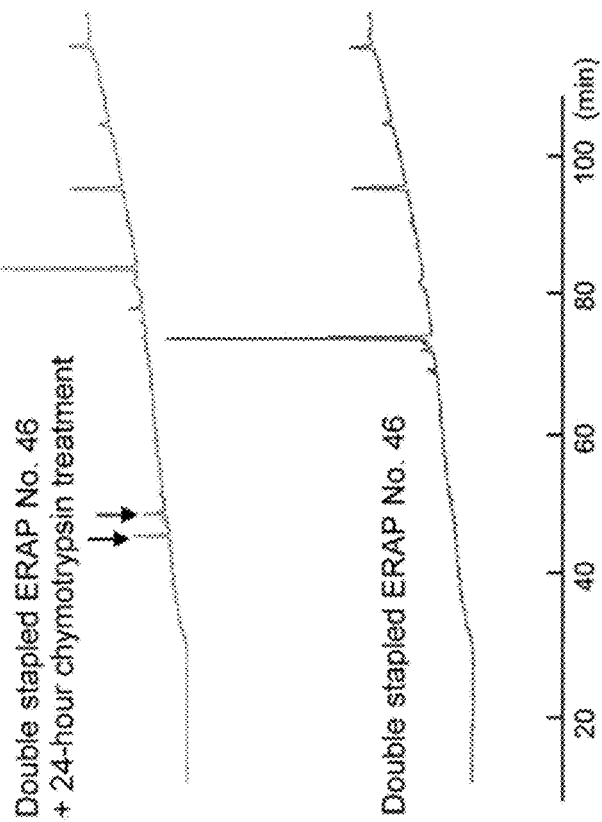
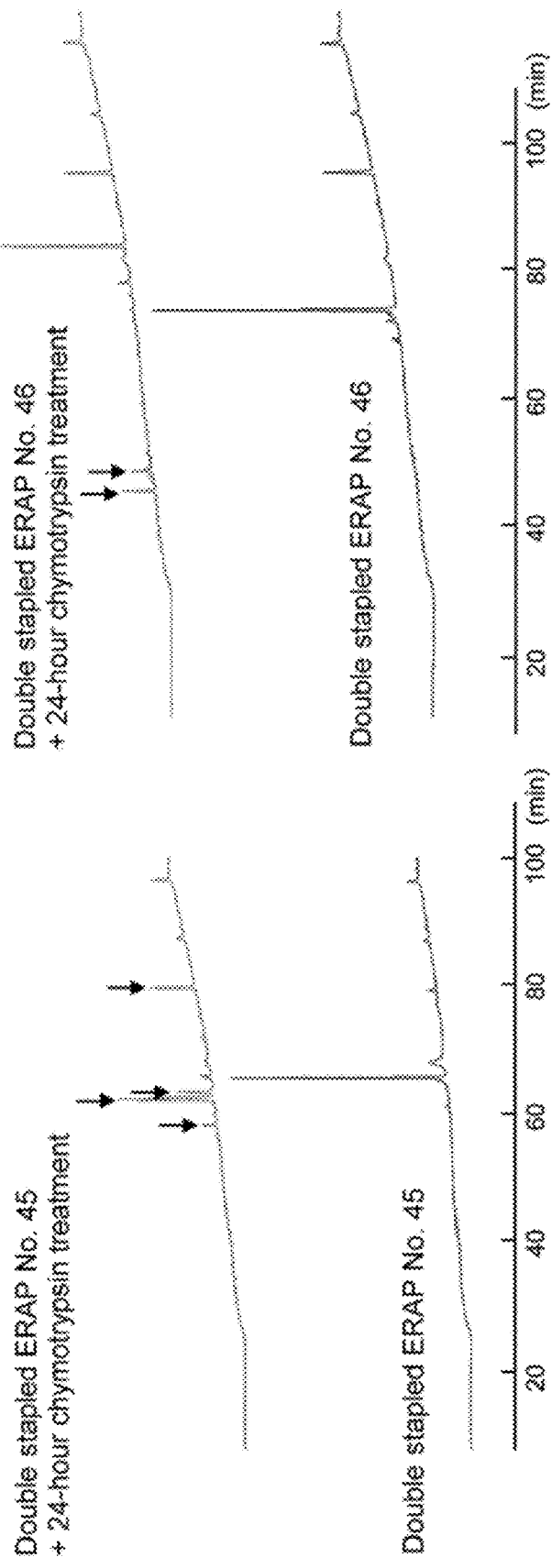

FIG. 10A
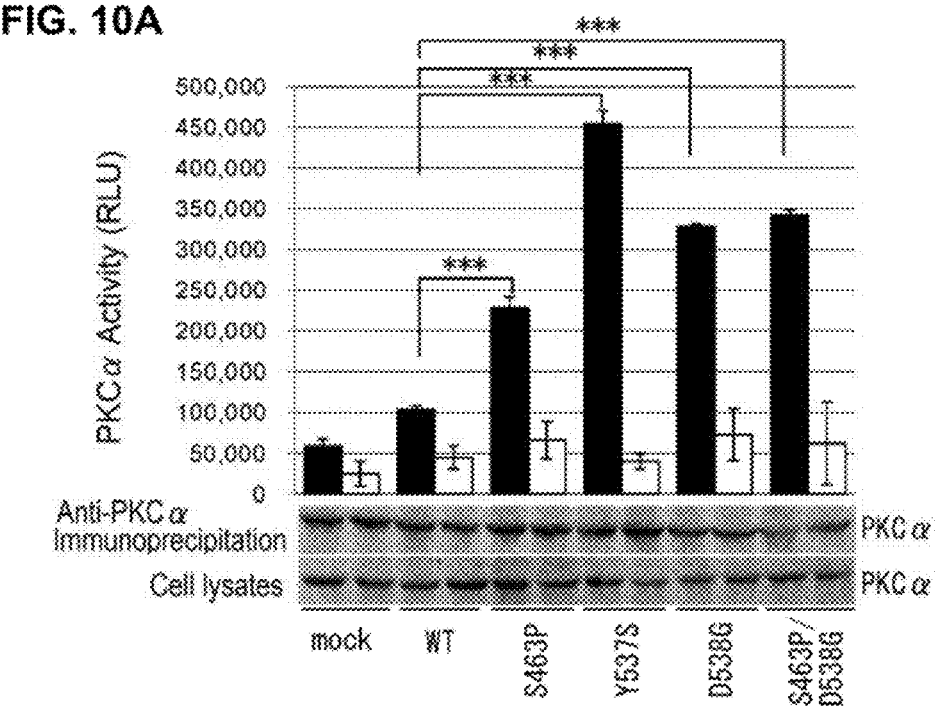
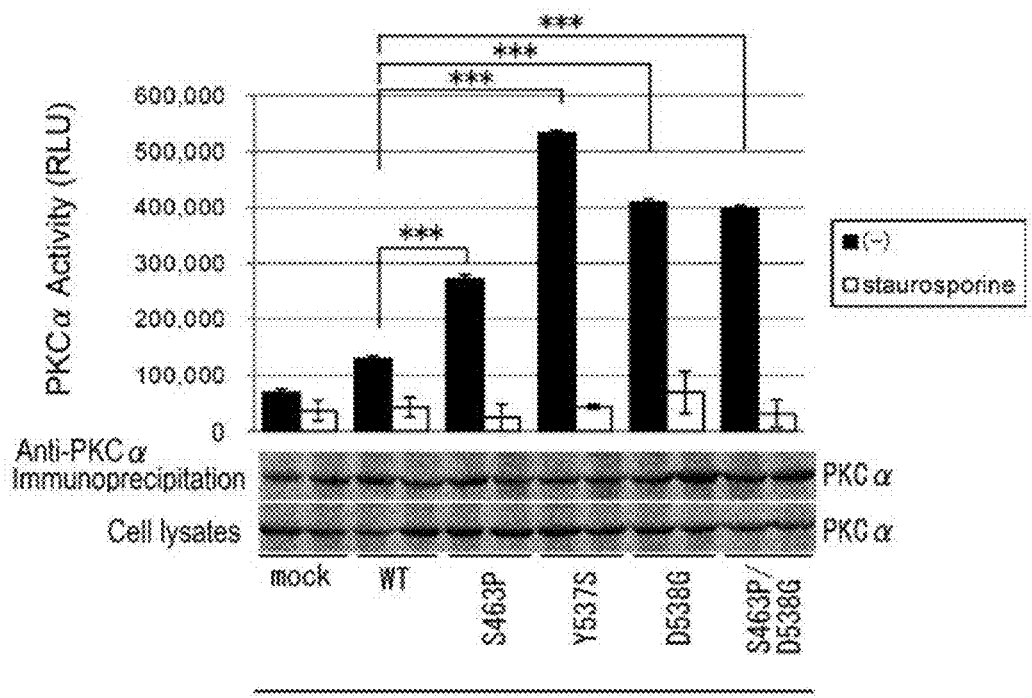

FIG. 15A
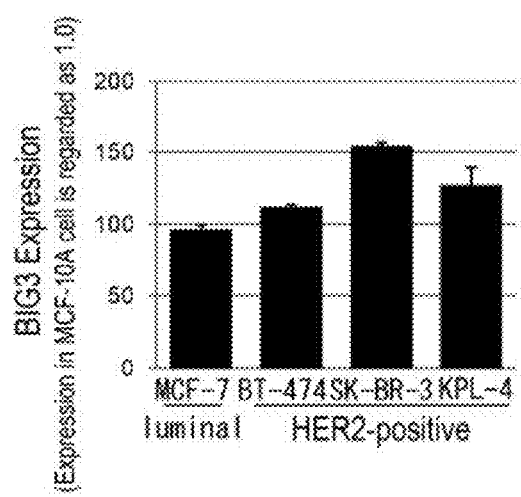
FIG. 15B
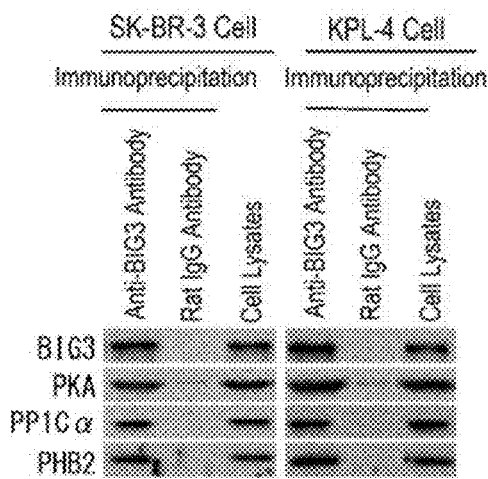
FIG. 15C
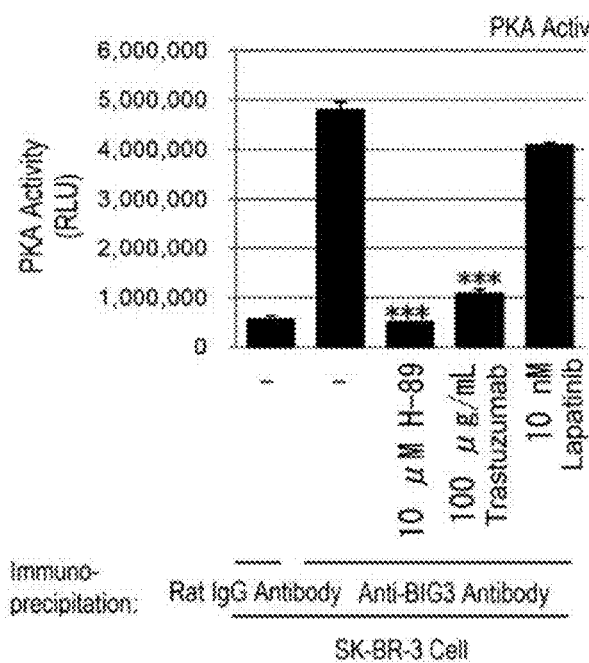
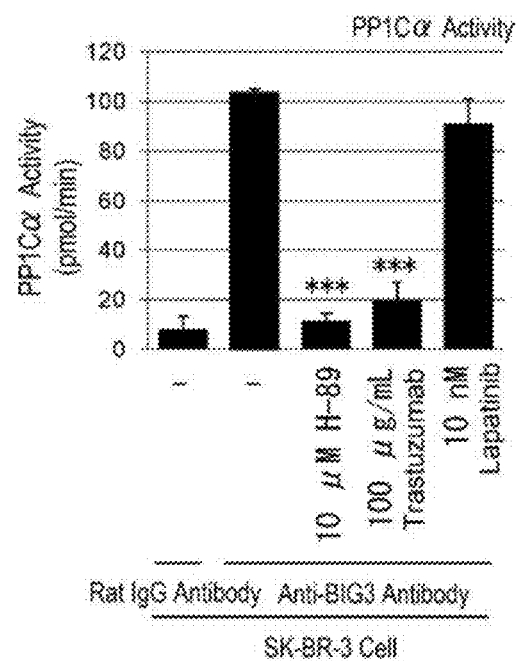

FIG. 21A
FIG. 21B
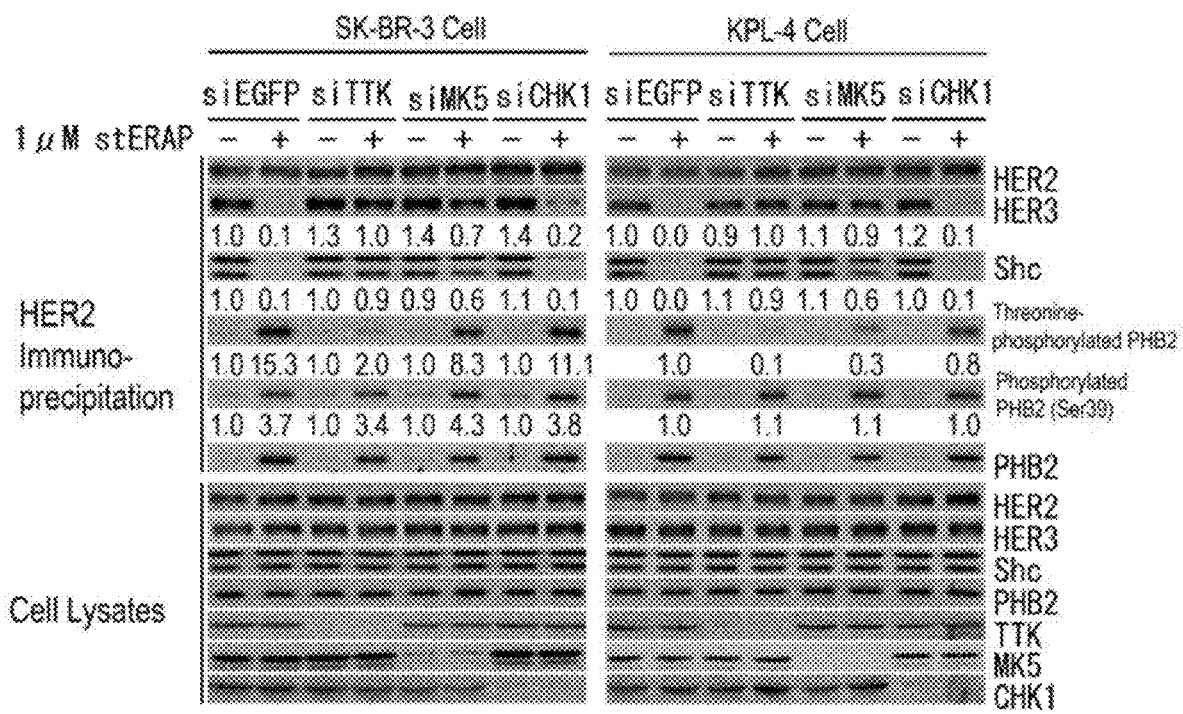
FIG. 21C
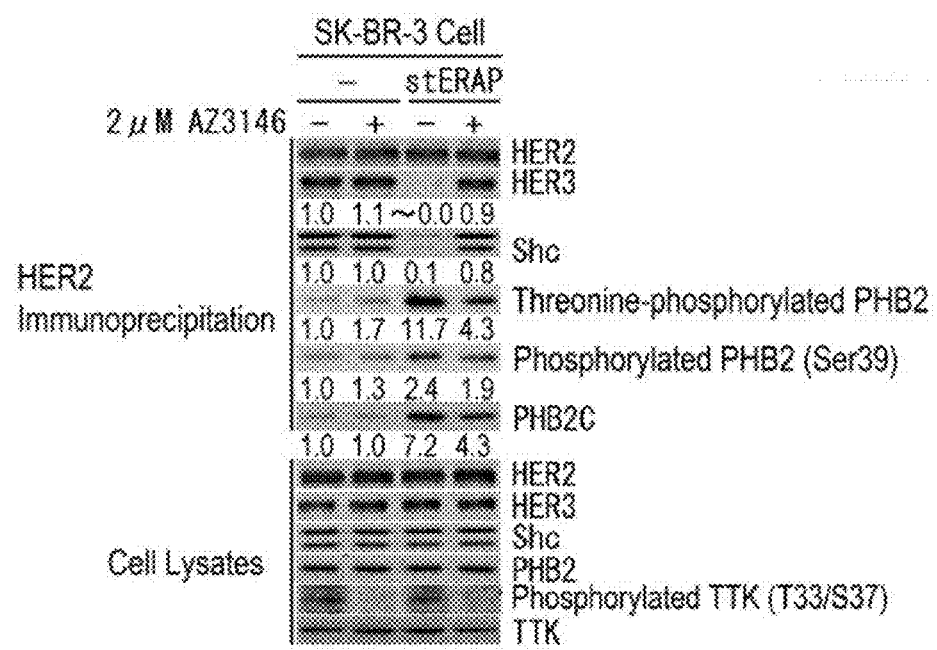

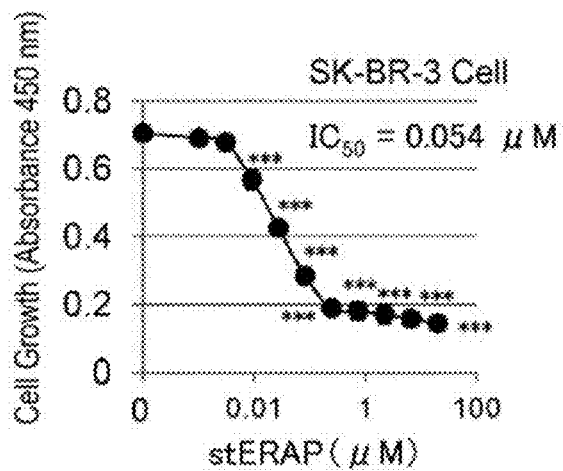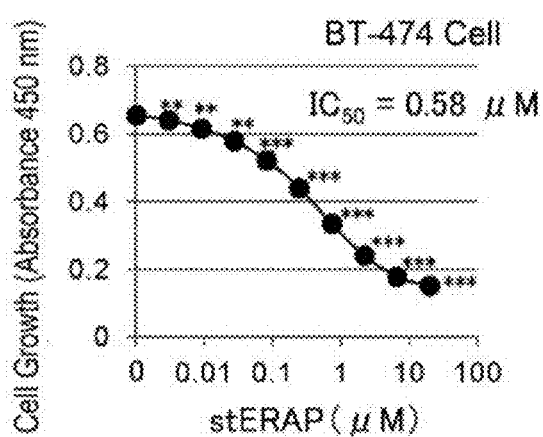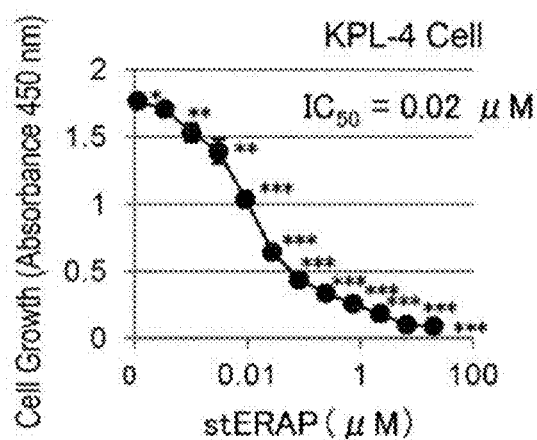
FIG. 24

SEQUENCE LISTING

```
<160> NUMBER OF SEQ ID NOS: 21

<210> SEQ ID NO 1
<211> LENGTH: 13
<212> TYPE: PRT
<213> ORGANISM: Artificial Sequence
<220> FEATURE:
<223> OTHER INFORMATION: Single Stapled PHB2-binding peptide derived
      from BIG3
<220> FEATURE:
<221> NAME/KEY: MISC_FEATURE
<222> LOCATION: (3)..(3)
<223> OTHER INFORMATION: Glutamine analog for stapling
<220> FEATURE:
<221> NAME/KEY: MISC_FEATURE
<222> LOCATION: (7)..(7)
<223> OTHER INFORMATION: Glutamine analog for stapling

<400> SEQUENCE: 1

Gln Met Xaa Ser Asp Leu Xaa Leu Gln Leu Arg Gln Arg
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Double Stapled PHB2-binding peptide derived
      from BIG3
<220> FEATURE:
<221> NAME/KEY: MISC_FEATURE
<222> LOCATION: (3)..(3)
<223> OTHER INFORMATION: Glutamine analog for stapling
<220> FEATURE:
<221> NAME/KEY: MISC_FEATURE
<222> LOCATION: (7)..(8)
<223> OTHER INFORMATION: Glutamine analog for stapling
<220> FEATURE:
<221> NAME/KEY: MISC_FEATURE
<222> LOCATION: (12)..(12)
<223> OTHER INFORMATION: Glutamine analog for stapling
```

<400> SEQUENCE: 2

Gln Met Xaa Ser Asp Leu Xaa Xaa Gln Leu Arg Xaa Arg
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Double Stapled PHB2-binding peptide derived
      from BIG3
<220> FEATURE:
<221> NAME/KEY: MISC_FEATURE
<222> LOCATION: (3)..(3)
<223> OTHER INFORMATION: Glutamine analog for stapling
<220> FEATURE:
<221> NAME/KEY: MISC_FEATURE
<222> LOCATION: (7)..(7)
<223> OTHER INFORMATION: Glutamine analog for stapling
<220> FEATURE:
<221> NAME/KEY: MISC_FEATURE
<222> LOCATION: (10)..(10)
<223> OTHER INFORMATION: Glutamine analog for stapling
<220> FEATURE:
<221> NAME/KEY: MISC_FEATURE
<222> LOCATION: (14)..(14)
<223> OTHER INFORMATION: Glutamine analog for stapling

<400> SEQUENCE: 3

Gln Met Xaa Ser Asp Leu Xaa Leu Gln Xaa Arg Gln Arg Xaa
1               5                   10

<210> SEQ ID NO 4
<211> LENGTH: 13
<212> TYPE: PRT
<213> ORGANISM: Artificial Sequence
<220> FEATURE:
<223> OTHER INFORMATION: PHB2-binding peptide derived from BIG3

<400> SEQUENCE: 4

Gln Met Leu Ser Asp Leu Thr Leu Gln Leu Arg Gln Arg
1               5                   10

<210> SEQ ID NO 5
<211> LENGTH: 14
<212> TYPE: PRT
<213> ORGANISM: Artificial Sequence
<220> FEATURE:
<223> OTHER INFORMATION: PHB2-binding peptide derived from BIG3

<400> SEQUENCE: 5

Gln Met Leu Ser Asp Leu Thr Leu Gln Leu Arg Gln Arg Gln
1               5                   10

<210> SEQ ID NO 6
<211> LENGTH: 14895
<212> TYPE: DNA
<213> ORGANISM: Homo sapiens
<220> FEATURE:
<221> NAME/KEY: CDS
<222> LOCATION: (172)..(6705)

<400> SEQUENCE: 6
gtggcccgcg gcatggagcg ggcgtgattc atcagcatcc gcgccggggc ggcatggggg      60
cgcgcgcggc ggccgcctag gcgcccaggg ccaggcagcg gcggcttccc cggcccggct     120

-continued

| | |
|---|---|
| cgcccgcgct tctctccctg tgggcggcgg cccggcgcct ggaaggtcaa g atg gaa<br>                                                                                                                    Met Glu<br>                                                                                                                     1 | 177 |
| gaa atc ctg agg aag ctg cag aag gag gcg tcc ggg agc aag tac aaa<br>Glu Ile Leu Arg Lys Leu Gln Lys Glu Ala Ser Gly Ser Lys Tyr Lys<br>        5                          10                           15 | 225 |
| gcc atc aag gag agc tgc acc tgg gcc ctg gaa act cta ggt ggt ctg<br>Ala Ile Lys Glu Ser Cys Thr Trp Ala Leu Glu Thr Leu Gly Gly Leu<br>    20                        25                        30 | 273 |
| gat acc att gtc aag atc cct cca cat gta ctg agg gag aaa tgc ctg<br>Asp Thr Ile Val Lys Ile Pro Pro His Val Leu Arg Glu Lys Cys Leu<br>35                      40                        45                        50 | 321 |
| ctg cct ctc cag ttg gct ttg gaa tcc aag aat gtg aag ctg gcc caa<br>Leu Pro Leu Gln Leu Ala Leu Glu Ser Lys Asn Val Lys Leu Ala Gln<br>                      55                        60                        65 | 369 |
| cat gct ttg gca ggg atg cag aag ctt ctg tcg gaa gag agg ttt gta<br>His Ala Leu Ala Gly Met Gln Lys Leu Leu Ser Glu Glu Arg Phe Val<br>            70                        75                        80 | 417 |
| tcc atg gaa aca gat tct gat gag aag cag ctg ctc aat cag ata ctg<br>Ser Met Glu Thr Asp Ser Asp Glu Lys Gln Leu Leu Asn Gln Ile Leu<br>                85                        90                        95 | 465 |
| aat gcc gtg aaa gtg acg cct tcg ctc aac gag gac ctg cag gtg gaa<br>Asn Ala Val Lys Val Thr Pro Ser Leu Asn Glu Asp Leu Gln Val Glu<br>100                      105                      110 | 513 |
| gtg atg aag gtt tta cta tgc atc acc tac acg cca aca ttt gat ctg<br>Val Met Lys Val Leu Leu Cys Ile Thr Tyr Thr Pro Thr Phe Asp Leu<br>115                      120                      125                  130 | 561 |
| aat ggg agt gcc gtg ctg aag atc gcg gag gtg tgc att gag acg tac<br>Asn Gly Ser Ala Val Leu Lys Ile Ala Glu Val Cys Ile Glu Thr Tyr<br>                      135                      140                  145 | 609 |
| ata agc agc tgt cac cag cgt agc ata aac act gct gtg cgg gca act<br>Ile Ser Ser Cys His Gln Arg Ser Ile Asn Thr Ala Val Arg Ala Thr<br>                150                      155                      160 | 657 |
| ctc agt caa atg ctg agt gac ttg act tta cag tta cga cag agg cag<br>Leu Ser Gln Met Leu Ser Asp Leu Thr Leu Gln Leu Arg Gln Arg Gln<br>165                      170                      175 | 705 |
| gag aat acg ata att gaa aac cca gat gtc cca cag gat ttc ggg aat<br>Glu Asn Thr Ile Ile Glu Asn Pro Asp Val Pro Gln Asp Phe Gly Asn<br>    180                      185                      190 | 753 |
| caa ggg tca aca gta gag tcc ctc tgt gat gat gtt gtc tct gta ctc<br>Gln Gly Ser Thr Val Glu Ser Leu Cys Asp Asp Val Val Ser Val Leu<br>195                      200                      205                  210 | 801 |
| acc gtc ctg tgt gag aag ctg caa gcc gcc ata aat gac agc cag cag<br>Thr Val Leu Cys Glu Lys Leu Gln Ala Ala Ile Asn Asp Ser Gln Gln<br>                      215                      220                  225 | 849 |
| ctg cag ctt ctc tac ctg gag tgc atc ctg tct gtg ctc agc agc tcc<br>Leu Gln Leu Leu Tyr Leu Glu Cys Ile Leu Ser Val Leu Ser Ser Ser<br>                230                      235                      240 | 897 |
| tcc tcc tcc atg cac ctg cac agg cgc ttc acg gac ctg atc tgg aaa<br>Ser Ser Ser Met His Leu His Arg Arg Phe Thr Asp Leu Ile Trp Lys<br>245                      250                      255 | 945 |
| aac ctc tgc cct gct ctc atc gtg atc ttg ggg aat cca att cat gac<br>Asn Leu Cys Pro Ala Leu Ile Val Ile Leu Gly Asn Pro Ile His Asp<br>    260                      265                      270 | 993 |
| aaa acc atc acc tct gct cac acc agc agc acc agt acc agc ctg gag<br>Lys Thr Ile Thr Ser Ala His Thr Ser Ser Thr Ser Thr Ser Leu Glu<br>275                      280                      285                  290 | 1041 |
| tcg gac tct gcg tct ccg gga gtg tct gac cac ggc cga gga tca ggc<br>Ser Asp Ser Ala Ser Pro Gly Val Ser Asp His Gly Arg Gly Ser Gly<br>                      295                      300                  305 | 1089 |

-continued

| | | |
|---|---|---|
| tgc tcc tgc act gcg ccg gcc ctg agc gga cct gtg gct cgg act atc<br>Cys Ser Cys Thr Ala Pro Ala Leu Ser Gly Pro Val Ala Arg Thr Ile<br>310                        315                      320 | 1137 |
| tat tac atc gca gcc gag ctg gtc cgg ctg gtg ggg tct gtg gac tcc<br>Tyr Tyr Ile Ala Ala Glu Leu Val Arg Leu Val Gly Ser Val Asp Ser<br>325                        330                      335 | 1185 |
| atg aag ccc gtg ctc cag tcc ctc tac cac cga gtg ctg ctc tac ccc<br>Met Lys Pro Val Leu Gln Ser Leu Tyr His Arg Val Leu Leu Tyr Pro<br>340                        345                      350 | 1233 |
| cca ccc cag cac cgg gtg gaa gcc atc aaa ata atg aaa gag ata ctt<br>Pro Pro Gln His Arg Val Glu Ala Ile Lys Ile Met Lys Glu Ile Leu<br>355                      360                      365                      370 | 1281 |
| ggg agc cca cag cgt ctc tgt gac ttg gca gga ccc agc tcc act gaa<br>Gly Ser Pro Gln Arg Leu Cys Asp Leu Ala Gly Pro Ser Ser Thr Glu<br>                        375                      380                      385 | 1329 |
| tca gag tcc aga aaa aga tca att tca aaa aga aag tct cat ctg gat<br>Ser Glu Ser Arg Lys Arg Ser Ile Ser Lys Arg Lys Ser His Leu Asp<br>390                        395                      400 | 1377 |
| ctc ctc aaa ctc atc atg gat ggc atg acc gaa gca tgc atc aag ggt<br>Leu Leu Lys Leu Ile Met Asp Gly Met Thr Glu Ala Cys Ile Lys Gly<br>                        405                      410                      415 | 1425 |
| ggc atc gaa gct tgc tat gca gcc gtg tcc tgt gtc tgc acc ttg ctg<br>Gly Ile Glu Ala Cys Tyr Ala Ala Val Ser Cys Val Cys Thr Leu Leu<br>420                        425                      430 | 1473 |
| ggt gcc ctg gat gag ctc agc cag ggg aag ggc ttg agc gaa ggt cag<br>Gly Ala Leu Asp Glu Leu Ser Gln Gly Lys Gly Leu Ser Glu Gly Gln<br>435                        440                      445                      450 | 1521 |
| gtg caa ctg ctg ctt ctg cgc ctt gag gag ctg aag gat ggg gct gag<br>Val Gln Leu Leu Leu Leu Arg Leu Glu Glu Leu Lys Asp Gly Ala Glu<br>                        455                      460                      465 | 1569 |
| tgg agc cga gat tcc atg gag atc aat gag gct gac ttc cgc tgg cag<br>Trp Ser Arg Asp Ser Met Glu Ile Asn Glu Ala Asp Phe Arg Trp Gln<br>470                        475                      480 | 1617 |
| cgg cga gtg ctg tcc tca gaa cac acg ccg tgg gag tca ggg aac gag<br>Arg Arg Val Leu Ser Ser Glu His Thr Pro Trp Glu Ser Gly Asn Glu<br>                        485                      490                      495 | 1665 |
| agg agc ctt gac atc agc atc agt gtc acc aca gac aca ggc cag acc<br>Arg Ser Leu Asp Ile Ser Ile Ser Val Thr Thr Asp Thr Gly Gln Thr<br>500                        505                      510 | 1713 |
| act ctc gag gga gag ttg ggt cag act aca ccc gag gac cat tcg gga<br>Thr Leu Glu Gly Glu Leu Gly Gln Thr Thr Pro Glu Asp His Ser Gly<br>515                        520                      525                      530 | 1761 |
| aac cac aag aac agt ctc aag tcg cca gcc atc cca gag ggt aag gag<br>Asn His Lys Asn Ser Leu Lys Ser Pro Ala Ile Pro Glu Gly Lys Glu<br>                        535                      540                      545 | 1809 |
| acg ctg agc aaa gta ttg gaa aca gag gcg gta gac cag cca gat gtc<br>Thr Leu Ser Lys Val Leu Glu Thr Glu Ala Val Asp Gln Pro Asp Val<br>550                        555                      560 | 1857 |
| gtg cag aga agc cac acg gtc cct tac cct gac ata act aac ttc ctg<br>Val Gln Arg Ser His Thr Val Pro Tyr Pro Asp Ile Thr Asn Phe Leu<br>                        565                      570                      575 | 1905 |
| tca gta gac tgc agg aca agg tcc tat gga tct agg tat agt gag agc<br>Ser Val Asp Cys Arg Thr Arg Ser Tyr Gly Ser Arg Tyr Ser Glu Ser<br>580                        585                      590 | 1953 |
| aat ttt agc gtt gat gac caa gac ctt tct agg aca gag ttt gat tcc<br>Asn Phe Ser Val Asp Asp Gln Asp Leu Ser Arg Thr Glu Phe Asp Ser<br>595                        600                      605                      610 | 2001 |
| tgt gat cag tac tct atg gca gca gaa aag gac tcg ggc agg tcc gac<br>Cys Asp Gln Tyr Ser Met Ala Ala Glu Lys Asp Ser Gly Arg Ser Asp<br>                        615                      620                      625 | 2049 |

-continued

| | |
|---|---|
| gtg tca gac att ggg tcg gac aac tgt tca cta gcc gat gaa gag cag<br>Val Ser Asp Ile Gly Ser Asp Asn Cys Ser Leu Ala Asp Glu Glu Gln<br>630 635 640 | 2097 |
| aca ccc cgg gac tgc cta ggc cac cgg tcc ctg cga act gcc gcc ctg<br>Thr Pro Arg Asp Cys Leu Gly His Arg Ser Leu Arg Thr Ala Ala Leu<br>645 650 655 | 2145 |
| tct cta aaa ctg ctg aag aac cag gag gcg gat cag cac agc gcc agg<br>Ser Leu Lys Leu Leu Lys Asn Gln Glu Ala Asp Gln His Ser Ala Arg<br>660 665 670 | 2193 |
| ctg ttc ata cag tcc ctg gaa ggc ctc ctc cct cgg ctc ctg tct ctc<br>Leu Phe Ile Gln Ser Leu Glu Gly Leu Leu Pro Arg Leu Leu Ser Leu<br>675 680 685 690 | 2241 |
| tcc aat gta gag gag gtg gac acc gct ctg cag aac ttt gcc tct act<br>Ser Asn Val Glu Glu Val Asp Thr Ala Leu Gln Asn Phe Ala Ser Thr<br>695 700 705 | 2289 |
| ttc tgc tca ggc atg atg cac tct cct ggc ttt gac ggg aat agc agc<br>Phe Cys Ser Gly Met Met His Ser Pro Gly Phe Asp Gly Asn Ser Ser<br>710 715 720 | 2337 |
| ctc agc ttc cag atg ctg atg aac gca gac agc ctc tac aca gct gca<br>Leu Ser Phe Gln Met Leu Met Asn Ala Asp Ser Leu Tyr Thr Ala Ala<br>725 730 735 | 2385 |
| cac tgc gcc ctg ctc ctc aac ctg aag ctc tcc cac ggt gac tac tac<br>His Cys Ala Leu Leu Leu Asn Leu Lys Leu Ser His Gly Asp Tyr Tyr<br>740 745 750 | 2433 |
| agg aag cgg ccg acc ctg gcg cca ggc gtg atg aag gac ttc atg aag<br>Arg Lys Arg Pro Thr Leu Ala Pro Gly Val Met Lys Asp Phe Met Lys<br>755 760 765 770 | 2481 |
| cag gtg cag acc agc ggc gtg ctg atg gtc ttc tct cag gcc tgg att<br>Gln Val Gln Thr Ser Gly Val Leu Met Val Phe Ser Gln Ala Trp Ile<br>775 780 785 | 2529 |
| gag gag ctc tac cat cag gtg ctc gac agg aac atg ctt gga gag gct<br>Glu Glu Leu Tyr His Gln Val Leu Asp Arg Asn Met Leu Gly Glu Ala<br>790 795 800 | 2577 |
| ggc tat tgg ggc agc cca gaa gat aac agc ctt ccc ctc atc aca atg<br>Gly Tyr Trp Gly Ser Pro Glu Asp Asn Ser Leu Pro Leu Ile Thr Met<br>805 810 815 | 2625 |
| ctg acc gat att gac ggc tta gag agc agt gcc att ggt ggc cag ctg<br>Leu Thr Asp Ile Asp Gly Leu Glu Ser Ser Ala Ile Gly Gly Gln Leu<br>820 825 830 | 2673 |
| atg gcc tcg gct gct aca gag tct cct ttc gcc cag agc agg aga att<br>Met Ala Ser Ala Ala Thr Glu Ser Pro Phe Ala Gln Ser Arg Arg Ile<br>835 840 845 850 | 2721 |
| gat gac tcc aca gtg gca ggc gtg gca ttt gct cgc tat att ctg gtg<br>Asp Asp Ser Thr Val Ala Gly Val Ala Phe Ala Arg Tyr Ile Leu Val<br>855 860 865 | 2769 |
| ggc tgc tgg aag aac ttg atc gat act tta tca acc cca ctg act ggt<br>Gly Cys Trp Lys Asn Leu Ile Asp Thr Leu Ser Thr Pro Leu Thr Gly<br>870 875 880 | 2817 |
| cga atg gcg ggg agc tcc aaa ggg ctg gcc ttc att ctg gga gct gaa<br>Arg Met Ala Gly Ser Ser Lys Gly Leu Ala Phe Ile Leu Gly Ala Glu<br>885 890 895 | 2865 |
| ggc atc aaa gag cag aac cag aag gag cgg gac gcc atc tgc atg agc<br>Gly Ile Lys Glu Gln Asn Gln Lys Glu Arg Asp Ala Ile Cys Met Ser<br>900 905 910 | 2913 |
| ctc gac ggg ctg cgg aaa gcc gca cgg ctg agc tgc gct cta ggc gtt<br>Leu Asp Gly Leu Arg Lys Ala Ala Arg Leu Ser Cys Ala Leu Gly Val<br>915 920 925 930 | 2961 |
| gct gct aac tgc gcc tca gcc ctt gcc cag atg gca gct gcc tcc tgt<br>Ala Ala Asn Cys Ala Ser Ala Leu Ala Gln Met Ala Ala Ala Ser Cys<br>935 940 945 | 3009 |

-continued

| | |
|---|---|
| gtc caa gaa gaa aaa gaa gag agg gag gcc caa gaa ccc agt gat gcc<br>Val Gln Glu Glu Lys Glu Glu Arg Glu Ala Gln Glu Pro Ser Asp Ala<br>                  950                       955                  960 | 3057 |
| atc aca caa gtg aaa cta aaa gtg gag cag aaa ctg gag cag att ggg<br>Ile Thr Gln Val Lys Leu Lys Val Glu Gln Lys Leu Glu Gln Ile Gly<br>                    965                       970                  975 | 3105 |
| aag gtg cag ggg gtg tgg ctg cac act gcc cac gtc ttg tgc atg gag<br>Lys Val Gln Gly Val Trp Leu His Thr Ala His Val Leu Cys Met Glu<br>980                       985                       990 | 3153 |
| gcc atc ctc agc gta ggc ctg gag atg gga agc cac aac ccg gac<br>Ala Ile Leu Ser Val Gly Leu Glu Met Gly Ser His Asn Pro Asp<br>995                    1000                   1005 | 3198 |
| tgc tgg cca cac gtg ttc agg gtg tgt gaa tac gtg ggc acc ctg<br>Cys Trp Pro His Val Phe Arg Val Cys Glu Tyr Val Gly Thr Leu<br>1010                  1015                1020 | 3243 |
| gag cac aac cac ttc agc gat ggt gcc tcg cag ccc cct ctg acc<br>Glu His Asn His Phe Ser Asp Gly Ala Ser Gln Pro Pro Leu Thr<br>1025                  1030                1035 | 3288 |
| atc agc cag ccc cag aag gcc act gga agc gct ggc ctc ctt ggg<br>Ile Ser Gln Pro Gln Lys Ala Thr Gly Ser Ala Gly Leu Leu Gly<br>1040                  1045                1050 | 3333 |
| gac ccc gag tgt gag ggc tcg ccc ccc gag cac agc ccg gag cag<br>Asp Pro Glu Cys Glu Gly Ser Pro Pro Glu His Ser Pro Glu Gln<br>1055                  1060                1065 | 3378 |
| ggg cgc tcc ctg agc acg gcc cct gtc gtc cag ccc ctg tcc atc<br>Gly Arg Ser Leu Ser Thr Ala Pro Val Val Gln Pro Leu Ser Ile<br>1070                  1075                1080 | 3423 |
| cag gac ctc gtc cgg gaa ggc agc cgg ggt cgg gcc tcc gac ttc<br>Gln Asp Leu Val Arg Glu Gly Ser Arg Gly Arg Ala Ser Asp Phe<br>1085                  1090                1095 | 3468 |
| cgc ggc ggg agc ctc atg agc ggg agc agc gcg gcc aag gtg gtg<br>Arg Gly Gly Ser Leu Met Ser Gly Ser Ser Ala Ala Lys Val Val<br>1100                  1105                1110 | 3513 |
| ctc acc ctc tcc acg caa gcc gac agg ctc ttt gaa gat gct acg<br>Leu Thr Leu Ser Thr Gln Ala Asp Arg Leu Phe Glu Asp Ala Thr<br>1115                  1120                1125 | 3558 |
| gat aag ttg aac ctc atg gcc ttg gga ggt ttt ctt tac cag ctg<br>Asp Lys Leu Asn Leu Met Ala Leu Gly Gly Phe Leu Tyr Gln Leu<br>1130                  1135                1140 | 3603 |
| aag aaa gca tcg cag tct cag ctt ttc cat tct gtt aca gat aca<br>Lys Lys Ala Ser Gln Ser Gln Leu Phe His Ser Val Thr Asp Thr<br>1145                  1150                1155 | 3648 |
| gtt gat tac tct ctg gca atg cca gga gaa gtt aaa tcc act caa<br>Val Asp Tyr Ser Leu Ala Met Pro Gly Glu Val Lys Ser Thr Gln<br>1160                  1165                1170 | 3693 |
| gac cga aaa agc gcc ctc cac ctg ttc cgc ctg ggg aat gcc atg<br>Asp Arg Lys Ser Ala Leu His Leu Phe Arg Leu Gly Asn Ala Met<br>1175                  1180                1185 | 3738 |
| ctg agg att gtg cgg agc aaa gca cgg ccc ctg ctc cac gtg atg<br>Leu Arg Ile Val Arg Ser Lys Ala Arg Pro Leu Leu His Val Met<br>1190                  1195                1200 | 3783 |
| cgc tgc tgg agc ctt gtg gcc cca cac ctg gtg gag gct gct tgc<br>Arg Cys Trp Ser Leu Val Ala Pro His Leu Val Glu Ala Ala Cys<br>1205                  1210                1215 | 3828 |
| cat aag gaa aga cat gtg tct cag aag gct gtt tcc ttc atc cat<br>His Lys Glu Arg His Val Ser Gln Lys Ala Val Ser Phe Ile His<br>1220                  1225                1230 | 3873 |
| gac ata ctg aca gaa gtc ctc act gac tgg aat gag cca cct cat<br>Asp Ile Leu Thr Glu Val Leu Thr Asp Trp Asn Glu Pro Pro His<br>1235                  1240                1245 | 3918 |

|   |   |   |   |   |   |   |   |   |   |
|---|---|---|---|---|---|---|---|---|---|
| ttt | cac | ttc | aat | gaa | gca | ctc | ttc | cga | cct | ttc | gag | cgt | att | atg | 3963 |
| Phe | His | Phe | Asn | Glu | Ala | Leu | Phe | Arg | Pro | Phe | Glu | Arg | Ile | Met |   |
| 1250 |   |   |   |   | 1255 |   |   |   |   | 1260 |   |   |   |   |   |

| cag | ctg | gaa | ttg | tgt | gat | gag | gac | gtc | caa | gac | cag | gtt | gtc | aca | 4008 |
| Gln | Leu | Glu | Leu | Cys | Asp | Glu | Asp | Val | Gln | Asp | Gln | Val | Val | Thr |   |
| 1265 |   |   |   |   | 1270 |   |   |   |   | 1275 |   |   |   |   |   |

| tcc | att | ggt | gag | ctg | gtt | gaa | gtg | tgt | tcc | acg | cag | atc | cag | tcg | 4053 |
| Ser | Ile | Gly | Glu | Leu | Val | Glu | Val | Cys | Ser | Thr | Gln | Ile | Gln | Ser |   |
| 1280 |   |   |   |   | 1285 |   |   |   |   | 1290 |   |   |   |   |   |

| gga | tgg | aga | ccc | ttg | ttc | agt | gcc | ctg | gaa | aca | gtg | cat | ggc | ggg | 4098 |
| Gly | Trp | Arg | Pro | Leu | Phe | Ser | Ala | Leu | Glu | Thr | Val | His | Gly | Gly |   |
| 1295 |   |   |   |   | 1300 |   |   |   |   | 1305 |   |   |   |   |   |

| aac | aag | tca | gag | atg | aag | gag | tac | ctg | gtt | ggt | gac | tac | tcc | atg | 4143 |
| Asn | Lys | Ser | Glu | Met | Lys | Glu | Tyr | Leu | Val | Gly | Asp | Tyr | Ser | Met |   |
| 1310 |   |   |   |   | 1315 |   |   |   |   | 1320 |   |   |   |   |   |

| gga | aaa | ggc | caa | gct | cca | gtg | ttt | gat | gta | ttt | gaa | gct | ttt | ctc | 4188 |
| Gly | Lys | Gly | Gln | Ala | Pro | Val | Phe | Asp | Val | Phe | Glu | Ala | Phe | Leu |   |
| 1325 |   |   |   |   | 1330 |   |   |   |   | 1335 |   |   |   |   |   |

| aat | act | gac | aac | atc | cag | gtc | ttt | gct | aat | gca | gcc | act | agc | tac | 4233 |
| Asn | Thr | Asp | Asn | Ile | Gln | Val | Phe | Ala | Asn | Ala | Ala | Thr | Ser | Tyr |   |
| 1340 |   |   |   |   | 1345 |   |   |   |   | 1350 |   |   |   |   |   |

| atc | atg | tgc | ctt | atg | aag | ttt | gtc | aaa | gga | ctg | ggg | gag | gtg | gac | 4278 |
| Ile | Met | Cys | Leu | Met | Lys | Phe | Val | Lys | Gly | Leu | Gly | Glu | Val | Asp |   |
| 1355 |   |   |   |   | 1360 |   |   |   |   | 1365 |   |   |   |   |   |

| tgt | aaa | gag | att | gga | gac | tgt | gcc | cca | gca | ccc | gga | gcc | ccg | tcc | 4323 |
| Cys | Lys | Glu | Ile | Gly | Asp | Cys | Ala | Pro | Ala | Pro | Gly | Ala | Pro | Ser |   |
| 1370 |   |   |   |   | 1375 |   |   |   |   | 1380 |   |   |   |   |   |

| aca | gac | ctg | tgc | ctc | ccg | gcc | ctg | gat | tac | ctc | agg | cgc | tgc | tct | 4368 |
| Thr | Asp | Leu | Cys | Leu | Pro | Ala | Leu | Asp | Tyr | Leu | Arg | Arg | Cys | Ser |   |
| 1385 |   |   |   |   | 1390 |   |   |   |   | 1395 |   |   |   |   |   |

| cag | tta | ttg | gcc | aaa | atc | tac | aaa | atg | ccc | ttg | aag | cca | ata | ttc | 4413 |
| Gln | Leu | Leu | Ala | Lys | Ile | Tyr | Lys | Met | Pro | Leu | Lys | Pro | Ile | Phe |   |
| 1400 |   |   |   |   | 1405 |   |   |   |   | 1410 |   |   |   |   |   |

| ctt | agt | ggg | aga | ctt | gcc | ggc | ttg | cct | cga | aga | ctt | cag | gaa | cag | 4458 |
| Leu | Ser | Gly | Arg | Leu | Ala | Gly | Leu | Pro | Arg | Arg | Leu | Gln | Glu | Gln |   |
| 1415 |   |   |   |   | 1420 |   |   |   |   | 1425 |   |   |   |   |   |

| tca | gcc | agc | agt | gag | gat | gga | att | gaa | tca | gtc | ctg | tct | gat | ttt | 4503 |
| Ser | Ala | Ser | Ser | Glu | Asp | Gly | Ile | Glu | Ser | Val | Leu | Ser | Asp | Phe |   |
| 1430 |   |   |   |   | 1435 |   |   |   |   | 1440 |   |   |   |   |   |

| gat | gat | gac | acc | ggt | ctg | ata | gaa | gtc | tgg | ata | atc | ctg | ctg | gag | 4548 |
| Asp | Asp | Asp | Thr | Gly | Leu | Ile | Glu | Val | Trp | Ile | Ile | Leu | Leu | Glu |   |
| 1445 |   |   |   |   | 1450 |   |   |   |   | 1455 |   |   |   |   |   |

| cag | ctg | aca | gcg | gct | gtg | tcc | aat | tgt | cca | cgg | cag | cac | caa | cca | 4593 |
| Gln | Leu | Thr | Ala | Ala | Val | Ser | Asn | Cys | Pro | Arg | Gln | His | Gln | Pro |   |
| 1460 |   |   |   |   | 1465 |   |   |   |   | 1470 |   |   |   |   |   |

| cca | act | ctg | gat | tta | ctc | ttt | gag | ctg | ttg | aga | gat | gtg | acg | aaa | 4638 |
| Pro | Thr | Leu | Asp | Leu | Leu | Phe | Glu | Leu | Leu | Arg | Asp | Val | Thr | Lys |   |
| 1475 |   |   |   |   | 1480 |   |   |   |   | 1485 |   |   |   |   |   |

| aca | cca | gga | cca | ggg | ttt | ggt | atc | tat | gca | gtg | gtt | cac | ctc | ctc | 4683 |
| Thr | Pro | Gly | Pro | Gly | Phe | Gly | Ile | Tyr | Ala | Val | Val | His | Leu | Leu |   |
| 1490 |   |   |   |   | 1495 |   |   |   |   | 1500 |   |   |   |   |   |

| ctt | cct | gtg | atg | tcc | gtt | tgg | ctc | cgc | cgg | agc | cat | aaa | gac | cat | 4728 |
| Leu | Pro | Val | Met | Ser | Val | Trp | Leu | Arg | Arg | Ser | His | Lys | Asp | His |   |
| 1505 |   |   |   |   | 1510 |   |   |   |   | 1515 |   |   |   |   |   |

| tcc | tac | tgg | gat | atg | gcc | tct | gcc | aat | ttc | aag | cac | gct | att | ggt | 4773 |
| Ser | Tyr | Trp | Asp | Met | Ala | Ser | Ala | Asn | Phe | Lys | His | Ala | Ile | Gly |   |
| 1520 |   |   |   |   | 1525 |   |   |   |   | 1530 |   |   |   |   |   |

| ctg | tcc | tgt | gag | ctg | gtg | gtg | gag | cac | att | caa | agc | ttt | cta | cat | 4818 |
| Leu | Ser | Cys | Glu | Leu | Val | Val | Glu | His | Ile | Gln | Ser | Phe | Leu | His |   |
| 1535 |   |   |   |   | 1540 |   |   |   |   | 1545 |   |   |   |   |   |

-continued

| | | | | | | | | | | | | | | |
|---|---|---|---|---|---|---|---|---|---|---|---|---|---|---|
| tca | gat | atc | agg | tac | gag | agc | atg | atc | aat | acc | atg | ctg | aag | gac | 4863 |
| Ser | Asp | Ile | Arg | Tyr | Glu | Ser | Met | Ile | Asn | Thr | Met | Leu | Lys | Asp |
| 1550 | | | | 1555 | | | | | 1560 | | | | | |

| ctc | ttt | gag | ttg | ctg | gtc | gcc | tgt | gtg | gcc | aag | ccc | act | gaa | acc | 4908 |
|---|---|---|---|---|---|---|---|---|---|---|---|---|---|---|---|
| Leu | Phe | Glu | Leu | Leu | Val | Ala | Cys | Val | Ala | Lys | Pro | Thr | Glu | Thr |
| 1565 | | | | | 1570 | | | | | 1575 | | | | |

| atc | tcc | aga | gtg | ggc | tgc | tcc | tgt | att | aga | tac | gtc | ctt | gtg | aca | 4953 |
|---|---|---|---|---|---|---|---|---|---|---|---|---|---|---|---|
| Ile | Ser | Arg | Val | Gly | Cys | Ser | Cys | Ile | Arg | Tyr | Val | Leu | Val | Thr |
| 1580 | | | | | 1585 | | | | | 1590 | | | | |

| gcg | ggc | cct | gtg | ttc | act | gag | gag | atg | tgg | agg | ctt | gcc | tgc | tgt | 4998 |
|---|---|---|---|---|---|---|---|---|---|---|---|---|---|---|---|
| Ala | Gly | Pro | Val | Phe | Thr | Glu | Glu | Met | Trp | Arg | Leu | Ala | Cys | Cys |
| 1595 | | | | | 1600 | | | | | 1605 | | | | |

| gcc | ctg | caa | gat | gcg | ttc | tct | gcc | aca | ctc | aag | cca | gtg | aag | gac | 5043 |
|---|---|---|---|---|---|---|---|---|---|---|---|---|---|---|---|
| Ala | Leu | Gln | Asp | Ala | Phe | Ser | Ala | Thr | Leu | Lys | Pro | Val | Lys | Asp |
| 1610 | | | | | 1615 | | | | | 1620 | | | | |

| ctg | ctg | ggc | tgc | ttc | cac | agc | ggc | acg | gag | agc | ttc | agc | ggg | gaa | 5088 |
|---|---|---|---|---|---|---|---|---|---|---|---|---|---|---|---|
| Leu | Leu | Gly | Cys | Phe | His | Ser | Gly | Thr | Glu | Ser | Phe | Ser | Gly | Glu |
| 1625 | | | | | 1630 | | | | | 1635 | | | | |

| ggc | tgc | cag | gtg | cga | gtg | gcg | gcc | ccg | tcc | tcc | tcc | cca | agt | gcc | 5133 |
|---|---|---|---|---|---|---|---|---|---|---|---|---|---|---|---|
| Gly | Cys | Gln | Val | Arg | Val | Ala | Ala | Pro | Ser | Ser | Ser | Pro | Ser | Ala |
| 1640 | | | | | 1645 | | | | | 1650 | | | | |

| gag | gcc | gag | tac | tgg | cgc | atc | cga | gcc | atg | gcc | cag | cag | gtg | ttt | 5178 |
|---|---|---|---|---|---|---|---|---|---|---|---|---|---|---|---|
| Glu | Ala | Glu | Tyr | Trp | Arg | Ile | Arg | Ala | Met | Ala | Gln | Gln | Val | Phe |
| 1655 | | | | | 1660 | | | | | 1665 | | | | |

| atg | ctg | gac | acc | cag | tgc | tca | cca | aag | aca | cca | aac | aac | ttt | gac | 5223 |
|---|---|---|---|---|---|---|---|---|---|---|---|---|---|---|---|
| Met | Leu | Asp | Thr | Gln | Cys | Ser | Pro | Lys | Thr | Pro | Asn | Asn | Phe | Asp |
| 1670 | | | | | 1675 | | | | | 1680 | | | | |

| cac | gct | cag | tcc | tgc | cag | ctc | att | att | gag | ctg | cct | cct | gat | gaa | 5268 |
|---|---|---|---|---|---|---|---|---|---|---|---|---|---|---|---|
| His | Ala | Gln | Ser | Cys | Gln | Leu | Ile | Ile | Glu | Leu | Pro | Pro | Asp | Glu |
| 1685 | | | | | 1690 | | | | | 1695 | | | | |

| aaa | cca | aat | gga | cac | acc | aag | aaa | agc | gtg | tct | ttc | agg | gaa | att | 5313 |
|---|---|---|---|---|---|---|---|---|---|---|---|---|---|---|---|
| Lys | Pro | Asn | Gly | His | Thr | Lys | Lys | Ser | Val | Ser | Phe | Arg | Glu | Ile |
| 1700 | | | | | 1705 | | | | | 1710 | | | | |

| gtg | gtg | agc | ctg | ctg | tct | cat | cag | gtg | tta | ctc | cag | aac | tta | tat | 5358 |
|---|---|---|---|---|---|---|---|---|---|---|---|---|---|---|---|
| Val | Val | Ser | Leu | Leu | Ser | His | Gln | Val | Leu | Leu | Gln | Asn | Leu | Tyr |
| 1715 | | | | | 1720 | | | | | 1725 | | | | |

| gac | atc | ttg | tta | gag | gag | ttt | gtc | aaa | ggc | ccc | tct | cct | gga | gag | 5403 |
|---|---|---|---|---|---|---|---|---|---|---|---|---|---|---|---|
| Asp | Ile | Leu | Leu | Glu | Glu | Phe | Val | Lys | Gly | Pro | Ser | Pro | Gly | Glu |
| 1730 | | | | | 1735 | | | | | 1740 | | | | |

| gaa | aag | acg | ata | caa | gtg | cca | gaa | gcc | aag | ctg | gct | ggc | ttc | ctc | 5448 |
|---|---|---|---|---|---|---|---|---|---|---|---|---|---|---|---|
| Glu | Lys | Thr | Ile | Gln | Val | Pro | Glu | Ala | Lys | Leu | Ala | Gly | Phe | Leu |
| 1745 | | | | | 1750 | | | | | 1755 | | | | |

| aga | tac | atc | tct | atg | cag | aac | ttg | gca | gtc | ata | ttc | gac | ctg | ctg | 5493 |
|---|---|---|---|---|---|---|---|---|---|---|---|---|---|---|---|
| Arg | Tyr | Ile | Ser | Met | Gln | Asn | Leu | Ala | Val | Ile | Phe | Asp | Leu | Leu |
| 1760 | | | | | 1765 | | | | | 1770 | | | | |

| ctg | gac | tct | tat | agg | act | gcc | agg | gag | ttt | gac | acc | agc | ccc | ggg | 5538 |
|---|---|---|---|---|---|---|---|---|---|---|---|---|---|---|---|
| Leu | Asp | Ser | Tyr | Arg | Thr | Ala | Arg | Glu | Phe | Asp | Thr | Ser | Pro | Gly |
| 1775 | | | | | 1780 | | | | | 1785 | | | | |

| ctg | aag | tgc | ctg | ctg | aag | aaa | gtg | tct | ggc | atc | ggg | ggc | gcc | gcc | 5583 |
|---|---|---|---|---|---|---|---|---|---|---|---|---|---|---|---|
| Leu | Lys | Cys | Leu | Leu | Lys | Lys | Val | Ser | Gly | Ile | Gly | Gly | Ala | Ala |
| 1790 | | | | | 1795 | | | | | 1800 | | | | |

| aac | ctc | tac | cgc | cag | tct | gcg | atg | agc | ttt | aac | att | tat | ttc | cac | 5628 |
|---|---|---|---|---|---|---|---|---|---|---|---|---|---|---|---|
| Asn | Leu | Tyr | Arg | Gln | Ser | Ala | Met | Ser | Phe | Asn | Ile | Tyr | Phe | His |
| 1805 | | | | | 1810 | | | | | 1815 | | | | |

| gcc | ctg | gtg | tgt | gct | gtt | ctc | acc | aat | caa | gaa | acc | atc | acg | gcc | 5673 |
|---|---|---|---|---|---|---|---|---|---|---|---|---|---|---|---|
| Ala | Leu | Val | Cys | Ala | Val | Leu | Thr | Asn | Gln | Glu | Thr | Ile | Thr | Ala |
| 1820 | | | | | 1825 | | | | | 1830 | | | | |

| gag | caa | gtg | aag | aag | gtc | ctt | ttt | gag | gac | gac | gag | aga | agc | acg | 5718 |
|---|---|---|---|---|---|---|---|---|---|---|---|---|---|---|---|
| Glu | Gln | Val | Lys | Lys | Val | Leu | Phe | Glu | Asp | Asp | Glu | Arg | Ser | Thr |
| 1835 | | | | | 1840 | | | | | 1845 | | | | |

```
gat tct tcc cag cag tgt tca tct gag gat gaa gac atc ttt gag      5763
Asp Ser Ser Gln Gln Cys Ser Ser Glu Asp Glu Asp Ile Phe Glu
1850                1855                1860 gaa acc gcc cag gtc agc ccc ccg aga ggc aag gag aag aga cag      5808
Glu Thr Ala Gln Val Ser Pro Pro Arg Gly Lys Glu Lys Arg Gln
1865                1870                1875 tgg cgg gca cgg atg ccc ttg ctc agc gtc cag cct gtc agc aac      5853
Trp Arg Ala Arg Met Pro Leu Leu Ser Val Gln Pro Val Ser Asn
1880                1885                1890 gca gat tgg gtg tgg ctg gtc aag agg ctg cac aag ctg tgc atg      5898
Ala Asp Trp Val Trp Leu Val Lys Arg Leu His Lys Leu Cys Met
1895                1900                1905 gaa ctg tgc aac aac tac atc cag atg cac ttg gac ctg gag aac      5943
Glu Leu Cys Asn Asn Tyr Ile Gln Met His Leu Asp Leu Glu Asn
1910                1915                1920 tgt atg gag gag cct ccc atc ttc aag ggc gac ccg ttc ttc atc      5988
Cys Met Glu Glu Pro Pro Ile Phe Lys Gly Asp Pro Phe Phe Ile
1925                1930                1935 ctg ccc tcc ttc cag tcc gag tca tcc acc cca tcc acc ggg ggc      6033
Leu Pro Ser Phe Gln Ser Glu Ser Ser Thr Pro Ser Thr Gly Gly
1940                1945                1950 ttc tct ggg aaa gaa acc cct tcc gag gat gac aga agc cag tcc      6078
Phe Ser Gly Lys Glu Thr Pro Ser Glu Asp Asp Arg Ser Gln Ser
1955                1960                1965 cgg gag cac atg ggc gag tcc ctg agc ctg aag gcc ggt ggt ggg      6123
Arg Glu His Met Gly Glu Ser Leu Ser Leu Lys Ala Gly Gly Gly
1970                1975                1980 gac ctg ctg ctg ccc ccc agc ccc aaa gtg gag aag aag gat ccc      6168
Asp Leu Leu Leu Pro Pro Ser Pro Lys Val Glu Lys Lys Asp Pro
1985                1990                1995 agc cgg aag aag gag tgg tgg gag aat gcg ggg aac aaa atc tac      6213
Ser Arg Lys Lys Glu Trp Trp Glu Asn Ala Gly Asn Lys Ile Tyr
2000                2005                2010 acc atg gca gcc gac aag acc att tca aag ttg atg acc gaa tac      6258
Thr Met Ala Ala Asp Lys Thr Ile Ser Lys Leu Met Thr Glu Tyr
2015                2020                2025 aaa aag agg aaa cag cag cac aac ctg tcc gcg ttc ccc aaa gag      6303
Lys Lys Arg Lys Gln Gln His Asn Leu Ser Ala Phe Pro Lys Glu
2030                2035                2040 gtc aaa gtg gag aag aaa gga gag cca ctg ggt ccc agg ggc cag      6348
Val Lys Val Glu Lys Lys Gly Glu Pro Leu Gly Pro Arg Gly Gln
2045                2050                2055 gac tcc ccg ctg ctt cag cgt ccc cag cac ttg atg gac caa ggg      6393
Asp Ser Pro Leu Leu Gln Arg Pro Gln His Leu Met Asp Gln Gly
2060                2065                2070 caa atg cgg cat tcc ttc agc gca ggc ccc gag ctg ctg cga cag      6438
Gln Met Arg His Ser Phe Ser Ala Gly Pro Glu Leu Leu Arg Gln
2075                2080                2085 gac aag agg ccc cgc tca ggc tcc acc ggg agc tcc ctc agt gtc      6483
Asp Lys Arg Pro Arg Ser Gly Ser Thr Gly Ser Ser Leu Ser Val
2090                2095                2100 tcg gtg aga gac gca gaa gca cag atc cag gca tgg acc aac atg      6528
Ser Val Arg Asp Ala Glu Ala Gln Ile Gln Ala Trp Thr Asn Met
2105                2110                2115 gtg cta aca gtt ctc aat cag att cag att ctc cca gac cag acc      6573
Val Leu Thr Val Leu Asn Gln Ile Gln Ile Leu Pro Asp Gln Thr
2120                2125                2130 ttc acg gcc ctc cag ccc gca gtg ttc ccg tgc atc agt cag ctg      6618
Phe Thr Ala Leu Gln Pro Ala Val Phe Pro Cys Ile Ser Gln Leu
2135                2140                2145
```

|  |  |  |  |  |  |  |  |  |  |  |  |
|---|---|---|---|---|---|---|---|---|---|---|---|
| acc | tgt | cac | gtg | acc | gac | atc | aga | gtt | cgc | cag | gct | gtg | agg | gag |
| Thr | Cys | His | Val | Thr | Asp | Ile | Arg | Val | Arg | Gln | Ala | Val | Arg | Glu |
| 2150 |  |  |  |  | 2155 |  |  |  |  | 2160 |  |  |  |  |

6663

| tgg | ctg | ggc | agg | gtg | ggc | cgt | gtc | tat | gac | atc | att | gtg | tag |
|---|---|---|---|---|---|---|---|---|---|---|---|---|---|
| Trp | Leu | Gly | Arg | Val | Gly | Arg | Val | Tyr | Asp | Ile | Ile | Val |  |
| 2165 |  |  |  |  | 2170 |  |  |  |  | 2175 |  |  |  |

6705

```
ccgactcctg ttctactctc ccaccaaata acagtagtga gggttagagt cctgccaata    6765
cagctgttgc attttcccca ccactagccc cacttaaact actactactg tctcagagaa    6825
cagtgtttcc taatgtaaaa agcctttcca accactgatc agcattgggg ccatactaag    6885
gtttgtatct agatgacaca aacgatattc tgattttgca cattattata aagaatctaa    6945
taatccttga tatgtttcta actcttgaag tatatttccc agtgcttttg cttacagtgt    7005
tgtccccaaa tgggtcattt tcaaggatta ctcatttgaa aacactatat tgatccattt    7065
gatccatcat ttaaaaaata aatacaattc ctaaggcaat atctgctggt aagtcaagct    7125
gataaacact cagacatcta gtaccaggga ttattaattg gaggaagatt tatggttatg    7185
ggtctggctg ggaagaagac aactataaat acatattctt gggtgtcata atcaagaaag    7245
aggtgacttc tgttgtaaaa taatccagaa cacttcaaaa ttattcctaa atcattaaga    7305
ttttcaggta ttcaccaatt tccccatgta aggtactgtg ttgtaccttt atttctgtat    7365
ttctaaaaga agaagttct ttcctagcag ggtttgaagt ctgtggctta tcagcctgtg    7425
acacagagta cccagtgaaa gtggctggta cgtagattgt caagagacat aagaccgacc    7485
agccaccctg gctgttcttg tggtgtttgt ttccatcccc aaggcaaaca aggaaaggaa    7545
aggaaagaag aaaaggtgcc ttagtccttt gttgcacttc catttccatg ccccacaatt    7605
gtctgaacat aaggtatagc atttggtttt taagaaaaca aaacattaag acgcaactca    7665
ttttatatca acacgcttgg aggaaaggga ctcagggaag ggagcaggga gtgtggggtg    7725
gggatggatt atgatgaaat catttttcaat cttaaaatat aatacaacaa tcttgcaaaa    7785
ttatggtgtc agttacacaa gctctagtct caaaatgaaa gtaatggaga aagacactga    7845
aatttagaaa attttgtcga tttaaaatat ttctcctatc taccaagtaa agttacccta    7905
tgtttgatgt ctttgcattc agaccaatat ttcaggtgga tatttctaag tattactaga    7965
aaatacgttt gaaagcttta tcttattatt tacagtattt ttatatttct tacattatcc    8025
taatgattga aaactcctca atcaagctta cttacacaca ttctacagag ttatttaagg    8085
catacattat aatctcccag ccccattcat aatgaataag tcacccttta aatataagac    8145
acaaattcta cagtattgaa ataaggattt aaagggggtat tgtaaacttt tgccctcctt    8205
gagaaatatg gaactacctt agaggttaag aggaaggcag tgttctgact tctttaggtg    8265
atctgaaaaa aacaccctta tcatccagtg taccatctag agatcaccac agaatccatt    8325
tttttcccag ttcacaaaaa cactctgttt gccttcagtt tttactcact agacaataat    8385
tcaagtttag aaacaggtaa tcagctattt gatcttaaaa ggcaatgaat tgttgggata    8445
tcagtgaact atgttgtata cttttgaatt tttacatttt ataaatggaa ttgaaagttg    8505
gataactgct ttttttaaat tttccaacag aagtaacacc acagttgctt tgtttctttt    8565
tatagcttac ctgaggttca gttcttcttt gtgaacctgt gagtactcca cagtttactg    8625
ggggaaaagg cttcagtaaa gcagaggcta gaattacagt atttatacat agcaactttt    8685
cataaagtag aaaaattcaa aggaagctgc tcaatttga gaataccagc tgggcacggt    8745
ggctcacgcc tgtaatccca gcacttactt gggaggcca aggtgggcag ataacctgcg    8805
gtcaggagtt tgagaccagg ctggacaaca tggtgaaacc tcgtctctac taaaaataca    8865
```

```
aaaattagcc aggtgtggta ggatgcacct gtaatcccag ctacttagga ggccgagaca   8925
ggagaatcgc tcgaacccag gaggcggacg ttgcagtgag ccaagattgc accattgcac   8985
tccagactgg gtgacaagag tgaaactcca tctaaaaaaa aaaaaaaaaa aagtgaata    9045
ctgtatccca aagtatgtta gttgtttgtt tggaaatcag cattctcccc gatgctctat   9105
tatgggatcc aaaattcttg aacataagtt taccctgtac tgtgtccaaa cactgttcta   9165
gttctagcct gattatgggt cccaagaata aaaggatgag taggtgtaca gagctcttga   9225
cctacaattt tttaagagtg ttttggtacc ttcccattgt cttctctata actcagtcct   9285
aacatactct gcactcgagt taccagccat ccacactgac atcagatttc aaccagaacc   9345
atcactgagt gacagcagta cttctcagag gtatttgcag cttgatgcaa agtagtctct   9405
aatgagtagg cattcaggtg gttcttccca gcaggtggag aagaaaggga ggagatgaag   9465
aacactgaga ggggagtggc accttcccag gctgcccagc tcagtctctt gccctgttcc   9525
tgtgactcag ctgcccactc ccccaacttt gtttccctcc ctcccagtct ctgaaagtgt   9585
caggtgtttc tctcctcaca gtctcttttg cagcaacagt aagacaaaat tcaaggcagc   9645
cttttaaagt tacgaacagt tattagcatg tatttacaga cctaagcaga atgagagttt   9705
atacattgtt tttagttgcc tgtatttata gccaaaagta tattaccta aagttgagat    9765
cttttctcttc ttttcctaaa ttttggtaaa gtgtgcttca tgaaacaaac atctggaaaa   9825
ctccaagtat aagagaccct ggactgatga tgggcccagcc aagtatatgg agggacagag  9885
ttctctctgt cattaatgag gacatcggtt ttcacaattg aacctcatgc actgtccaca   9945
gcatctcacc tagctcctgt atctcctgat ctgcttttaa aaatagttag ttaggctgcc  10005
ttttttacacc accttctctc tctcccttg tggtaattt ccagccttcc ccatagatat   10065
aaaactagaa caccttatg atttgggg gtc tatgtaatga ctgaccgata agaacccagg  10125
cagatgctaa catacttaac agctcgcatt aaaatacttt aaatcaggcg tgatggctca  10185
ttcctgtaat ctcaagcact tgggaggct aaggtgggtg gatctcttga ggtcaggagt   10245
tcgagaccaa cctggccaac gtggtgaaac cccgtctcta ctaaaaatac aaaattagcc  10305
gggcatggtg gcagctgcct gtaatcccag ctactcggga agctgaggca ggagaattgc  10365
ttgaacctgg gaggtgggga ttgcagtcag ccaagattgt tctgcagcat gggtgacaaa  10425
gtgagacttc gtctcaagta aataaaacta aaatttttaa atcaaacatg acaaaaatgt  10485
taatataatt cagaagtacc ttgaaattga aacatatttg tgcaatgatc attaggcttt   10545
ttgtccttgt tgttttaaaa tgaggcttat acagagtgag ttgagagtca agtagccttc  10605
gctgtgagac ggtaatgcag ttatataata gatacccttg actttgccag attcatcaca  10665
atactgctta tacaggaaag ttttctcaga aaggaaaatc cattagtatc agtcccatca  10725
agccaaacag aatgaagacc tttgatagta atagcaagag gttacaaata gcagggagga  10785
ggcgagtagt gaatgtcact gtgattgcaa acccttacct gtattatcac acgtagtcct  10845
cacaacaacc ttgtgagaca agtgttgtgt tcctcatttt ttcagagggg aacacagacc  10905
cagagaggtt aagaaatttg cccaagataa caagtaaaag gcaaagttgg ttgcaaaaga  10965
ggtgtttctg aattcaaggg ccatactctc tctctgacaa catgctctaa gtccatagag  11025
taagcactct agtatgaaaa aaagtttcaa ggaacgaggc catgaaaatg agactatttg  11085
acatctcaga tctgtctggg atgttatgga ggttttaaaa aataaagttg aaaaagaaaa  11145
atgaatcatg tttatacata aaaaaatcac atgtaacaca tttcaagtgt ttgaaaataa  11205
aaccaaaatc taaactttag tcttcaagca gacattcagt gttactttag aaaactcact  11265
```

```
gaattaggtg gaaatgatgg aataatacta ttcatggcca gctattaaca cagaagaaca    11325
tggcagtgtg tgtctggaac ggcatgcaca atttgtaaac ctttttcaaa tatcatttaa    11385
tcaactcaga ataaagtgcc ctgtagccaa cagtgcctct ttacttgctt ctctgggaaa    11445
tacatggtac taaattagta gcacaaagtt tgggaatatg caaaataatg gataaccatt    11505
tttcaaaatg tacattctct gaagaggaag cagctggttg gacaggattt cttgaagagc    11565
caggtgctaa gggcatcagg tcgacatcca tagtaaccat gtgccataac atctacacat    11625
ttccacttgt tttacagaca aggtaacagg cagaaggaaa atccagagtc ttgcagtaag    11685
cagatgacaa aacttcaata tgcttgggca ccactaggt gacccaggg agatttagtg       11745 tggccttagg aaagcaaaag agcactttt attggaaata tgagcttgtc actgggaaag       11805
atttgtaaaa ttgatcaaga acttgattta taattatgcc tcaaaaaaaa aagttctcat    11865
ttagtagtgg agcaatctag aaaacatacc ttttttgttt gtttggaaga tcctctttcc    11925
ctggctgtat tgtagtgttt gctatttgat gtggaaataa ctaataactt aagattttgg    11985
aacagaacac cctttagatt tccaaaacac aattcttatt tcaggaagac agaccaaaa    12045 atatctcctg agatcattgg tttcttata aattgtggta ccactccatc attgaagaga     12105
aaccactacc acaccactag caccatacag aacctttct ctgtatcttt gtacaatact    12165 acaaagggt accagggagg agagagtggc tgaccactt agtgacaaaa cagcactcca    12225
ctgctggtga atcccatcta attatggtcc ttccacccctt tcaaccacc aacaactgtt   12285 cgtactgtta attcctatcc tgaaggttta accagtggtt gtctagtatc ttctgtctt    12345 agaacagtgg ttctcaaact ttagtacaca tcagcatcac ctggagggcc ttttttttaaa    12405 ataagacaca gattgctggg ctcatggtca gagttcccag ttaagtaaat caggaaattt    12465
gtatttctaa caagtttata ggtgaggcca atactgctgt tttgggaact atgctttgag    12525
aaccactgcc ttgaaaaaat tccaacttc tacctttaag atcagcctga cttatcaaac      12585
gctagagaaa aactgaatct acccttgggc agatgacttg ggattggatt ctatacagca    12645
gtcttgctca atcttcccag tttccagttt tattatacca acaattggtt tttacaagct    12705
agaagacaat gaatgtataa gttctatgga acagtgagat aaatctaagc ttcttgtctt    12765
tgtatttaga acattgatt ctatggatga tcatttgtat catgttgacc ctttgacttg      12825
tactgaaggt gattttaaat ttaagtatgt agtgtttgaa tttcttccat ccatgtcgtt    12885
ttaatgagat gtttccatgt cagctccttt acagccttgg ctcctggctt acagattttt    12945
gaatagttgt ttgcttgcca gttgtttttac atctttcatt ggccaccaaa atattagcca    13005
tttgagatga gatgagacta cttgttgtac cttcatcttt catttaattt tctggcgtaa    13065
attaacattt taatttcata tatatctgta aagagtctac ccaaaggctt cacgaaatt    13125 tgcaaaatga actaattccc ttttaagcag caggtgtgcc tgttttttgac ttttcagtaa    13185 atatgttgtt tgtgcacata tctacatggt ggagaccata ttcattattt catcttccaa    13245
ataatgggaa aaatataaaa gtgaatcagt gtgctttggg aattcagtga atcatgtta      13305 actcatatag agggggcctt agtttatctc ttctttactg aattaattag ttttggaaat    13365
tcttttacca ttaaaaaaaa ttaaggacca tacagagaat gatttaagaa aaaacaagtc    13425
acttaaaaat catcacctat ttataaactg tattaattac acataatgct tattgattca    13485
atgaggtttc tctaaaagact tctgcttaat aaatatgctg acttcattta aattagttta    13545
gactattgta ggaatggaag gaaatgatta tatttactag aattagtgag atcagaaagc    13605
atatcagaat gttgatgata tcaaggagac aatctacaga gttttgcct ctgtggatgg      13665
```

```
aaataagggt gttttttttt ggtttttttt ttactttagt ttcccataat ttttggaaat    13725
tatgtgtgca tttagttctt ttagtaacac tgattttaaa attaaatttc aaaagtcaat    13785
ctctaagagt aatttatttt tgttttacca accagtgcca aaaaggagag gagggaatcc    13845
aaaagccaat cttttgaacc aatgtgtaaa agattatgtt ttttcttaaa gttagggagg    13905
ctcgggccct gacactgcca gccccagtga gcatccctgg ctacctcggg attatgtgca    13965
agctgctttg tcctacattt cttttcatct gttcttattg ggagtgcttc tctctaataa    14025
aaattgattt cccacaaaat aggcaaagct gaacaaagat gaatgctttt gataagttgg    14085
gtttcacttc agttgaaaca atgtgataga atatccaggt gtggcatgat ggggcaggag    14145
gaggtgccta gagggaaaag ttattttgt ttcttagtgt tgtgttgtgg ggatgggaca    14205
gataagaata agatgtttat tgccctaatc atgctaagag actattattc aatatgcttt    14265
tcccgctttt ctaagaggaa taaacttaga caaattacat tataaacagt tcccctacta    14325
ctatctccca ctctagataa agccagtggg tggtatgggt cctttattc cttatagtat    14385 tatgccaaag aatcaactta ttttcattga agattataaa taaatgaagc ttgttatagc    14445
cataatgatt tgagtcagta taccattta cctataaaat gcaaaattca tccttgcaac    14505
cccattcacc aggagccttg aagcattttg tttactccaa aggccttgtc aaggaagcat    14565
aattttttgt tttgccttct tatttagtca gtttggtcat atttacttaa aaaacaaac    14625 tgaaaatcac actcctttat atgttgatat aactgatttt atagaatctg tctgttcttt    14685
gtttaacagg tctctgtaag caagcttgca agtgtatttt gtgtacattt tatctgaggt    14745
ggaaatgaaa attctaaaga gaaatatttt taaaagatat tgtatttatg ttgcttgtgt    14805
tgtagaataa agattcaaat gcattaaaaa tctggtacat gaaacaattg tgtttactga    14865
ataaatatat ataaataaaa aaaaaaaaaa                                     14895
```

<210> SEQ ID NO 7
<211> LENGTH: 2177
<212> TYPE: PRT
<213> ORGANISM: Homo sapiens

<400> SEQUENCE: 7

```
Met Glu Glu Ile Leu Arg Lys Leu Gln Lys Glu Ala Ser Gly Ser Lys
1               5                   10                  15

Tyr Lys Ala Ile Lys Glu Ser Cys Thr Trp Ala Leu Glu Thr Leu Gly
            20                  25                  30

Gly Leu Asp Thr Ile Val Lys Ile Pro Pro His Val Leu Arg Glu Lys
        35                  40                  45

Cys Leu Leu Pro Leu Gln Leu Ala Leu Glu Ser Lys Asn Val Lys Leu
    50                  55                  60

Ala Gln His Ala Leu Ala Gly Met Gln Lys Leu Leu Ser Glu Glu Arg
65                  70                  75                  80

Phe Val Ser Met Glu Thr Asp Ser Asp Glu Lys Gln Leu Leu Asn Gln
                85                  90                  95

Ile Leu Asn Ala Val Lys Val Thr Pro Ser Leu Asn Glu Asp Leu Gln
            100                 105                 110

Val Glu Val Met Lys Val Leu Leu Cys Ile Thr Tyr Thr Pro Thr Phe
        115                 120                 125

Asp Leu Asn Gly Ser Ala Val Leu Lys Ile Ala Glu Val Cys Ile Glu
    130                 135                 140

Thr Tyr Ile Ser Ser Cys His Gln Arg Ser Ile Asn Thr Ala Val Arg
145                 150                 155                 160
```

-continued

```
Ala Thr Leu Ser Gln Met Leu Ser Asp Leu Thr Leu Gln Leu Arg Gln
                165                 170                 175
Arg Gln Glu Asn Thr Ile Ile Glu Asn Pro Asp Val Pro Gln Asp Phe
            180                 185                 190
Gly Asn Gln Gly Ser Thr Val Glu Ser Leu Cys Asp Asp Val Val Ser
        195                 200                 205
Val Leu Thr Val Leu Cys Glu Lys Leu Gln Ala Ala Ile Asn Asp Ser
    210                 215                 220
Gln Gln Leu Gln Leu Leu Tyr Leu Glu Cys Ile Leu Ser Val Leu Ser
225                 230                 235                 240
Ser Ser Ser Ser Ser Met His Leu His Arg Arg Phe Thr Asp Leu Ile
                245                 250                 255
Trp Lys Asn Leu Cys Pro Ala Leu Ile Val Ile Leu Gly Asn Pro Ile
            260                 265                 270
His Asp Lys Thr Ile Thr Ser Ala His Thr Ser Ser Thr Ser Thr Ser
        275                 280                 285
Leu Glu Ser Asp Ser Ala Ser Pro Gly Val Ser Asp His Gly Arg Gly
    290                 295                 300
Ser Gly Cys Ser Cys Thr Ala Pro Ala Leu Ser Gly Pro Val Ala Arg
305                 310                 315                 320
Thr Ile Tyr Tyr Ile Ala Ala Glu Leu Val Arg Leu Val Gly Ser Val
                325                 330                 335
Asp Ser Met Lys Pro Val Leu Gln Ser Leu Tyr His Arg Val Leu Leu
            340                 345                 350
Tyr Pro Pro Pro Gln His Arg Val Glu Ala Ile Lys Ile Met Lys Glu
        355                 360                 365
Ile Leu Gly Ser Pro Gln Arg Leu Cys Asp Leu Ala Gly Pro Ser Ser
    370                 375                 380
Thr Glu Ser Glu Ser Arg Lys Arg Ser Ile Ser Lys Arg Lys Ser His
385                 390                 395                 400
Leu Asp Leu Leu Lys Leu Ile Met Asp Gly Met Thr Glu Ala Cys Ile
                405                 410                 415
Lys Gly Gly Ile Glu Ala Cys Tyr Ala Ala Val Ser Cys Val Cys Thr
            420                 425                 430
Leu Leu Gly Ala Leu Asp Glu Leu Ser Gln Gly Lys Gly Leu Ser Glu
        435                 440                 445
Gly Gln Val Gln Leu Leu Leu Arg Leu Glu Glu Leu Lys Asp Gly
    450                 455                 460
Ala Glu Trp Ser Arg Asp Ser Met Glu Ile Asn Glu Ala Asp Phe Arg
465                 470                 475                 480
Trp Gln Arg Arg Val Leu Ser Ser Glu His Thr Pro Trp Glu Ser Gly
                485                 490                 495
Asn Glu Arg Ser Leu Asp Ile Ser Ile Ser Val Thr Thr Asp Thr Gly
            500                 505                 510
Gln Thr Thr Leu Glu Gly Glu Leu Gly Gln Thr Thr Pro Glu Asp His
        515                 520                 525
Ser Gly Asn His Lys Asn Ser Leu Lys Ser Pro Ala Ile Pro Glu Gly
    530                 535                 540
Lys Glu Thr Leu Ser Lys Val Leu Glu Thr Glu Ala Val Asp Gln Pro
545                 550                 555                 560
Asp Val Val Gln Arg Ser His Thr Val Pro Tyr Pro Asp Ile Thr Asn
                565                 570                 575
```

-continued

```
Phe Leu Ser Val Asp Cys Arg Thr Arg Ser Tyr Gly Ser Arg Tyr Ser
            580                 585                 590
Glu Ser Asn Phe Ser Val Asp Asp Gln Asp Leu Ser Arg Thr Glu Phe
        595                 600                 605
Asp Ser Cys Asp Gln Tyr Ser Met Ala Ala Glu Lys Asp Ser Gly Arg
    610                 615                 620
Ser Asp Val Ser Asp Ile Gly Ser Asp Asn Cys Ser Leu Ala Asp Glu
625                 630                 635                 640
Glu Gln Thr Pro Arg Asp Cys Leu Gly His Arg Ser Leu Arg Thr Ala
                645                 650                 655
Ala Leu Ser Leu Lys Leu Leu Lys Asn Gln Glu Ala Asp Gln His Ser
            660                 665                 670
Ala Arg Leu Phe Ile Gln Ser Leu Glu Gly Leu Leu Pro Arg Leu Leu
        675                 680                 685
Ser Leu Ser Asn Val Glu Glu Val Asp Thr Ala Leu Gln Asn Phe Ala
    690                 695                 700
Ser Thr Phe Cys Ser Gly Met Met His Ser Pro Gly Phe Asp Gly Asn
705                 710                 715                 720
Ser Ser Leu Ser Phe Gln Met Leu Met Asn Ala Asp Ser Leu Tyr Thr
                725                 730                 735
Ala Ala His Cys Ala Leu Leu Leu Asn Leu Lys Leu Ser His Gly Asp
            740                 745                 750
Tyr Tyr Arg Lys Arg Pro Thr Leu Ala Pro Gly Val Met Lys Asp Phe
        755                 760                 765
Met Lys Gln Val Gln Thr Ser Gly Val Leu Met Val Phe Ser Gln Ala
    770                 775                 780
Trp Ile Glu Glu Leu Tyr His Gln Val Leu Asp Arg Asn Met Leu Gly
785                 790                 795                 800
Glu Ala Gly Tyr Trp Gly Ser Pro Glu Asp Asn Ser Leu Pro Leu Ile
                805                 810                 815
Thr Met Leu Thr Asp Ile Asp Gly Leu Glu Ser Ser Ala Ile Gly Gly
            820                 825                 830
Gln Leu Met Ala Ser Ala Ala Thr Glu Ser Pro Phe Ala Gln Ser Arg
        835                 840                 845
Arg Ile Asp Asp Ser Thr Val Ala Gly Val Ala Phe Ala Arg Tyr Ile
    850                 855                 860
Leu Val Gly Cys Trp Lys Asn Leu Ile Asp Thr Leu Ser Thr Pro Leu
865                 870                 875                 880
Thr Gly Arg Met Ala Gly Ser Ser Lys Gly Leu Ala Phe Ile Leu Gly
                885                 890                 895
Ala Glu Gly Ile Lys Glu Gln Asn Gln Lys Glu Arg Asp Ala Ile Cys
            900                 905                 910
Met Ser Leu Asp Gly Leu Arg Lys Ala Ala Arg Leu Ser Cys Ala Leu
        915                 920                 925
Gly Val Ala Ala Asn Cys Ala Ser Ala Leu Ala Gln Met Ala Ala Ala
    930                 935                 940
Ser Cys Val Gln Glu Glu Lys Glu Glu Arg Glu Ala Gln Glu Pro Ser
945                 950                 955                 960
Asp Ala Ile Thr Gln Val Lys Leu Lys Val Glu Gln Lys Leu Glu Gln
                965                 970                 975
Ile Gly Lys Val Gln Gly Val Trp Leu His Thr Ala His Val Leu Cys
            980                 985                 990
```

-continued

Met Glu Ala Ile Leu Ser Val Gly Leu Glu Met Gly Ser His Asn Pro
            995                1000                 1005

Asp Cys Trp Pro His Val Phe Arg Val Cys Glu Tyr Val Gly Thr
   1010            1015                 1020

Leu Glu His Asn His Phe Ser Asp Gly Ala Ser Gln Pro Pro Leu
   1025            1030                 1035

Thr Ile Ser Gln Pro Gln Lys Ala Thr Gly Ser Ala Gly Leu Leu
   1040            1045                 1050

Gly Asp Pro Glu Cys Glu Gly Ser Pro Pro Glu His Ser Pro Glu
   1055            1060                 1065

Gln Gly Arg Ser Leu Ser Thr Ala Pro Val Val Gln Pro Leu Ser
   1070            1075                 1080

Ile Gln Asp Leu Val Arg Glu Gly Ser Arg Gly Arg Ala Ser Asp
   1085            1090                 1095

Phe Arg Gly Gly Ser Leu Met Ser Gly Ser Ser Ala Ala Lys Val
   1100            1105                 1110

Val Leu Thr Leu Ser Thr Gln Ala Asp Arg Leu Phe Glu Asp Ala
   1115            1120                 1125

Thr Asp Lys Leu Asn Leu Met Ala Leu Gly Gly Phe Leu Tyr Gln
   1130            1135                 1140

Leu Lys Lys Ala Ser Gln Ser Gln Leu Phe His Ser Val Thr Asp
   1145            1150                 1155

Thr Val Asp Tyr Ser Leu Ala Met Pro Gly Glu Val Lys Ser Thr
   1160            1165                 1170

Gln Asp Arg Lys Ser Ala Leu His Leu Phe Arg Leu Gly Asn Ala
   1175            1180                 1185

Met Leu Arg Ile Val Arg Ser Lys Ala Arg Pro Leu Leu His Val
   1190            1195                 1200

Met Arg Cys Trp Ser Leu Val Ala Pro His Leu Val Glu Ala Ala
   1205            1210                 1215

Cys His Lys Glu Arg His Val Ser Gln Lys Ala Val Ser Phe Ile
   1220            1225                 1230

His Asp Ile Leu Thr Glu Val Leu Thr Asp Trp Asn Glu Pro Pro
   1235            1240                 1245

His Phe His Phe Asn Glu Ala Leu Phe Arg Pro Phe Glu Arg Ile
   1250            1255                 1260

Met Gln Leu Glu Leu Cys Asp Glu Asp Val Gln Asp Gln Val Val
   1265            1270                 1275

Thr Ser Ile Gly Glu Leu Val Glu Val Cys Ser Thr Gln Ile Gln
   1280            1285                 1290

Ser Gly Trp Arg Pro Leu Phe Ser Ala Leu Glu Thr Val His Gly
   1295            1300                 1305

Gly Asn Lys Ser Glu Met Lys Glu Tyr Leu Val Gly Asp Tyr Ser
   1310            1315                 1320

Met Gly Lys Gly Gln Ala Pro Val Phe Asp Val Phe Glu Ala Phe
   1325            1330                 1335

Leu Asn Thr Asp Asn Ile Gln Val Phe Ala Asn Ala Ala Thr Ser
   1340            1345                 1350

Tyr Ile Met Cys Leu Met Lys Phe Val Lys Gly Leu Gly Glu Val
   1355            1360                 1365

Asp Cys Lys Glu Ile Gly Asp Cys Ala Pro Ala Pro Gly Ala Pro
   1370            1375                 1380

-continued

Ser Thr Asp Leu Cys Leu Pro Ala Leu Asp Tyr Leu Arg Arg Cys
1385                1390                1395

Ser Gln Leu Leu Ala Lys Ile Tyr Lys Met Pro Leu Lys Pro Ile
1400                1405                1410

Phe Leu Ser Gly Arg Leu Ala Gly Leu Pro Arg Arg Leu Gln Glu
1415                1420                1425

Gln Ser Ala Ser Ser Glu Asp Gly Ile Glu Ser Val Leu Ser Asp
1430                1435                1440

Phe Asp Asp Asp Thr Gly Leu Ile Glu Val Trp Ile Ile Leu Leu
1445                1450                1455

Glu Gln Leu Thr Ala Ala Val Ser Asn Cys Pro Arg Gln His Gln
1460                1465                1470

Pro Pro Thr Leu Asp Leu Leu Phe Glu Leu Leu Arg Asp Val Thr
1475                1480                1485

Lys Thr Pro Gly Pro Gly Phe Gly Ile Tyr Ala Val Val His Leu
1490                1495                1500

Leu Leu Pro Val Met Ser Val Trp Leu Arg Arg Ser His Lys Asp
1505                1510                1515

His Ser Tyr Trp Asp Met Ala Ser Ala Asn Phe Lys His Ala Ile
1520                1525                1530

Gly Leu Ser Cys Glu Leu Val Val Glu His Ile Gln Ser Phe Leu
1535                1540                1545

His Ser Asp Ile Arg Tyr Glu Ser Met Ile Asn Thr Met Leu Lys
1550                1555                1560

Asp Leu Phe Glu Leu Leu Val Ala Cys Val Ala Lys Pro Thr Glu
1565                1570                1575

Thr Ile Ser Arg Val Gly Cys Ser Cys Ile Arg Tyr Val Leu Val
1580                1585                1590

Thr Ala Gly Pro Val Phe Thr Glu Glu Met Trp Arg Leu Ala Cys
1595                1600                1605

Cys Ala Leu Gln Asp Ala Phe Ser Ala Thr Leu Lys Pro Val Lys
1610                1615                1620

Asp Leu Leu Gly Cys Phe His Ser Gly Thr Glu Ser Phe Ser Gly
1625                1630                1635

Glu Gly Cys Gln Val Arg Val Ala Ala Pro Ser Ser Ser Pro Ser
1640                1645                1650

Ala Glu Ala Glu Tyr Trp Arg Ile Arg Ala Met Ala Gln Gln Val
1655                1660                1665

Phe Met Leu Asp Thr Gln Cys Ser Pro Lys Thr Pro Asn Asn Phe
1670                1675                1680

Asp His Ala Gln Ser Cys Gln Leu Ile Ile Glu Leu Pro Pro Asp
1685                1690                1695

Glu Lys Pro Asn Gly His Thr Lys Lys Ser Val Ser Phe Arg Glu
1700                1705                1710

Ile Val Val Ser Leu Leu Ser His Gln Val Leu Leu Gln Asn Leu
1715                1720                1725

Tyr Asp Ile Leu Leu Glu Glu Phe Val Lys Gly Pro Ser Pro Gly
1730                1735                1740

Glu Glu Lys Thr Ile Gln Val Pro Glu Ala Lys Leu Ala Gly Phe
1745                1750                1755

Leu Arg Tyr Ile Ser Met Gln Asn Leu Ala Val Ile Phe Asp Leu
1760                1765                1770

-continued

| | | | | | | | | | | | | | |
|---|---|---|---|---|---|---|---|---|---|---|---|---|---|
|Leu|Leu 1775|Asp|Ser|Tyr|Arg|Thr 1780|Ala|Arg|Glu|Phe|Asp 1785|Thr|Ser|Pro|
|Gly|Leu 1790|Lys|Cys|Leu|Leu|Lys 1795|Lys|Val|Ser|Gly|Ile 1800|Gly|Gly|Ala|
|Ala|Asn 1805|Leu|Tyr|Arg|Gln|Ser 1810|Ala|Met|Ser|Phe|Asn 1815|Ile|Tyr|Phe|
|His|Ala 1820|Leu|Val|Cys|Ala|Val 1825|Leu|Thr|Asn|Gln|Glu 1830|Thr|Ile|Thr|
|Ala|Glu 1835|Gln|Val|Lys|Lys|Val 1840|Leu|Phe|Glu|Asp|Asp 1845|Glu|Arg|Ser|
|Thr|Asp 1850|Ser|Ser|Gln|Gln|Cys 1855|Ser|Ser|Glu|Asp|Glu 1860|Asp|Ile|Phe|
|Glu|Glu 1865|Thr|Ala|Gln|Val|Ser 1870|Pro|Pro|Arg|Gly|Lys 1875|Glu|Lys|Arg|
|Gln|Trp 1880|Arg|Ala|Arg|Met|Pro 1885|Leu|Leu|Ser|Val|Gln 1890|Pro|Val|Ser|
|Asn|Ala 1895|Asp|Trp|Val|Trp|Leu 1900|Val|Lys|Arg|Leu|His 1905|Lys|Leu|Cys|
|Met|Glu 1910|Leu|Cys|Asn|Asn|Tyr 1915|Ile|Gln|Met|His|Leu 1920|Asp|Leu|Glu|
|Asn|Cys 1925|Met|Glu|Glu|Pro|Pro 1930|Ile|Phe|Lys|Gly|Asp 1935|Pro|Phe|Phe|
|Ile|Leu 1940|Pro|Ser|Phe|Gln|Ser 1945|Glu|Ser|Ser|Thr|Pro 1950|Ser|Thr|Gly|
|Gly|Phe 1955|Ser|Gly|Lys|Glu|Thr 1960|Pro|Ser|Glu|Asp|Asp 1965|Arg|Ser|Gln|
|Ser|Arg 1970|Glu|His|Met|Gly|Glu 1975|Ser|Leu|Ser|Leu|Lys 1980|Ala|Gly|Gly|
|Gly|Asp 1985|Leu|Leu|Leu|Pro|Pro 1990|Ser|Pro|Lys|Val|Glu 1995|Lys|Lys|Asp|
|Pro|Ser 2000|Arg|Lys|Lys|Glu|Trp 2005|Trp|Glu|Asn|Ala|Gly 2010|Asn|Lys|Ile|
|Tyr|Thr 2015|Met|Ala|Ala|Asp|Lys 2020|Thr|Ile|Ser|Lys|Leu 2025|Met|Thr|Glu|
|Tyr|Lys 2030|Lys|Arg|Lys|Gln|Gln 2035|His|Asn|Leu|Ser|Ala 2040|Phe|Pro|Lys|
|Glu|Val 2045|Lys|Val|Glu|Lys|Lys 2050|Gly|Glu|Pro|Leu|Gly 2055|Pro|Arg|Gly|
|Gln|Asp 2060|Ser|Pro|Leu|Leu|Gln 2065|Arg|Pro|Gln|His|Leu 2070|Met|Asp|Gln|
|Gly|Gln 2075|Met|Arg|His|Ser|Phe 2080|Ser|Ala|Gly|Pro|Glu 2085|Leu|Leu|Arg|
|Gln|Asp 2090|Lys|Arg|Pro|Arg|Ser 2095|Gly|Ser|Thr|Gly|Ser 2100|Ser|Leu|Ser|
|Val|Ser 2105|Val|Arg|Asp|Ala|Glu 2110|Ala|Gln|Ile|Gln|Ala 2115|Trp|Thr|Asn|
|Met|Val 2120|Leu|Thr|Val|Leu|Asn 2125|Gln|Ile|Gln|Ile|Leu 2130|Pro|Asp|Gln|
|Thr|Phe 2135|Thr|Ala|Leu|Gln|Pro 2140|Ala|Val|Phe|Pro|Cys 2145|Ile|Ser|Gln|

```
Leu Thr Cys His Val Thr Asp Ile Arg Val Arg Gln Ala Val Arg
    2150                2155                2160

Glu Trp Leu Gly Arg Val Gly Arg Val Tyr Asp Ile Ile Val
    2165                2170                2175

<210> SEQ ID NO 8
<211> LENGTH: 1457
<212> TYPE: DNA
<213> ORGANISM: Homo sapiens
<220> FEATURE:
<221> NAME/KEY: CDS
<222> LOCATION: (211)..(1110)

<400> SEQUENCE: 8
tccgtatgcg cgattcctgt gcgcgaagtt cgggtccgta gtgggctaag ggggagggtt      60
tcaaagggag cgcacttccg ctgcccttc tttcgccagc cttacgggcc cgaaccctcg     120 tgtgaaggt gcagtaccta agccggagcg gggtagaggc gggccggcac ccccttctga     180
cctccagtgc cgccggcctc aagatcagac atg gcc cag aac ttg aag gac ttg     234
                                 Met Ala Gln Asn Leu Lys Asp Leu
                                   1               5 gcg gga cgg ctg ccc gcc ggg ccc cgg ggc atg ggc acg gcc ctg aag     282
Ala Gly Arg Leu Pro Ala Gly Pro Arg Gly Met Gly Thr Ala Leu Lys
        10                  15                  20 ctg ttg ctg ggg gcc ggc gcc gtg gcc tac ggt gtg cgc gaa tct gtg     330
Leu Leu Leu Gly Ala Gly Ala Val Ala Tyr Gly Val Arg Glu Ser Val
 25                  30                  35                  40 ttc acc gtg gaa ggc ggg cac aga gcc atc ttc ttc aat cgg atc ggt     378
Phe Thr Val Glu Gly Gly His Arg Ala Ile Phe Phe Asn Arg Ile Gly
                 45                  50                  55 gga gtg cag cag gac act atc ctg gcc gag ggc ctt cac ttc agg atc     426
Gly Val Gln Gln Asp Thr Ile Leu Ala Glu Gly Leu His Phe Arg Ile
             60                  65                  70 cct tgg ttc cag tac ccc att atc tat gac att cgg gcc aga cct cga     474
Pro Trp Phe Gln Tyr Pro Ile Ile Tyr Asp Ile Arg Ala Arg Pro Arg
         75                  80                  85 aaa atc tcc tcc cct aca ggc tcc aaa gac cta cag atg gtg aat atc     522
Lys Ile Ser Ser Pro Thr Gly Ser Lys Asp Leu Gln Met Val Asn Ile
     90                  95                 100 tcc ctg cga gtg ttg tct cga ccc aat gct cag gag ctt cct agc atg     570
Ser Leu Arg Val Leu Ser Arg Pro Asn Ala Gln Glu Leu Pro Ser Met
105                 110                 115                 120 tac cag cgc cta ggg ctg gac tac gag gaa cga gtg ttg ccg tcc att     618
Tyr Gln Arg Leu Gly Leu Asp Tyr Glu Glu Arg Val Leu Pro Ser Ile
                125                 130                 135 gtc aac gag gtg ctc aag agt gtg gtg gcc aag ttc aat gcc tca cag     666
Val Asn Glu Val Leu Lys Ser Val Val Ala Lys Phe Asn Ala Ser Gln
            140                 145                 150 ctg atc acc cag cgg gcc cag gta tcc ctg ttg atc cgc cgg gag ctg     714
Leu Ile Thr Gln Arg Ala Gln Val Ser Leu Leu Ile Arg Arg Glu Leu
        155                 160                 165 aca gag agg gcc aag gac ttc agc ctc atc ctg gat gat gtg gcc atc     762
Thr Glu Arg Ala Lys Asp Phe Ser Leu Ile Leu Asp Asp Val Ala Ile
    170                 175                 180 aca gag ctg agc ttt agc cga gag tac aca gct gct gta gaa gcc aaa     810
Thr Glu Leu Ser Phe Ser Arg Glu Tyr Thr Ala Ala Val Glu Ala Lys
185                 190                 195                 200 caa gtg gcc cag cag gag gcc cag cgg gcc caa ttc ttg gta gaa aaa     858
Gln Val Ala Gln Gln Glu Ala Gln Arg Ala Gln Phe Leu Val Glu Lys
                205                 210                 215
```

```
gca aag cag gaa cag cgg cag aaa att gtg cag gcc gag ggt gag gcc    906
Ala Lys Gln Glu Gln Arg Gln Lys Ile Val Gln Ala Glu Gly Glu Ala
        220                 225                 230 gag gct gcc aag atg ctt gga gaa gca ctg agc aag aac cct ggc tac    954
Glu Ala Ala Lys Met Leu Gly Glu Ala Leu Ser Lys Asn Pro Gly Tyr
            235                 240                 245 atc aaa ctt cgc aag att cga gca gcc cag aat atc tcc aag acg atc   1002
Ile Lys Leu Arg Lys Ile Arg Ala Ala Gln Asn Ile Ser Lys Thr Ile
250                 255                 260 gcc aca tca cag aat cgt atc tat ctc aca gct gac aac ctt gtg ctg   1050
Ala Thr Ser Gln Asn Arg Ile Tyr Leu Thr Ala Asp Asn Leu Val Leu
265                 270                 275                 280 aac cta cag gat gaa agt ttc acc agg gga agt gac agc ctc atc aag   1098
Asn Leu Gln Asp Glu Ser Phe Thr Arg Gly Ser Asp Ser Leu Ile Lys
                285                 290                 295 ggt aag aaa tga gcctagtcac caagaactcc accccagag gaagtggatc        1150
Gly Lys Lys tgcttctcca gttttttgagg agccagccag gggtccagca cagccctacc ccgccccagt 1210
atcatgcgat ggtcccccac accggttccc tgaaccccctc ttggattaag gaagactgaa 1270
gactagcccc ttttctgggg aattactttc ctcctccctg tgttaactgg ggctgttggg  1330
gacagtgcgt gatttctcag tgatttccta cagtgttgtt ccctccctca aggctgggag  1390
gagataaaca ccaacccagg aattctcaat aaattttttat tacttaacct gaaaaaaaaa  1450
aaaaaaa                                                            1457

<210> SEQ ID NO 9
<211> LENGTH: 299
<212> TYPE: PRT
<213> ORGANISM: Homo sapiens

<400> SEQUENCE: 9

Met Ala Gln Asn Leu Lys Asp Leu Ala Gly Arg Leu Pro Ala Gly Pro
1               5                   10                  15

Arg Gly Met Gly Thr Ala Leu Lys Leu Leu Gly Ala Gly Ala Val
            20                  25                  30

Ala Tyr Gly Val Arg Glu Ser Val Phe Thr Val Glu Gly Gly His Arg
        35                  40                  45

Ala Ile Phe Phe Asn Arg Ile Gly Gly Val Gln Gln Asp Thr Ile Leu
    50                  55                  60

Ala Glu Gly Leu His Phe Arg Ile Pro Trp Phe Gln Tyr Pro Ile Ile
65                  70                  75                  80

Tyr Asp Ile Arg Ala Arg Pro Arg Lys Ile Ser Ser Pro Thr Gly Ser
                85                  90                  95

Lys Asp Leu Gln Met Val Asn Ile Ser Leu Arg Val Leu Ser Arg Pro
            100                 105                 110

Asn Ala Gln Glu Leu Pro Ser Met Tyr Gln Arg Leu Gly Leu Asp Tyr
        115                 120                 125

Glu Glu Arg Val Leu Pro Ser Ile Val Asn Glu Val Leu Lys Ser Val
    130                 135                 140

Val Ala Lys Phe Asn Ala Ser Gln Leu Ile Thr Gln Arg Ala Gln Val
145                 150                 155                 160

Ser Leu Leu Ile Arg Arg Glu Leu Thr Glu Arg Ala Lys Asp Phe Ser
                165                 170                 175

Leu Ile Leu Asp Asp Val Ala Ile Thr Glu Leu Ser Phe Ser Arg Glu
            180                 185                 190
```

```
Tyr Thr Ala Ala Val Glu Ala Lys Gln Val Ala Gln Gln Glu Ala Gln
            195                 200                 205

Arg Ala Gln Phe Leu Val Glu Lys Ala Lys Glu Gln Arg Gln Lys
    210                 215                 220

Ile Val Gln Ala Glu Gly Glu Ala Glu Ala Ala Lys Met Leu Gly Glu
225                 230                 235                 240

Ala Leu Ser Lys Asn Pro Gly Tyr Ile Lys Leu Arg Lys Ile Arg Ala
                245                 250                 255

Ala Gln Asn Ile Ser Lys Thr Ile Ala Thr Ser Gln Asn Arg Ile Tyr
            260                 265                 270

Leu Thr Ala Asp Asn Leu Val Leu Asn Leu Gln Asp Glu Ser Phe Thr
        275                 280                 285

Arg Gly Ser Asp Ser Leu Ile Lys Gly Lys Lys
    290                 295

<210> SEQ ID NO 10
<211> LENGTH: 1343
<212> TYPE: DNA
<213> ORGANISM: Homo sapiens
<220> FEATURE:
<221> NAME/KEY: CDS
<222> LOCATION: (211)..(996)

<400> SEQUENCE: 10
tccgtatgcg cgattcctgt gcgcgaagtt cgggtccgta gtgggctaag ggggagggtt      60
tcaaagggag cgcacttccg ctgccctttc tttcgccagc cttacgggcc cgaaccctcg     120
tgtgaagggt gcagtaccta gccggagcg gggtagaggc gggccggcac ccccttctga     180
cctccagtgc cgccggcctc aagatcagac atg gcc cag aac ttg aag gac ttg     234
                                  Met Ala Gln Asn Leu Lys Asp Leu
                                    1               5 gcg gga cgg ctg ccc gcc ggg ccc cgg ggc atg ggc acg gcc ctg aag      282
Ala Gly Arg Leu Pro Ala Gly Pro Arg Gly Met Gly Thr Ala Leu Lys
         10                  15                  20 ctg ttg ctg ggg gcc ggc gcc gtg gcc tac ggt gtg cgc gaa tct gtg      330
Leu Leu Leu Gly Ala Gly Ala Val Ala Tyr Gly Val Arg Glu Ser Val
 25                  30                  35                  40 ttc acc gtg gaa ggc ggg cac aga gcc atc ttc ttc aat cgg atc ggt      378
Phe Thr Val Glu Gly Gly His Arg Ala Ile Phe Phe Asn Arg Ile Gly
                 45                  50                  55 gga gtg cag cag gac act atc ctg gcc gag ggc ctt cac ttc agg atc      426
Gly Val Gln Gln Asp Thr Ile Leu Ala Glu Gly Leu His Phe Arg Ile
             60                  65                  70 cct tgg ttc cag tac ccc att atc tat gac att cgg gcc aga cct cga      474
Pro Trp Phe Gln Tyr Pro Ile Ile Tyr Asp Ile Arg Ala Arg Pro Arg
         75                  80                  85 aaa atc tcc tcc cct aca ggc tcc aaa gac cta cag atg gtg aat atc      522
Lys Ile Ser Ser Pro Thr Gly Ser Lys Asp Leu Gln Met Val Asn Ile
 90                  95                 100 tcc ctg cga gtg ttg tct cga ccc aat gct cag gag ctt cct agc atg      570
Ser Leu Arg Val Leu Ser Arg Pro Asn Ala Gln Glu Leu Pro Ser Met
105                 110                 115                 120 tac cag cgc cta ggg ctg gac tac gag gaa cga gtg ttg ccg tcc att      618
Tyr Gln Arg Leu Gly Leu Asp Tyr Glu Glu Arg Val Leu Pro Ser Ile
                125                 130                 135 gtc aac gag gtg ctc aag agt gtg gtg gcc aag ttc aat gcc tca cag      666
Val Asn Glu Val Leu Lys Ser Val Val Ala Lys Phe Asn Ala Ser Gln
            140                 145                 150
```

|  |  |
|---|---|
| ctg atc acc cag cgg gcc cag gta tcc ctg ttg atc cgc cgg gag ctg<br>Leu Ile Thr Gln Arg Ala Gln Val Ser Leu Leu Ile Arg Arg Glu Leu<br>　　　 155　　　　　　　　　 160　　　　　　　　　 165 | 714 |
| aca gag agg gcc aag gac ttc agc ctc atc ctg gat gat gtg gcc atc<br>Thr Glu Arg Ala Lys Asp Phe Ser Leu Ile Leu Asp Asp Val Ala Ile<br>170　　　　　　　　　 175　　　　　　　　　 180 | 762 |
| aca gag ctg agc ttt agc cga gag tac aca gct gct gta gaa gcc aaa<br>Thr Glu Leu Ser Phe Ser Arg Glu Tyr Thr Ala Ala Val Glu Ala Lys<br>185　　　　　　　　　 190　　　　　　　　　 195　　　　　　　　　 200 | 810 |
| caa gtg gca ctg agc aag aac cct ggc tac atc aaa ctt cgc aag att<br>Gln Val Ala Leu Ser Lys Asn Pro Gly Tyr Ile Lys Leu Arg Lys Ile<br>　　　　　　　　　 205　　　　　　　　　 210　　　　　　　　　 215 | 858 |
| cga gca gcc cag aat atc tcc aag acg atc gcc aca tca cag aat cgt<br>Arg Ala Ala Gln Asn Ile Ser Lys Thr Ile Ala Thr Ser Gln Asn Arg<br>　　　　 220　　　　　　　　　 225　　　　　　　　　 230 | 906 |
| atc tat ctc aca gct gac aac ctt gtg ctg aac cta cag gat gaa agt<br>Ile Tyr Leu Thr Ala Asp Asn Leu Val Leu Asn Leu Gln Asp Glu Ser<br>　　　 235　　　　　　　　　 240　　　　　　　　　 245 | 954 |
| ttc acc agg gga agt gac agc ctc atc aag ggt aag aaa tga<br>Phe Thr Arg Gly Ser Asp Ser Leu Ile Lys Gly Lys Lys<br>250　　　　　　　　　 255　　　　　　　　　 260 | 996 |
| gcctagtcac caagaactcc accccagag gaagtggatc tgcttctcca gttttgagg | 1056 |
| agccagccag ggtccagca cagccctacc ccgccccagt atcatgcgat ggtcccccac | 1116 |
| accggttccc tgaaccccctc ttggattaag gaagactgaa gactagcccc ttttctgggg | 1176 |
| aattactttc ctcctccctg tgttaactgg ggctgttggg gacagtgcgt gatttctcag | 1236 |
| tgatttccta cagtgttgtt ccctccctca aggctgggag gagataaaca ccaacccagg | 1296 |
| aattctcaat aaattttttat tacttaacct gaaaaaaaaa aaaaaaa | 1343 |

<210> SEQ ID NO 11
<211> LENGTH: 261
<212> TYPE: PRT
<213> ORGANISM: Homo sapiens

<400> SEQUENCE: 11

Met Ala Gln Asn Leu Lys Asp Leu Ala Gly Arg Leu Pro Ala Gly Pro
1               5                   10                  15

Arg Gly Met Gly Thr Ala Leu Lys Leu Leu Gly Ala Gly Ala Val
            20                  25                  30

Ala Tyr Gly Val Arg Glu Ser Val Phe Thr Val Glu Gly Gly His Arg
        35                  40                  45

Ala Ile Phe Phe Asn Arg Ile Gly Gly Val Gln Gln Asp Thr Ile Leu
    50                  55                  60

Ala Glu Gly Leu His Phe Arg Ile Pro Trp Phe Gln Tyr Pro Ile Ile
65                  70                  75                  80

Tyr Asp Ile Arg Ala Arg Pro Arg Lys Ile Ser Ser Pro Thr Gly Ser
                85                  90                  95

Lys Asp Leu Gln Met Val Asn Ile Ser Leu Arg Val Leu Ser Arg Pro
            100                 105                 110

Asn Ala Gln Glu Leu Pro Ser Met Tyr Gln Arg Leu Gly Leu Asp Tyr
        115                 120                 125

Glu Glu Arg Val Leu Pro Ser Ile Val Asn Glu Val Leu Lys Ser Val
    130                 135                 140

Val Ala Lys Phe Asn Ala Ser Gln Leu Ile Thr Gln Arg Ala Gln Val
145                 150                 155                 160

```
Ser Leu Leu Ile Arg Arg Glu Leu Thr Glu Arg Ala Lys Asp Phe Ser
            165                 170                 175

Leu Ile Leu Asp Asp Val Ala Ile Thr Glu Leu Ser Phe Ser Arg Glu
        180                 185                 190

Tyr Thr Ala Ala Val Glu Ala Lys Gln Val Ala Leu Ser Lys Asn Pro
        195                 200                 205

Gly Tyr Ile Lys Leu Arg Lys Ile Arg Ala Ala Gln Asn Ile Ser Lys
        210                 215                 220

Thr Ile Ala Thr Ser Gln Asn Arg Ile Tyr Leu Thr Ala Asp Asn Leu
225                 230                 235                 240

Val Leu Asn Leu Gln Asp Glu Ser Phe Thr Arg Gly Ser Asp Ser Leu
            245                 250                 255

Ile Lys Gly Lys Lys
            260

<210> SEQ ID NO 12
<211> LENGTH: 6330
<212> TYPE: DNA
<213> ORGANISM: Homo sapiens
<220> FEATURE:
<221> NAME/KEY: CDS
<222> LOCATION: (235)..(2022)

<400> SEQUENCE: 12
aggagctggc ggagggcgtt cgtcctggga ctgcacttgc tcccgtcggg tcgcccggct     60
tcaccggacc cgcaggctcc cggggcaggg ccggggccag agctcgcgtg tcggcgggac   120
atgcgctgcg tcgcctctaa cctcgggctg tgctctttt ccaggtggcc cgccggtttc   180
tgagccttct gccctgcggg gacacggtct gcaccctgcc cgcggccacg acc atg     237
                                                              Met
                                                               1
```

| | | | | | | | | | | | | | | | | |
|---|---|---|---|---|---|---|---|---|---|---|---|---|---|---|---|---|
| acc | atg | acc | ctc | cac | acc | aaa | gca | tct | ggg | atg | gcc | cta | ctg | cat | cag | 285 |
| Thr | Met | Thr | Leu | His | Thr | Lys | Ala | Ser | Gly | Met | Ala | Leu | Leu | His | Gln | |
| | | | 5 | | | | | 10 | | | | | 15 | | | |

```
atc caa ggg aac gag ctg gag ccc ctg aac cgt ccg cag ctc aag atc     333
Ile Gln Gly Asn Glu Leu Glu Pro Leu Asn Arg Pro Gln Leu Lys Ile
        20                  25                  30 ccc ctg gag cgg ccc ctg ggc gag gtg tac ctg gac agc agc aag ccc     381
Pro Leu Glu Arg Pro Leu Gly Glu Val Tyr Leu Asp Ser Ser Lys Pro
35                  40                  45 gcc gtg tac aac tac ccc gag ggc gcc gcc tac gag ttc aac gcc gcg     429
Ala Val Tyr Asn Tyr Pro Glu Gly Ala Ala Tyr Glu Phe Asn Ala Ala
50                  55                  60                  65 gcc gcc gcc aac gcg cag gtc tac ggt cag acc ggc ctc ccc tac ggc     477
Ala Ala Ala Asn Ala Gln Val Tyr Gly Gln Thr Gly Leu Pro Tyr Gly
            70                  75                  80 ccc ggg tct gag gct gcg gcg ttc ggc tcc aac ggc ctg ggg ggt ttc     525
Pro Gly Ser Glu Ala Ala Ala Phe Gly Ser Asn Gly Leu Gly Gly Phe
                85                  90                  95 ccc cca ctc aac agc gtg tct ccg agc ccg ctg atg cta ctg cac ccg     573
Pro Pro Leu Asn Ser Val Ser Pro Ser Pro Leu Met Leu Leu His Pro
            100                 105                 110 ccg ccg cag ctg tcg cct ttc ctg cag ccc cac ggc cag cag gtg ccc     621
Pro Pro Gln Leu Ser Pro Phe Leu Gln Pro His Gly Gln Gln Val Pro
        115                 120                 125 tac tac ctg gag aac gag ccc agc ggc tac acg gtg cgc gag gcc ggc     669
Tyr Tyr Leu Glu Asn Glu Pro Ser Gly Tyr Thr Val Arg Glu Ala Gly
130                 135                 140                 145
```

-continued

| | |
|---|---|
| ccg ccg gca ttc tac agg cca aat tca gat aat cga cgc cag ggt ggc<br>Pro Pro Ala Phe Tyr Arg Pro Asn Ser Asp Asn Arg Arg Gln Gly Gly<br>                                    150                        155                        160 | 717 |
| aga gaa aga ttg gcc agt acc aat gac aag gga agt atg gct atg gaa<br>Arg Glu Arg Leu Ala Ser Thr Asn Asp Lys Gly Ser Met Ala Met Glu<br>                                    165                        170                        175 | 765 |
| tct gcc aag gag act cgc tac tgt gca gtg tgc aat gac tat gct tca<br>Ser Ala Lys Glu Thr Arg Tyr Cys Ala Val Cys Asn Asp Tyr Ala Ser<br>                                    180                        185                        190 | 813 |
| ggc tac cat tat gga gtc tgg tcc tgt gag ggc tgc aag gcc ttc ttc<br>Gly Tyr His Tyr Gly Val Trp Ser Cys Glu Gly Cys Lys Ala Phe Phe<br>                  195                        200                        205 | 861 |
| aag aga agt att caa gga cat aac gac tat atg tgt cca gcc acc aac<br>Lys Arg Ser Ile Gln Gly His Asn Asp Tyr Met Cys Pro Ala Thr Asn<br>210                        215                        220                        225 | 909 |
| cag tgc acc att gat aaa aac agg agg aag agc tgc cag gcc tgc cgg<br>Gln Cys Thr Ile Asp Lys Asn Arg Arg Lys Ser Cys Gln Ala Cys Arg<br>                                    230                        235                        240 | 957 |
| ctc cgc aaa tgc tac gaa gtg gga atg atg aaa ggt ggg ata cga aaa<br>Leu Arg Lys Cys Tyr Glu Val Gly Met Met Lys Gly Gly Ile Arg Lys<br>                  245                        250                        255 | 1005 |
| gac cga aga gga ggg aga atg ttg aaa cac aag cgc cag aga gat gat<br>Asp Arg Arg Gly Gly Arg Met Leu Lys His Lys Arg Gln Arg Asp Asp<br>                                    260                        265                        270 | 1053 |
| ggg gag ggc agg ggt gaa gtg ggg tct gct gga gac atg aga gct gcc<br>Gly Glu Gly Arg Gly Glu Val Gly Ser Ala Gly Asp Met Arg Ala Ala<br>                  275                        280                        285 | 1101 |
| aac ctt tgg cca agc ccg ctc atg atc aaa cgc tct aag aag aac agc<br>Asn Leu Trp Pro Ser Pro Leu Met Ile Lys Arg Ser Lys Lys Asn Ser<br>290                        295                        300                        305 | 1149 |
| ctg gcc ttg tcc ctg acg gcc gac cag atg gtc agt gcc ttg ttg gat<br>Leu Ala Leu Ser Leu Thr Ala Asp Gln Met Val Ser Ala Leu Leu Asp<br>                                    310                        315                        320 | 1197 |
| gct gag ccc ccc ata ctc tat tcc gag tat gat cct acc aga ccc ttc<br>Ala Glu Pro Pro Ile Leu Tyr Ser Glu Tyr Asp Pro Thr Arg Pro Phe<br>                  325                        330                        335 | 1245 |
| agt gaa gct tcg atg atg ggc tta ctg acc aac ctg gca gac agg gag<br>Ser Glu Ala Ser Met Met Gly Leu Leu Thr Asn Leu Ala Asp Arg Glu<br>                                    340                        345                        350 | 1293 |
| ctg gtt cac atg atc aac tgg gcg aag agg gtg cca ggc ttt gtg gat<br>Leu Val His Met Ile Asn Trp Ala Lys Arg Val Pro Gly Phe Val Asp<br>                  355                        360                        365 | 1341 |
| ttg acc ctc cat gat cag gtc cac ctt cta gaa tgt gcc tgg cta gag<br>Leu Thr Leu His Asp Gln Val His Leu Leu Glu Cys Ala Trp Leu Glu<br>370                        375                        380                        385 | 1389 |
| atc ctg atg att ggt ctc gtc tgg cgc tcc atg gag cac cca ggg aag<br>Ile Leu Met Ile Gly Leu Val Trp Arg Ser Met Glu His Pro Gly Lys<br>                                    390                        395                        400 | 1437 |
| cta ctg ttt gct cct aac ttg ctc ttg gac agg aac cag gga aaa tgt<br>Leu Leu Phe Ala Pro Asn Leu Leu Leu Asp Arg Asn Gln Gly Lys Cys<br>                  405                        410                        415 | 1485 |
| gta gag ggc atg gtg gag atc ttc gac atg ctg ctg gct aca tca tct<br>Val Glu Gly Met Val Glu Ile Phe Asp Met Leu Leu Ala Thr Ser Ser<br>                                    420                        425                        430 | 1533 |
| cgg ttc cgc atg atg aat ctg cag gga gag gag ttt gtg tgc ctc aaa<br>Arg Phe Arg Met Met Asn Leu Gln Gly Glu Glu Phe Val Cys Leu Lys<br>                  435                        440                        445 | 1581 |
| tct att att ttg ctt aat tct gga gtg tac aca ttt ctg tcc agc acc<br>Ser Ile Ile Leu Leu Asn Ser Gly Val Tyr Thr Phe Leu Ser Ser Thr<br>450                        455                        460                        465 | 1629 |

```
ctg aag tct ctg gaa gag aag gac cat atc cac cga gtc ctg gac aag      1677
Leu Lys Ser Leu Glu Glu Lys Asp His Ile His Arg Val Leu Asp Lys
                470                 475                 480 atc aca gac act ttg atc cac ctg atg gcc aag gca ggc ctg acc ctg      1725
Ile Thr Asp Thr Leu Ile His Leu Met Ala Lys Ala Gly Leu Thr Leu
            485                 490                 495 cag cag cag cac cag cgg ctg gcc cag ctc ctc ctc atc ctc tcc cac      1773
Gln Gln Gln His Gln Arg Leu Ala Gln Leu Leu Leu Ile Leu Ser His
        500                 505                 510 atc agg cac atg agt aac aaa ggc atg gag cat ctg tac agc atg aag      1821
Ile Arg His Met Ser Asn Lys Gly Met Glu His Leu Tyr Ser Met Lys
    515                 520                 525 tgc aag aac gtg gtg ccc ctc tat gac ctg ctg gag atg ctg gac          1869
Cys Lys Asn Val Val Pro Leu Tyr Asp Leu Leu Glu Met Leu Asp
530                 535                 540                 545 gcc cac cgc cta cat gcg ccc act agc cgt gga ggg gca tcc gtg gag      1917
Ala His Arg Leu His Ala Pro Thr Ser Arg Gly Gly Ala Ser Val Glu
                550                 555                 560 gag acg gac caa agc cac ttg gcc act gcg ggc tct act tca tcg cat      1965
Glu Thr Asp Gln Ser His Leu Ala Thr Ala Gly Ser Thr Ser Ser His
            565                 570                 575 tcc ttg caa aag tat tac atc acg ggg gag gca gag ggt ttc cct gcc      2013
Ser Leu Gln Lys Tyr Tyr Ile Thr Gly Glu Ala Glu Gly Phe Pro Ala
        580                 585                 590 acg gtc tga gagctccctg gctcccacac ggttcagata atccctgctg              2062
Thr Val
    595 cattttaccc tcatcatgca ccactttagc caaattctgt ctcctgcata cactccggca    2122 tgcatccaac accaatggct ttctagatga gtggccattc atttgcttgc tcagttctta    2182 gtggcacatc ttctgtcttc tgttgggaac agccaaaggg attccaaggc taaatctttg    2242 taacagctct ctttccccct tgctatgtta ctaagcgtga ggattcccgt agctcttcac    2302 agctgaactc agtctatggg ttggggctca gataactctg tgcatttaag ctacttgtag    2362 agacccaggc ctggagagta gacattttgc ctctgataag cactttttaa atggctctaa    2422 gaataagcca cagcaaagaa tttaaagtgg ctccttttaat tggtgacttg gagaaagcta   2482 ggtcaagggt ttattatagc accctcttgt attcctatgg caatgcatcc ttttatgaaa    2542 gtggtacacc ttaaagcttt tatatgactg tagcagagta tctggtgatt gtcaattcat    2602 tcccctata ggaatacaag gggcacacag gaaggcaga tcccctagtt ggcaagacta      2662 ttttaacttg atacactgca gattcagatg tgctgaaagc tctgcctctg ctttccggt     2722 catgggttcc agttaattca tgcctcccat ggacctatgg agagcagcaa gttgatctta    2782 gttaagtctc cctatatgag ggataagttc ctgattttg ttttattttt tgtgttacaa     2842 aagaaagccc tccctccctg aacttgcagt aaggtcagct tcaggacctg ttccagtggg    2902 cactgtactt ggatcttccc ggcgtgtgtg tgccttacac aggggtgaac tgttcactgt    2962 ggtgatgcat gatgagggta aatggtagtt gaaaggagca ggggccctgg tgttgcattt    3022 agccctgggg catggagctg aacagtactt gtgcaggatt gttgtggcta ctagagaaca    3082 agagggaaag tagggcagaa actggataca gttctgaggc acagccagac ttgctcaggg    3142 tggccctgcc acaggctgca gctacctagg aacattcctt gcagaccccg cattgccctt    3202 tgggggtgcc ctgggatccc tggggtagtc cagctcttct tcatttccca gcgtggccct    3262 ggttggaaga agcagctgtc acagctgctg tagacagctg tgttcctaca attgcccag     3322 caccctgggg cacgggagaa gggtgtggga cgttgctgtc actactcagg ctgactgggg    3382
```

```
cctggtcaga ttacgtatgc ccttggtggt ttagagataa tccaaaatca gggtttggtt    3442
tggggaagaa aatcctcccc cttcctcccc cgccccgttc cctaccgcct ccactcctgc    3502
cagctcattt ccttcaattt cctttgacct ataggctaaa aagaaaggc tcattccagc    3562 cacagggcag cctccctgg gcctttgctt ctctagcaca attatgggtt acttcctttt    3622
tcttaacaaa aagaatgtt tgatttcctc tgggtgacct tattgtctgt aattgaaacc    3682
ctattgagag gtgatgtctg tgttagccaa tgacccaggt gagctgctcg ggcttctctt    3742
ggtatgtctt gtttggaaaa gtggatttca ttcatttctg attgtccagt taagtgatca    3802
ccaaaggact gagaatctgg gagggcaaaa aaaaaaaaa agttttatg tgcacttaaa    3862 tttgggggaca atttatgta tctgtgttaa ggatatgttt aagaacataa ttcttttgtt    3922
gctgtttgtt taagaagcac cttagtttgt ttaagaagca ccttatatag tataatatat    3982
atttttttga aattacattg cttgtttatc agacaattga atgtagtaat tctgttctgg    4042 attttaatttg actgggttaa catgcaaaaa ccaaggaaaa atatttagtt tttttttttt    4102 ttttttgtata cttttcaagc taccttgtca tgtatacagt catttatgcc taaagcctgg    4162
tgattattca tttaaatgaa gatcacattt catatcaact tttgtatcca cagtagacaa    4222
aatagcacta atccagatgc ctattgttgg atactgaatg acagacaatc ttatgtagca    4282
aagattatgc ctgaaaagga aaattattca gggcagctaa ttttgctttt accaaaatat    4342
cagtagtaat atttttggac agtagctaat gggtcagtgg gttcttttta atgtttatac    4402
ttagattttc ttttaaaaaa attaaaataa aacaaaaaaa aattctagg actagacgat    4462 gtaataccag ctaaagccaa acaattatac agtggaaggt tttacattat tcatccaatg    4522
tgtttctatt catgttaaga tactactaca tttgaagtgg gcagagaaca tcagatgatt    4582
gaaatgttcg cccaggggtc tccagcaact ttggaaatct ctttgtattt ttacttgaag    4642
tgccactaat ggacagcaga tattttctgg ctgatgttgg tattgggtgt aggaacatga    4702
tttaaaaaaa aactcttgcc tctgcttttcc cccactctga ggcaagttaa aatgtaaaag    4762
atgtgattta tctggggggc tcaggtatgg tggggaagtg gattcaggaa tctggggaat    4822
ggcaaatata ttaagaagag tattgaaagt atttggagga aaatggttaa ttctgggtgt    4882
gcaccagggt tcagtagagt ccacttctgc cctggagacc acaaatcaac tagctccatt    4942
tacagccatt tctaaaatgg cagcttcagt tctagagaag aaagaacaac atcagcagta    5002
aagtccatgg aatagctagt ggtctgtgtt tcttttcgcc attgcctagc ttgccgtaat    5062
gattctataa tgccatcatg cagcaattat gagaggctag gtcatccaaa gagaagaccc    5122
tatcaatgta ggttgcaaaa tctaaccct aaggaagtgc agtctttgat ttgatttccc    5182
tagtaacctt gcagatatgt ttaaccaagc catagcccat gccttttgag ggctgaacaa    5242
ataagggact tactgataat ttactttga tcacattaag gtgttctcac cttgaaatct    5302
tatacactga aatggccatt gatttaggcc actggcttag agtactcctt cccctgcatg    5362
acactgatta caaatacttt cctattcata ctttccaatt atgagatgga ctgtgggtac    5422
tgggagtgat cactaacacc atagtaatgt ctaatattca caggcagatc tgcttgggga    5482
agctagttat gtgaaaggca aatagagtca tacagtagcc caaaaggcaa ccataattct    5542
ctttggtgca ggtcttggga gcgtgatcta gattacactg caccattccc aagttaatcc    5602
cctgaaaact tactctcaac tggagcaaat gaactttggt cccaaatatc catcttttca    5662
gtagcgttaa ttatgctctg tttccaactg catttccttt ccaattgaat taaagtgtgg    5722
cctcgttttt agtcatttaa aattgttttc taagtaattg ctgcctctat tatggcactt    5782
```

| | | |
|---|---|---|
| caattttgca ctgtcttttg agattcaaga aaaatttcta ttctttttt tgcatccaat | | 5842 |
| tgtgcctgaa cttttaaaat atgtaaatgc tgccatgttc caaacccatc gtcagtgtgt | | 5902 |
| gtgtttagag ctgtgcaccc tagaaacaac atattgtccc atgagcaggt gcctgagaca | | 5962 |
| cagacccctt tgcattcaca gagaggtcat tggttataga acttgaatt aataagtgac | | 6022 |
| attatgccag tttctgttct ctcacaggtg ataaacaatg cttttgtgc actacatact | | 6082 |
| cttcagtgta gagctcttgt tttatgggaa aaggctcaaa tgccaaattg tgtttgatgg | | 6142 |
| attaatatgc cctttgccg atgcatacta ttactgatgt gactcggttt tgtcgcagct | | 6202 |
| ttgctttgtt taatgaaaca cacttgtaaa cctcttttgc actttgaaaa agaatccagc | | 6262 |
| gggatgctcg agcacctgta aacaattttc tcaacctatt tgatgttcaa ataaagaatt | | 6322 |
| aaactaaa | | 6330 |

<210> SEQ ID NO 13
<211> LENGTH: 595
<212> TYPE: PRT
<213> ORGANISM: Homo sapiens

<400> SEQUENCE: 13

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

```
Asp Gly Glu Gly Arg Gly Glu Val Gly Ser Ala Gly Asp Met Arg Ala
            275                 280                 285

Ala Asn Leu Trp Pro Ser Pro Leu Met Ile Lys Arg Ser Lys Lys Asn
290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
            355                 360                 365

Asp Leu Thr Leu His Asp Gln Val His Leu Leu Glu Cys Ala Trp Leu
370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
435                 440                 445

Lys Ser Ile Ile Leu Leu Asn Ser Gly Val Tyr Thr Phe Leu Ser Ser
450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
            515                 520                 525

Lys Cys Lys Asn Val Val Pro Leu Tyr Asp Leu Leu Leu Glu Met Leu
530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
            595

<210> SEQ ID NO 14
<211> LENGTH: 2169
<212> TYPE: DNA
<213> ORGANISM: Homo sapiens
<220> FEATURE:
<221> NAME/KEY: CDS
<222> LOCATION: (469)..(2061)

<400> SEQUENCE: 14
ctcggtcttt aaaaggaaga aggggcttat cgttaagtcg cttgtgatct tttcagtttc     60
tccagctgct ggcttttggg acacccactc ccccgccagg aggcagttgc aagcgcggag    120
```

-continued

| | |
|---|---|
| gctgcgagaa ataactgcct cttgaaactt gcagggcgaa gagcaggcgg cgagcgctgg | 180 |
| gccggggagg gaccacccga gctgcgacgg gctctggggc tgcggggcag ggctggcgcc | 240 |
| cggagcctga gctgcaggag gtgcgctcgc tttcctcaac aggtggcggc ggggcgcgcg | 300 |
| ccggagacc cccctaatg cgggaaaagc acgtgtccgc attttagaga aggcaaggcc | 360 |
| ggtgtgttta tctgcaagcc attatacttg cccacgaatc tttgagaaca ttataatgac | 420 |
| ctttgtgcct cttcttgcaa ggtgttttct cagctgttat ctcaagac atg gat ata | 477 |
|                                                                                                                       Met Asp Ile | |
|                                                                                                                        1 | |
| aaa aac tca cca tct agc ctt aat tct cct tcc tcc tac aac tgc agt | 525 |
| Lys Asn Ser Pro Ser Ser Leu Asn Ser Pro Ser Ser Tyr Asn Cys Ser | |
|    5                        10                        15 | |
| caa tcc atc tta ccc ctg gag cac ggc tcc ata tac ata cct tcc tcc | 573 |
| Gln Ser Ile Leu Pro Leu Glu His Gly Ser Ile Tyr Ile Pro Ser Ser | |
| 20                     25                        30                        35 | |
| tat gta gac agc cac cat gaa tat cca gcc atg aca ttc tat agc cct | 621 |
| Tyr Val Asp Ser His His Glu Tyr Pro Ala Met Thr Phe Tyr Ser Pro | |
|                  40                        45                        50 | |
| gct gtg atg aat tac agc att ccc agc aat gtc act aac ttg gaa ggt | 669 |
| Ala Val Met Asn Tyr Ser Ile Pro Ser Asn Val Thr Asn Leu Glu Gly | |
|                  55                        60                        65 | |
| ggg cct ggt cgg cag acc aca agc cca aat gtg ttg tgg cca aca cct | 717 |
| Gly Pro Gly Arg Gln Thr Thr Ser Pro Asn Val Leu Trp Pro Thr Pro | |
|          70                        75                        80 | |
| ggg cac ctt tct cct tta gtg gtc cat cgc cag tta tca cat ctg tat | 765 |
| Gly His Leu Ser Pro Leu Val Val His Arg Gln Leu Ser His Leu Tyr | |
|         85                       90                        95 | |
| gcg gaa cct caa aag agt ccc tgg tgt gaa gca aga tcg cta gaa cac | 813 |
| Ala Glu Pro Gln Lys Ser Pro Trp Cys Glu Ala Arg Ser Leu Glu His | |
| 100                    105                  110                  115 | |
| acc tta cct gta aac aga gag aca ctg aaa agg aag gtt agt ggg aac | 861 |
| Thr Leu Pro Val Asn Arg Glu Thr Leu Lys Arg Lys Val Ser Gly Asn | |
|                 120                  125                  130 | |
| cgt tgc gcc agc cct gtt act ggt cca ggt tca aag agg gat gct cac | 909 |
| Arg Cys Ala Ser Pro Val Thr Gly Pro Gly Ser Lys Arg Asp Ala His | |
|                 135                  140                  145 | |
| ttc tgc gct gtc tgc agc gat tac gca tcg gga tat cac tat gga gtc | 957 |
| Phe Cys Ala Val Cys Ser Asp Tyr Ala Ser Gly Tyr His Tyr Gly Val | |
|               150                  155                  160 | |
| tgg tcg tgt gaa gga tgt aag gcc ttt ttt aaa aga agc att caa gga | 1005 |
| Trp Ser Cys Glu Gly Cys Lys Ala Phe Phe Lys Arg Ser Ile Gln Gly | |
|             165                  170                  175 | |
| cat aat gat tat att tgt cca gct aca aat cag tgt aca atc gat aaa | 1053 |
| His Asn Asp Tyr Ile Cys Pro Ala Thr Asn Gln Cys Thr Ile Asp Lys | |
| 180                    185                  190                  195 | |
| aac cgg cgc aag agc tgc cag gcc tgc cga ctt cgg aag tgt tac gaa | 1101 |
| Asn Arg Arg Lys Ser Cys Gln Ala Cys Arg Leu Arg Lys Cys Tyr Glu | |
|                 200                  205                  210 | |
| gtg gga atg gtg aag tgt ggc tcc cgg aga gag aga tgt ggg tac cgc | 1149 |
| Val Gly Met Val Lys Cys Gly Ser Arg Arg Glu Arg Cys Gly Tyr Arg | |
|               215                  220                  225 | |
| ctt gtg cgg aga cag aga agt gcc gac gag cag ctg cac tgt gcc ggc | 1197 |
| Leu Val Arg Arg Gln Arg Ser Ala Asp Glu Gln Leu His Cys Ala Gly | |
|             230                  235                  240 | |
| aag gcc aag aga agt ggc ggc cac gcg ccc cga gtg cgg gag ctg ctg | 1245 |
| Lys Ala Lys Arg Ser Gly Gly His Ala Pro Arg Val Arg Glu Leu Leu | |
|     245                        250                        255 | |

```
ctg gac gcc ctg agc ccc gag cag cta gtg ctc acc ctc ctg gag gct    1293
Leu Asp Ala Leu Ser Pro Glu Gln Leu Val Leu Thr Leu Leu Glu Ala
260                 265                 270                 275 gag ccg ccc cat gtg ctg atc agc cgc ccc agt gcg ccc ttc acc gag    1341
Glu Pro Pro His Val Leu Ile Ser Arg Pro Ser Ala Pro Phe Thr Glu
                280                 285                 290 gcc tcc atg atg atg tcc ctg acc aag ttg gcc gac aag gag ttg gta    1389
Ala Ser Met Met Met Ser Leu Thr Lys Leu Ala Asp Lys Glu Leu Val
            295                 300                 305 cac atg atc agc tgg gcc aag aag att ccc ggc ttt gtg gag ctc agc    1437
His Met Ile Ser Trp Ala Lys Lys Ile Pro Gly Phe Val Glu Leu Ser
        310                 315                 320 ctg ttc gac caa gtg cgg ctc ttg gag agc tgt tgg atg gag gtg tta    1485
Leu Phe Asp Gln Val Arg Leu Leu Glu Ser Cys Trp Met Glu Val Leu
325                 330                 335 atg atg ggg ctg atg tgg cgc tca att gac cac ccc ggc aag ctc atc    1533
Met Met Gly Leu Met Trp Arg Ser Ile Asp His Pro Gly Lys Leu Ile
340                 345                 350                 355 ttt gct cca gat ctt gtt ctg gac agg gat gag ggg aaa tgc gta gaa    1581
Phe Ala Pro Asp Leu Val Leu Asp Arg Asp Glu Gly Lys Cys Val Glu
                360                 365                 370 gga att ctg gaa atc ttt gac atg ctc ctg gca act act tca agg ttt    1629
Gly Ile Leu Glu Ile Phe Asp Met Leu Leu Ala Thr Thr Ser Arg Phe
            375                 380                 385 cga gag tta aaa ctc caa cac aaa gaa tat ctc tgt gtc aag gcc atg    1677
Arg Glu Leu Lys Leu Gln His Lys Glu Tyr Leu Cys Val Lys Ala Met
        390                 395                 400 atc ctg ctc aat tcc agt atg tac cct ctg gtc aca gcg acc cag gat    1725
Ile Leu Leu Asn Ser Ser Met Tyr Pro Leu Val Thr Ala Thr Gln Asp
405                 410                 415 gct gac agc agc cgg aag ctg gct cac ttg ctg aac gcc gtg acc gat    1773
Ala Asp Ser Ser Arg Lys Leu Ala His Leu Leu Asn Ala Val Thr Asp
420                 425                 430                 435 gct ttg gtt tgg gtg att gcc aag agc ggc atc tcc tcc cag cag caa    1821
Ala Leu Val Trp Val Ile Ala Lys Ser Gly Ile Ser Ser Gln Gln Gln
                440                 445                 450 tcc atg cgc ctg gct aac ctc ctg atg ctc ctg tcc cac gtc agg cat    1869
Ser Met Arg Leu Ala Asn Leu Leu Met Leu Leu Ser His Val Arg His
            455                 460                 465 gcg agt aac aag ggc atg gaa cat ctg ctc aac atg aag tgc aaa aat    1917
Ala Ser Asn Lys Gly Met Glu His Leu Leu Asn Met Lys Cys Lys Asn
        470                 475                 480 gtg gtc cca gtg tat gac ctg ctg ctg gag atg ctg aat gcc cac gtg    1965
Val Val Pro Val Tyr Asp Leu Leu Leu Glu Met Leu Asn Ala His Val
485                 490                 495 ctt cgc ggg tgc aag tcc tcc atc acg ggg tcc gag tgc agc ccg gca    2013
Leu Arg Gly Cys Lys Ser Ser Ile Thr Gly Ser Glu Cys Ser Pro Ala
500                 505                 510                 515 gag gac agt aaa agc aaa gag ggc tcc cag aac cca cag tct cag tga    2061
Glu Asp Ser Lys Ser Lys Glu Gly Ser Gln Asn Pro Gln Ser Gln
                520                 525                 530 cgcctggccc tgaggtgaac tggcccacag aggtcacagg ctgaagcgtg aactccagtg   2121
tgtcaggagc ctgggcttca tctttctgct gtgtggtccc tcatttgg               2169

<210> SEQ ID NO 15
<211> LENGTH: 530
<212> TYPE: PRT
<213> ORGANISM: Homo sapiens
```

```
<400> SEQUENCE: 15

Met Asp Ile Lys Asn Ser Pro Ser Ser Leu Asn Ser Pro Ser Ser Tyr
1               5                   10                  15

Asn Cys Ser Gln Ser Ile Leu Pro Leu Glu His Gly Ser Ile Tyr Ile
            20                  25                  30

Pro Ser Ser Tyr Val Asp Ser His His Glu Tyr Pro Ala Met Thr Phe
        35                  40                  45

Tyr Ser Pro Ala Val Met Asn Tyr Ser Ile Pro Ser Asn Val Thr Asn
    50                  55                  60

Leu Glu Gly Gly Pro Gly Arg Gln Thr Thr Ser Pro Asn Val Leu Trp
65                  70                  75                  80

Pro Thr Pro Gly His Leu Ser Pro Leu Val Val His Arg Gln Leu Ser
                85                  90                  95

His Leu Tyr Ala Glu Pro Gln Lys Ser Pro Trp Cys Glu Ala Arg Ser
            100                 105                 110

Leu Glu His Thr Leu Pro Val Asn Arg Glu Thr Leu Lys Arg Lys Val
        115                 120                 125

Ser Gly Asn Arg Cys Ala Ser Pro Val Thr Gly Pro Gly Ser Lys Arg
    130                 135                 140

Asp Ala His Phe Cys Ala Val Cys Ser Asp Tyr Ala Ser Gly Tyr His
145                 150                 155                 160

Tyr Gly Val Trp Ser Cys Glu Gly Cys Lys Ala Phe Phe Lys Arg Ser
                165                 170                 175

Ile Gln Gly His Asn Asp Tyr Ile Cys Pro Ala Thr Asn Gln Cys Thr
            180                 185                 190

Ile Asp Lys Asn Arg Arg Lys Ser Cys Gln Ala Cys Arg Leu Arg Lys
        195                 200                 205

Cys Tyr Glu Val Gly Met Val Lys Cys Gly Ser Arg Arg Glu Arg Cys
    210                 215                 220

Gly Tyr Arg Leu Val Arg Arg Gln Arg Ser Ala Asp Glu Gln Leu His
225                 230                 235                 240

Cys Ala Gly Lys Ala Lys Arg Ser Gly Gly His Ala Pro Arg Val Arg
                245                 250                 255

Glu Leu Leu Leu Asp Ala Leu Ser Pro Glu Gln Leu Val Leu Thr Leu
            260                 265                 270

Leu Glu Ala Glu Pro Pro His Val Leu Ile Ser Arg Pro Ser Ala Pro
        275                 280                 285

Phe Thr Glu Ala Ser Met Met Met Ser Leu Thr Lys Leu Ala Asp Lys
    290                 295                 300

Glu Leu Val His Met Ile Ser Trp Ala Lys Lys Ile Pro Gly Phe Val
305                 310                 315                 320

Glu Leu Ser Leu Phe Asp Gln Val Arg Leu Leu Glu Ser Cys Trp Met
                325                 330                 335

Glu Val Leu Met Met Gly Leu Met Trp Arg Ser Ile Asp His Pro Gly
            340                 345                 350

Lys Leu Ile Phe Ala Pro Asp Leu Val Leu Asp Arg Asp Glu Gly Lys
        355                 360                 365

Cys Val Glu Gly Ile Leu Glu Ile Phe Asp Met Leu Leu Ala Thr Thr
    370                 375                 380

Ser Arg Phe Arg Glu Leu Lys Leu Gln His Lys Glu Tyr Leu Cys Val
385                 390                 395                 400

Lys Ala Met Ile Leu Leu Asn Ser Ser Met Tyr Pro Leu Val Thr Ala
                405                 410                 415
```

```
Thr Gln Asp Ala Asp Ser Ser Arg Lys Leu Ala His Leu Leu Asn Ala
        420                 425                 430
Val Thr Asp Ala Leu Val Trp Val Ile Ala Lys Ser Gly Ile Ser Ser
    435                 440                 445
Gln Gln Gln Ser Met Arg Leu Ala Asn Leu Leu Met Leu Leu Ser His
450                 455                 460
Val Arg His Ala Ser Asn Lys Gly Met Glu His Leu Leu Asn Met Lys
465                 470                 475                 480
Cys Lys Asn Val Val Pro Val Tyr Asp Leu Leu Leu Glu Met Leu Asn
                485                 490                 495
Ala His Val Leu Arg Gly Cys Lys Ser Ser Ile Thr Gly Ser Glu Cys
                500                 505                 510
Ser Pro Ala Glu Asp Ser Lys Ser Lys Glu Gly Ser Gln Asn Pro Gln
            515                 520                 525
Ser Gln
    530

<210> SEQ ID NO 16
<211> LENGTH: 9
<212> TYPE: PRT
<213> ORGANISM: Artificial Sequence
<220> FEATURE:
<223> OTHER INFORMATION: an HA-tag peptide

<400> SEQUENCE: 16

Tyr Pro Tyr Asp Val Pro Asp Tyr Ala
1               5

<210> SEQ ID NO 17
<211> LENGTH: 11
<212> TYPE: PRT
<213> ORGANISM: Artificial Sequence
<220> FEATURE:
<223> OTHER INFORMATION: PHB2 peptide containing Ser39

<400> SEQUENCE: 17

Tyr Gly Val Arg Glu Ser Val Phe Thr Val Glu
1               5                   10

<210> SEQ ID NO 18
<211> LENGTH: 20
<212> TYPE: DNA
<213> ORGANISM: Artificial Sequence
<220> FEATURE:
<223> OTHER INFORMATION: An artificially synthesized primer sequence for
      BIG3

<400> SEQUENCE: 18
cttgacaagg cctttggagt                                               20

<210> SEQ ID NO 19
<211> LENGTH: 20
<212> TYPE: DNA
<213> ORGANISM: Artificial Sequence
<220> FEATURE:
<223> OTHER INFORMATION: An artificially synthesized primer sequence for
      BIG3

<400> SEQUENCE: 19
caatatgctt ttcccgcttt                                               20
```

```
<210> SEQ ID NO 20
<211> LENGTH: 20
<212> TYPE: DNA
<213> ORGANISM: Artificial Sequence
<220> FEATURE:
<223> OTHER INFORMATION: An artificially synthesized primer sequence for
      beta 2-MG

<400> SEQUENCE: 20
aacttagagg tggggagcag                                              20

<210> SEQ ID NO 21
<211> LENGTH: 22
<212> TYPE: DNA
<213> ORGANISM: Artificial Sequence
<220> FEATURE:
<223> OTHER INFORMATION: An artificially synthesized primer sequence for
      beta 2-MG

<400> SEQUENCE: 21
cacaaccatg ccttacttta tc                                           22
```

PEPTIDE DERIVATIVE AND PHARMACEUTICAL COMPOSITION CONTAINING SAME

CROSS-REFERENCE TO RELATED APPLICATIONS

The present application is a § 371 National Phase Application of PCT/JP2018/026904, filed Jul. 18, 2018, which application claims the benefit of Japanese Patent Application No. JP 2017-140101, filed Jul. 19, 2017, the entire contents of which are incorporated by reference in their entireties for all purposes herein.

TECHNICAL FIELD

The present invention relates to peptide derivatives useful in cancer therapy, and pharmaceutical compositions comprising the same.

The present application claims the benefit of Japanese Patent Application No. 2017-140101, filed on Jul. 19, 2017, the entire contents of which are incorporated herein by reference.

BACKGROUND ART

Estrogen-receptor α (ERα) plays a key role in the development and progression of breast cancer. The current endocrine therapies for breast cancer mainly target ERα signaling, and use selective ERα modulators (for example, tamoxifen and raloxifene), ERα down-regulators (for example, fulvestrant), and aromatase inhibitors (AI) (NPLs 1 to 3). Among these therapies, a method that uses tamoxifen, which inhibits breast cancer cell proliferation through competitive binding to ERα, is a standard therapy for patients with ERα-positive breast cancer. However, tamoxifen therapy is often ineffective, and the patient may die from recurrent endocrine therapy-resistant tumors (NPLs 4 and 5). Furthermore, compared with tamoxifen, AI, which blocks estrogen synthesis, provides substantial clinical effects such as good efficacy, significant increase in relapse-free survival period, and a prolonged time to disease recurrence in postmenopausal women; however, some patients who have undergone AI treatment still relapse (NPLs 6 and 7). The precise molecular events having effects on the efficacy of these endocrine therapies remain unknown.

A complex formed between brefeldin A-inhibited guanine nucleotide-exchange protein 3 (BIG3), which is a cancer specific protein, and prohibitin 2 (PHB2), which is a tumor suppressor, plays a key role in estrogen signaling regulation in ERα-positive breast cancer (NPLs 8 and 9). BIG3 binds to PHB2 to inhibit the ability of PHB2, which suppresses the estrogen-dependent transcriptional activation, and thereby causes constitutive ERα activation.

Based on these findings, strategies of making PHB2 exhibit its tumor suppressive activity by dissociating PHB2 from its complex with BIG3 through inhibition of the BIG3-PHB2 interaction, may become a novel therapy for breast cancer. Based on this strategy, the present inventors have previously developed a dominant negative peptide of BIG3, which specifically inhibits the BIG3-PHB2 interaction (PTL 1). This peptide has been confirmed to suppress breast cancer growth by reactivating the tumor suppressive activity of PHB2 to inhibit ERα-signaling pathways that bring about the growth of breast cancer (PTL 1).

CITATION LIST

Patent Literature

[PTL 1] WO 2013/018690

Non-Patent Literature

[NPL 1] Johnston, S. R., Clin. Cancer Res. 16, 1979-1987 (2010).
[NPL 2] Fisher, B. et al., J. Natl. Cancer Inst. 97, 1652-1662 (2005).
[NPL 3] Jordan, V. C., Nature Rev. Drug Discov. 2, 205-213 (2003).
[NPL 4] Clarke, R. et al., Pharmacol. Rev. 53, 25-71 (2001).
[NPL 5] Fisher, B. et al., J. Natl. Cancer Inst. 93, 684-690 (2001).
[NPL 6] Chlebowski, R. et al., Breast 2, S1-11 (2009).
[NPL 7] Chumsri, S. et al., J. Steroid Biochem. Mol. Biol. 125, 13-22 (2011).
[NPL 8] Kim, J. W. et al., Cancer Sci. 100, 1468-1478 (2009).
[NPL 9] Yoshimaru, T. et al., Nat. Commun. 4, 2443 (2013).
[NPL 10] Yoshimaru, T. et al., Sci Rep. 7(1), 1821 (2017)

SUMMARY OF INVENTION

Technical Problem

As mentioned above, growth suppression actions on breast cancer cells by a dominant negative peptide of BIG 3 has been elucidated. However, the stability of the known dominant negative peptide cannot be said to be high, and the duration of inhibitory effects on the BIG3-PHB2 interaction is not that long. Then, the present inventors discovered that the duration of inhibitory effects on the BIG3-PHB2 interaction is improved by introducing a stapling structure (bridging structure) into the above-mentioned dominant negative peptide molecule (PCT/JP2017/001187, and Yoshimaru, T. et al., Sci Rep. 7(1), 1821 (2017)). Peptides to which a stapling structure has been introduced (stapled peptides; stERAP No. 12 and such) were confirmed to show more stable effects of suppressing breast cancer growth.

The above-mentioned stapled peptides prolonged the duration of the inhibitory effects on the BIG3-PHB2 interaction. However, inhibitory effects that last even longer are desired for clinical applications.

Therefore, an objective of the present invention is to provide peptides having longer lasting inhibitory effects on the BIG3-PHB2 interaction.

Solution to Problem

The present inventors previously discovered that the duration of inhibitory effects on the BIG3-PHB2 interaction is improved by introducing a stapling structure into the above-mentioned dominant negative peptide molecule, and now the present inventors completed the present invention by discovering that stability is enhanced by further increasing the number of intramolecular crosslinks. More specifically, the present invention provides the following peptides and uses thereof:

[1] a peptide comprising an amino acid sequence in which at least two pairs of amino acid residues are substituted with the same number of stapling structures in the amino acid sequence of SEQ ID NO: 4 or SEQ ID NO: 5, or a salt thereof;

[2] the peptide or the salt thereof of [1], wherein two pairs of amino acid residues are substituted with two stapling structures;

[3] the peptide or the salt thereof of [1] or [2], wherein the two pairs of amino acid residues are (a) and (b) below:
(a) the third and seventh amino acid residues from the N terminus of the amino acid sequence of SEQ ID NO: 4; and
(b) the eighth and twelfth amino acid residues from the N terminus of the amino acid sequence of SEQ ID NO: 4;

[4] the peptide or the salt thereof of [1] or [2], wherein the two pairs or amino acid residues are (c) and (d) below:
(c) the third and seventh amino acid residues from the N terminus of the amino acid sequence of SEQ ID NO: 5; and
(d) the tenth and fourteenth amino acid residues from the N terminus of the amino acid sequence of SEQ ID NO: 5;

[5] the peptide or the salt thereof of any one of [1] to [4], wherein the stapling structure is represented by Formula (I) below:

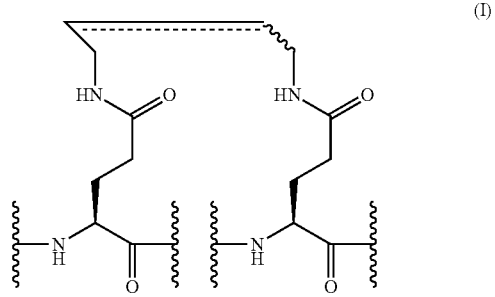 [SMILES: *N[C@@H](CCC(=O)NCCCCNC(=O)CC[C@H](N*)C(*)=O)C(*)=O]

(I)

(wherein, the double line drawn by a solid line and a dashed line indicates a single bond or a double bond);

[6] the peptide or the salt thereof of [5], wherein the stapling structure is represented by Formula (II) below:

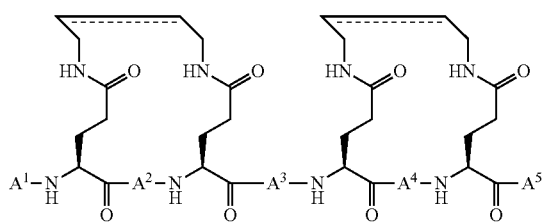

(II)

(wherein, the double line drawn by a solid line and a dashed line indicates a single bond or a double bond;
the combination of $A^1$, $A^2$, $A^3$, $A^4$, and $A^5$ is selected from the following:
$A^1$=QM, $A^2$=SDL, $A^3$=-, $A^4$=QLR, and $A^5$=R; and
$A^1$=QM, $A^2$=SDL, $A^3$=LQ, $A^4$=RQR, and $A^5$=OH;
wherein "-" indicates a peptide bond with no additional amino acid residue (that is, two stapling structures are connected); and "OH" indicates that one end of the above stapling structure constitutes the C terminus of the peptide derivative);

[7] the peptide or the salt thereof of any one of [1] to [6], wherein either one or both of N-terminal and C-terminal amino acid residues have been modified;

[8] the peptide or the salt thereof of [7], wherein either one or both of N-terminal and C-terminal amino acid residues have been modified by any one or a combination of acetylation, amidation, and HA tagging;

[9] the peptide or the salt thereof of [8], wherein the N-terminal amino acid residue is acetylated and the C-terminal amino acid residue is amidated;

[10] the peptide or the salt thereof of any one of [1] to [9], wherein all the amino acid residues have been substituted with D-form amino acid residues;

[11] a peptide which is a retro-inverso form of the peptide of any one of [1] to [9], or a salt thereof;

[12] a pharmaceutical composition comprising the peptide or the salt thereof of any on of [1] to [11] and a pharmaceutically acceptable carrier;

[13] the pharmaceutical composition of [12], which is for cancer therapy;

[14] the pharmaceutical composition of [13], wherein the cancer is breast cancer or prostate cancer; and

[15] the pharmaceutical composition of [13] or [14], wherein the cancer is estrogen receptor-positive cancer.

Alternatively, the present invention provides a method for cancer therapy, which comprises the step of administering the peptide or the salt thereof of any one of the above-mentioned [1] to [11] to a subject in need of the therapy. Furthermore, the present invention relates to use of the peptide or the salt thereof of any one of the above-mentioned [1] to [11] in the production of pharmaceutical compositions for cancer therapy. The present invention also relates to use of the peptide or the salt thereof of any one of the above-mentioned [1] to [11] in cancer therapy. Additionally, the present invention relates to a method of producing a pharmaceutical composition for cancer therapy, which comprises the step of mixing or formulating the peptide or the salt thereof of any one of the above-mentioned [1] to [11] with a carrier.

Effects of the Invention

Peptides having longer lasting inhibitory effects on the BIG3-PHB2 interaction are provided by the present invention. Pharmaceutical compositions comprising a peptide of the present invention may be applied to cancer therapy.

BRIEF DESCRIPTION OF DRAWINGS

FIG. 1 shows schematic diagrams of double stapled ERAPs (No. 45 and No. 46).

(FIGS. 2A and B) Human breast cancer cell line MCF-7 cells were treated with double stapled ERAP No. 45 (FIG. 2A) or double stapled ERAP No. 46 (FIG. 2B). Immediately thereafter, the cells were stimulated with 10 nM estrogen, and inhibitory effects were evaluated every 24 hours up to 96 hours by the MTT assay. Data represent the mean±standard deviation of three independent experiments. (FIG. 2C) Sigmoidal curves for the peptide concentrations (0.01, 0.05, 0.1, 0.5, 1, 5, and 10 μM) of single stapled ERAP (filled circle), double stapled ERAP No. 45 (filled triangle), or double stapled ERAP No. 46 (filled square), versus the percentage of growth suppression are shown.

FIG. 3 shows the chymotrypsin resistance of double stapled ERAPs. The chromatograms for double stapled ERAP No. 45 (A) and double stapled ERAP No. 46 (B), when a double stapled ERAP was reacted with chymotrypsin at 37° C. for 24 hours, are shown. In the experiment, the double stapled ERAP-chymotrypsin reaction solutions were subjected to high performance liquid chromatography (reverse-phase column, 0.3 mL/min flow rate, gradient elution (solution A: 0.1% trifluoroacetic acid; solution B: 0.1% trifluoroacetic acid/acetonitrile, A/B=90/10 (0-20 min) to 40/60 (20-80 min))), and detection was carried out by UV at 210 nm.

FIG. 6 shows a scheme for synthesis of an amino acid derivative used for the synthesis of stapled ERAPs. (i) to (vi) indicate reagents and amino acid synthesis conditions for each of the reactions: (i) 2,4-dimethoxybenzaldehyde, AcOH, MgSO$_4$, CH$_2$Cl$_2$; (ii) NaBH$_4$, MeOH, CH$_2$Cl$_2$, 87% yield (two steps); (iii) Compound 2, EDC.HCl, DIPEA, CH$_2$Cl$_2$, 76% yield; (iv) LiOH.H$_2$O, THF, MeOH, H$_2$O, 92% yield; (v) TBSOTf, 2,6-lutidine, CH$_2$Cl$_2$; (vi) Fmoc-OSu, Na$_2$CO$_3$, THF, H$_2$O, 90% yield (two steps).

FIG. 7 shows a scheme for stapling synthesis on ERAP by ring-closing olefin metathesis.

FIG. 8 shows a scheme for stapling synthesis on ERAP through intramolecular amidation.

Figure 2A:
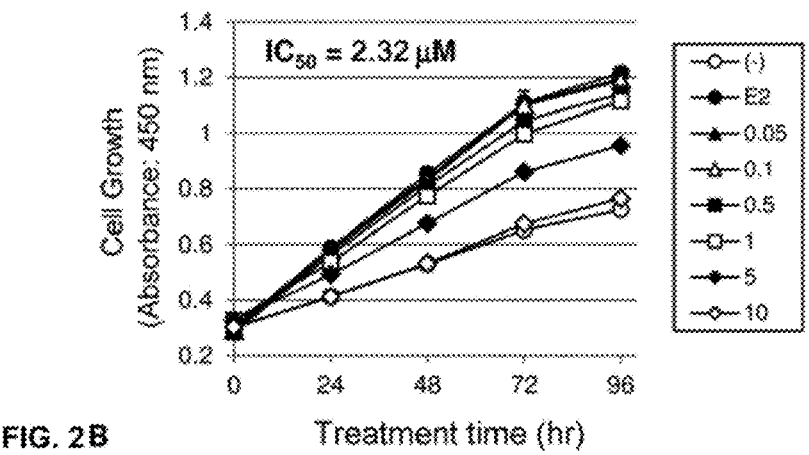
FIGS. 2A-C show that double stapled ERAPs suppress the growth of an estrogen-dependent human breast cancer cell line stably for a long time.

(B) It was shown that the PKCα activity of a breast cancer cell line transfected with an ESR1 mutant is PI3K-dependent. MCF-7 cells transfected with each ESR1 mutant were treated for 24 hours with PI3K inhibitor wortmannin at 100 nM and then subjected to immunoprecipitation using an anti-PKCα antibody, and PKCα activities on the PHB2 peptide carrying Ser39 were measured. Data represent the mean±standard error of three independent experiments (NS: no statistical significance; ***P<0.001). (C) Immunoblots are shown which indicate that the phosphorylated PKCα of MCF-7 cells transfected with an ESR1 mutant is PI3K-dependent. MCF-7 cells transfected with each ESR1 mutant were treated for 24 hours with stERAP and wortmannin and then subjected to immunoprecipitation using an anti-PKCα antibody, and immunoblot analyses were performed using the antibodies indicated in the drawing.

Figure 11:
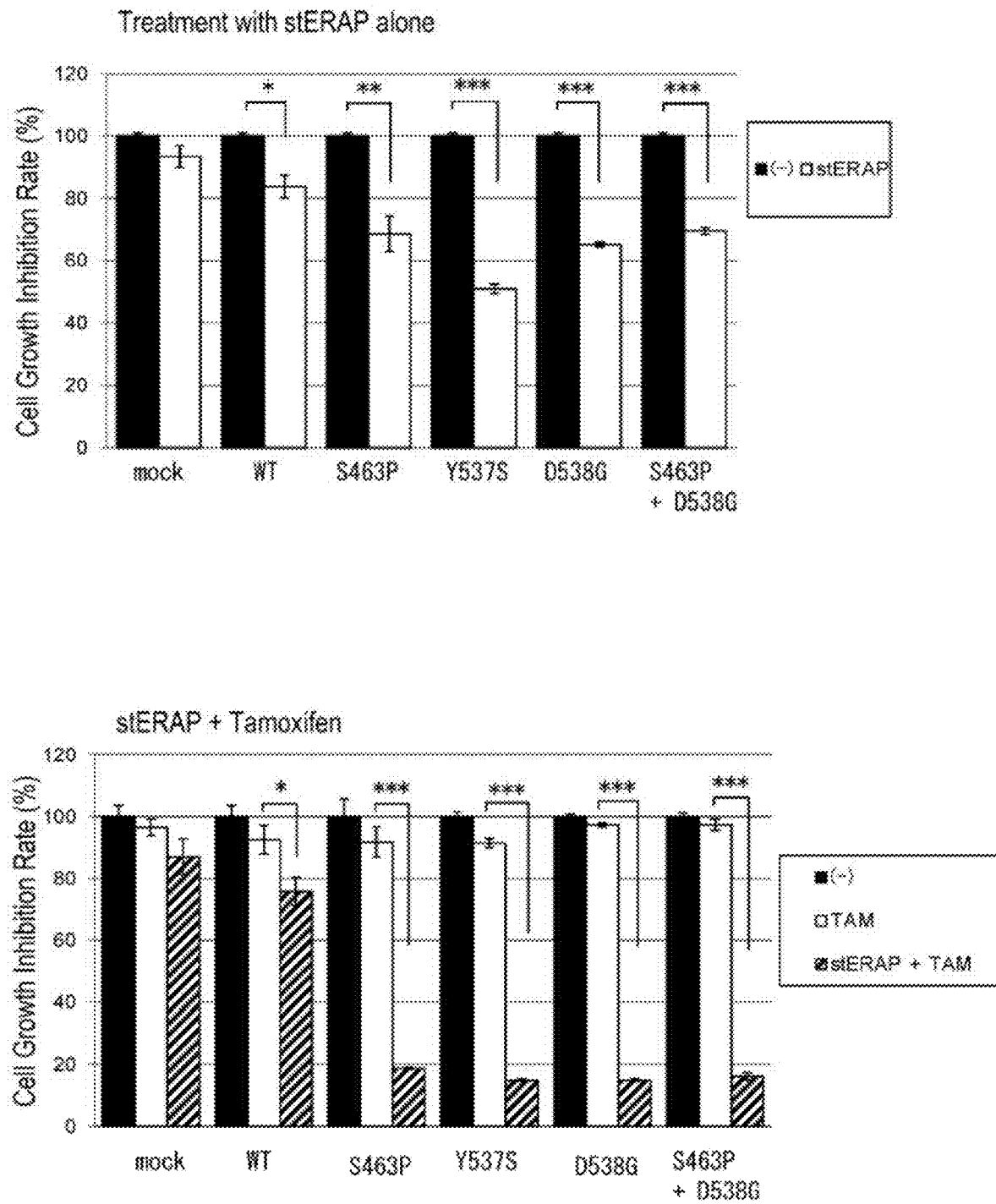
Figure 11:
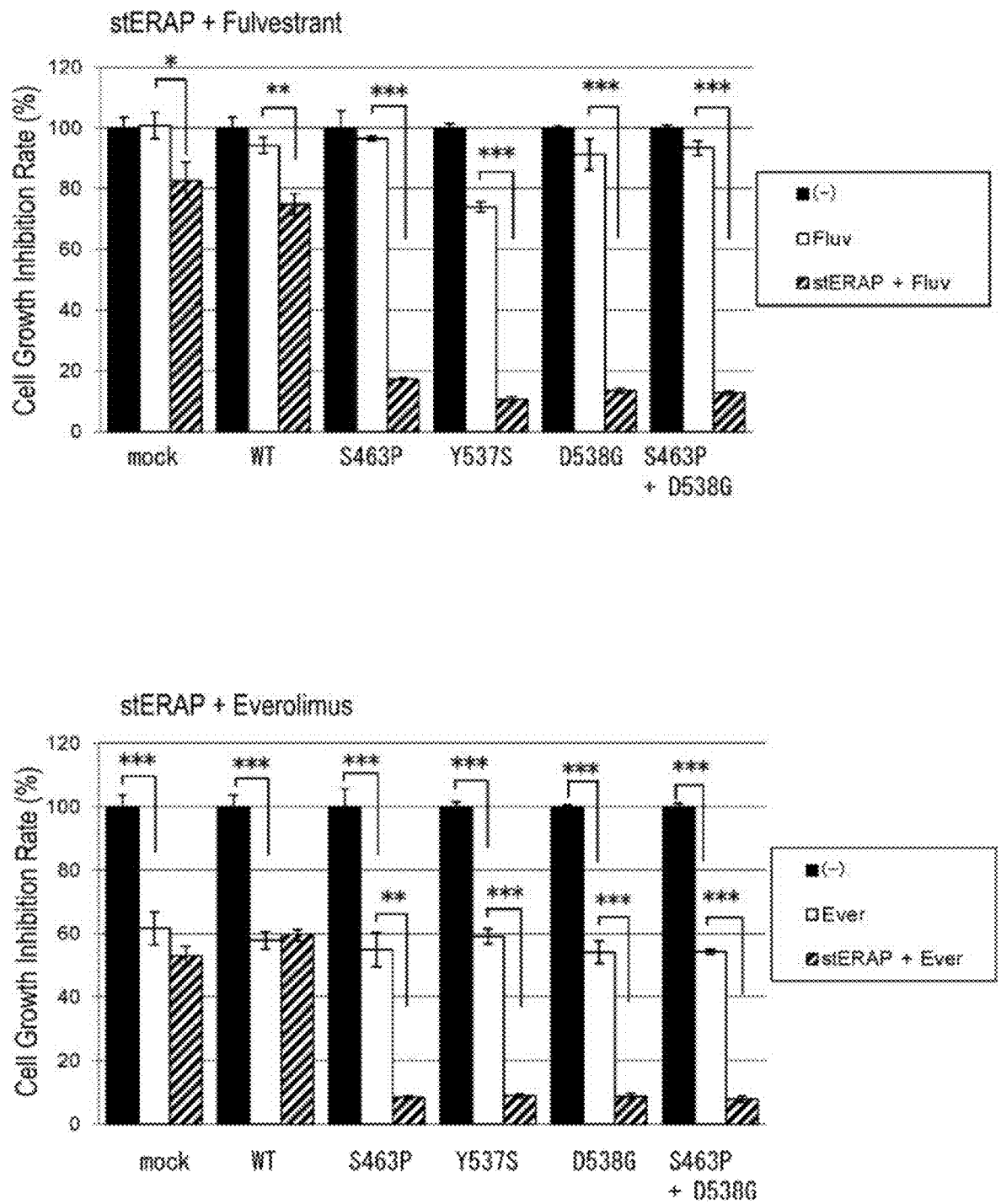

FIG. 11 shows the inhibitory effects by combined use of stERAP and an anti-estrogen agent against the growth of MCF-7 cells transfected with an ESR1 mutant. MCF-7 cells transfected with each ESR1 mutant were reacted for 96 hours with 10 µM stERAP and 1 µM of tamoxifen (TAM) and 2 µM of fulvestrant (Fluv) which are anti-estrogen agents and 0.5 µM of everolimus (Ever) which is an mTOR inhibitor. Then, the cell growth was evaluated. Data represent the mean±standard error of three independent experiments (*P<0.05, P<0.01, and *P<0.01).

Figure 12:
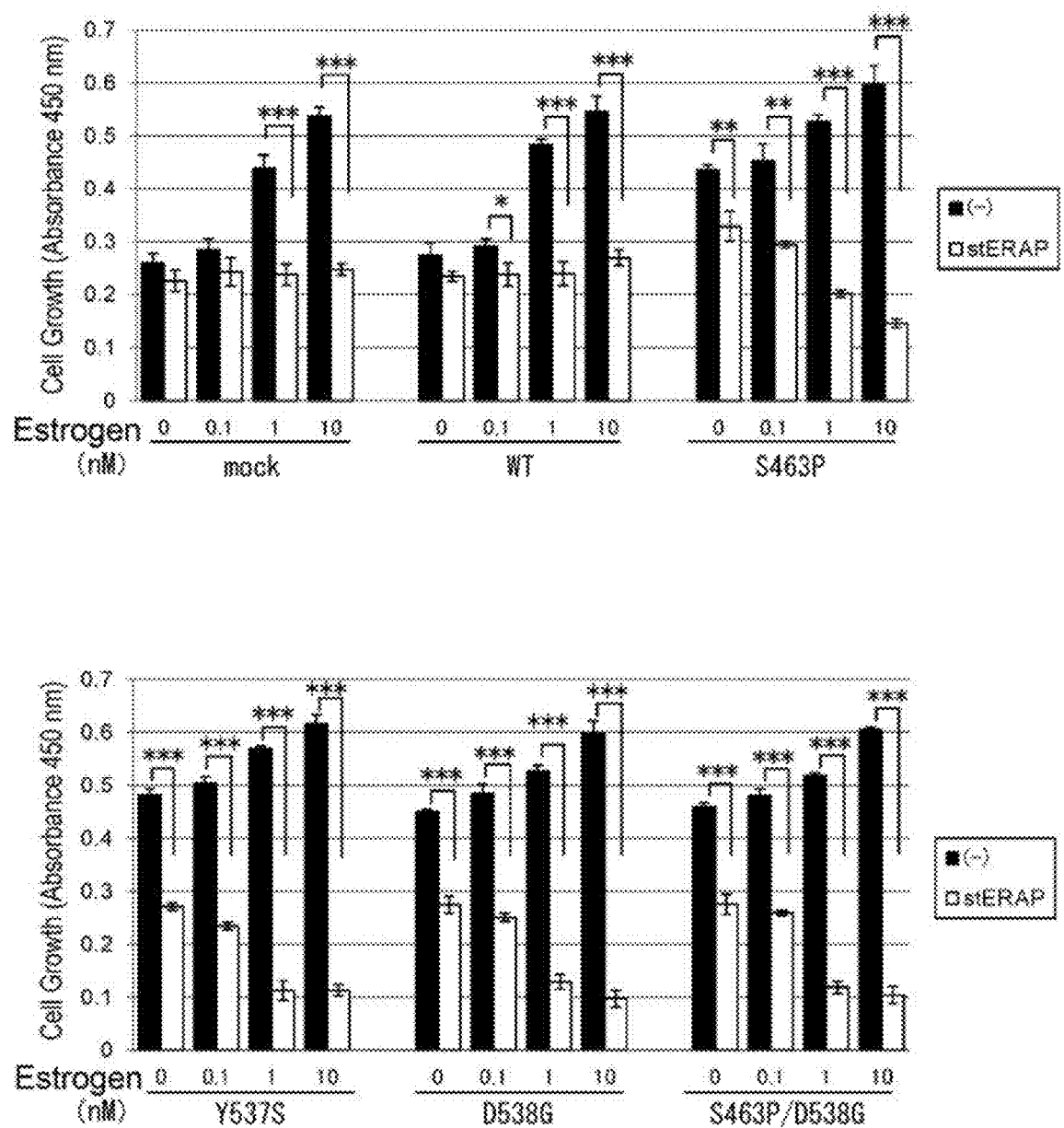

FIG. 12 shows the inhibitory effects of stERAP on growth of MCF-7 cells transfected with an ESR1 mutant in the presence of estrogen. MCF-7 cells transfected with each ESR1 mutant were reacted for 24 hours with 10 µM stERAP in the presence of estrogen at various concentrations (0.1 nM, 1 nM, or 10 nM), and the cell growth was evaluated. Data represent the mean±standard error of three independent experiments (*P<0.05, P<0.01, and *P<0.001).

Figure 13:
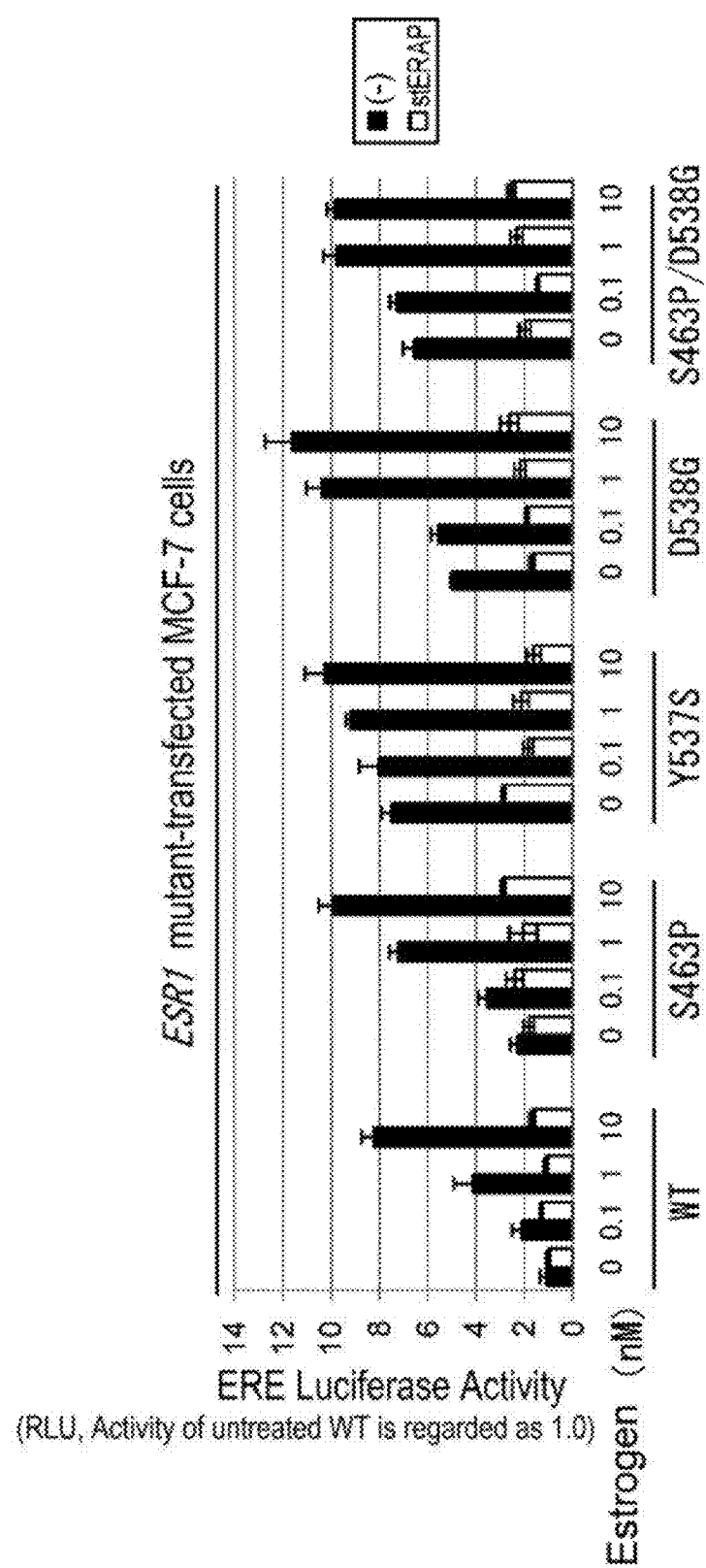

FIG. 13 shows the inhibitory effects of stERAP on ERα transcriptional activity in the presence of estrogen in MCF-7 cells transfected with an ESR1 mutant. MCF-7 cells transfected with each ESR1 mutant were reacted for 24 hours with 10 µM stERAP in the presence of estrogen at various concentrations (0.1 nM, 1 nM, or 10 nM), and ERE-luciferase activities (ERα transcription activities) were measured. Data represent the mean±standard error of three independent experiments.

Figure 14:
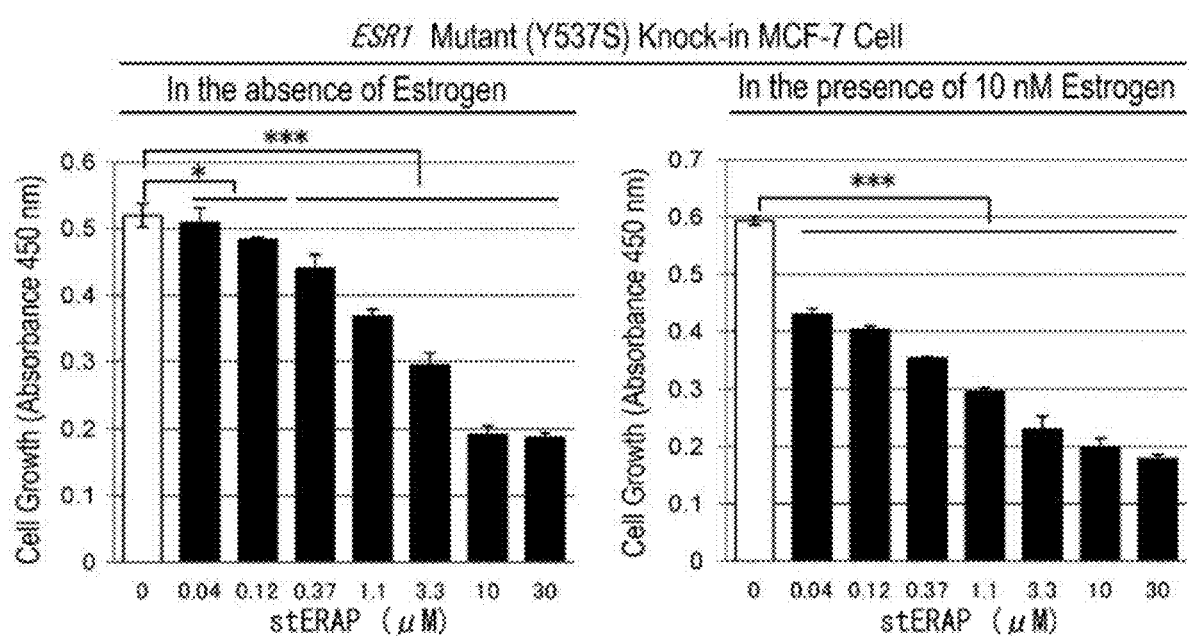

In FIG. 14, cell growth was evaluated for ESR1 Y537S knocked-in MCF-7 cells, when the cells were reacted for 24 hours with stERAP alone at various concentrations shown in the drawing (horizontal axis) and in the presence of 10 nM estrogen. Data represent the mean±standard error of three independent experiments.

FIG. 15 shows that BIG3 in a HER2-positive breast cancer cell line functions as AKAP. (A) The expression of BIG3 in a HER2-positive breast cancer cell line is shown. The mRNA levels of BIG3 in a luminal type breast cancer cell line (MCF-7 cells), HER2-positive breast cancer cell lines (BT-474 cells, SK-BR-3 cells, and KPL-4 cells), and a normal mammary gland cell line (MCP-10A cells) were determined by real-time PCR. Data were normalized by the β2-MG content and expressed as multiples (-fold) of the value in MCF-10A cells, with that value being defined as 1.0. Data represent the mean±standard error of three independent experiments. (B) Immunoblots are shown which indicate that BIG3 binds with PKA, PP1Cα, and PHB2. SK-BR-3 cells and KPL-4 cells were lysed, the cell lysates were immunoprecipitated using an anti-BIG3 antibody and a rat IgG antibody, and immunoblot analyses were performed using the antibodies shown in the drawing. Data shown are representatives from three independent experiments. (C) The kinase activity and phosphatase activity of BIG3 are shown. SK-BR-3 cells were treated for 24 hours with 10 μM H-89, 100 μg/mL trastuzumab, and 10 nM lapatinib, cell lysates thereof were subjected to immunoprecipitation using an anti-BIG3 antibody, and their PKA activity and PP1Cα activity were calculated using CREBtide and p-NPB as substrates. SK-BR3 call lysate was subjected to immunoprecipitation using a rat anti-IgG antibody, and this was used as a negative control. Data represent the mean±SE of three independent experiments (***P<0.001).

Figure 16:
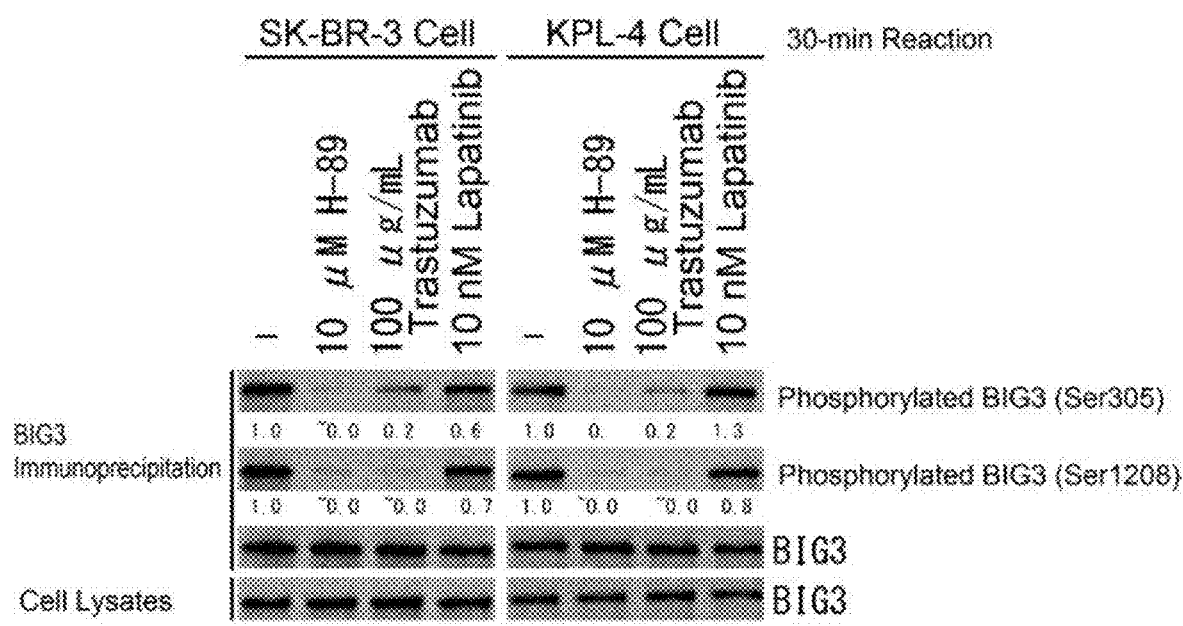

FIG. 16 shows the mechanism for activation of BIG3 in a HER2-positive breast cancer cell line. Immunoblots are shown which indicate that BIG3 is phosphorylated by PKA through HER2 signaling. SK-BR-3 cells and KPL-4 cells were treated for 30 minutes with 10 μM H-89, 100 μg/mL trastuzumab, and 10 nM lapatinib, cell lysates thereof were subjected to immunoprecipitation using an anti-BIG3 antibody, and immunoblot analyses were performed using the antibodies shown in the drawing.

FIG. 17 shows that BIG3 controls the suppressive activity of PHB2 in a HER2-positive breast cancer cell line. (A) Immunoblots are shown which indicate that BIG3 binds to PHB2 and controls its phosphorylation. SK-BR-3 cells and KPL-4 cells were treated for 24 hours with 1 μM stERAP, cell lysates thereof were subjected to immunoprecipitation using an anti-BIG3 antibody and an anti-PHB2 antibody, and immunoblot analyses were performed using the antibodies shown in the drawing. (B) Immunoblots are shown which indicate that PHB2 is phosphorylated via EGFR signaling at Ser39. After suppressing PKA expression by the siRNA method, SK-BR-3 cells were treated for 24 hours with 1 μM stERAP and SK-BR-3 cells were treated with 100 μg/mL trastuzumab and 10 nM lapatinib in the presence of 1 μM stERAP. Cells were lysed respectively and were immunoprecipitated using an anti-PHB2 antibody, and immunoblot analyses were performed using the antibodies shown in the drawing.

FIG. 18 shows PKCα-dependent phosphorylation of PHB2 (Ser39). (A) Immunoblots are shown which indicate that PHB2 (Ser39) is phosphorylated in a PKCα-dependent manner in a HER2-positive breast cancer cell line. SK-BR-3 cells in which PKCα expression was suppressed by the siRNA method were treated for 24 hours with 1 μM stERAP, then cell lysate thereof was subjected to immunoprecipitation using an anti-PHB2 antibody, and immunoblot analyses were performed using the antibodies shown in the drawing. (B) PKCα activity by EGFR signaling in SK-BR-3 cells is shown. SK-BR-3 cells were treated for 24 hours with 1 μM stERAP, and with 10 nM lapatinib in the presence of stERAP, cell lysates thereof were subjected to immunoprecipitation using an anti-PKCα antibody, and PKCα activities were calculated using CREBtide as a substrate. Data represent the mean±standard error of three independent experiments.

Figure 19A:
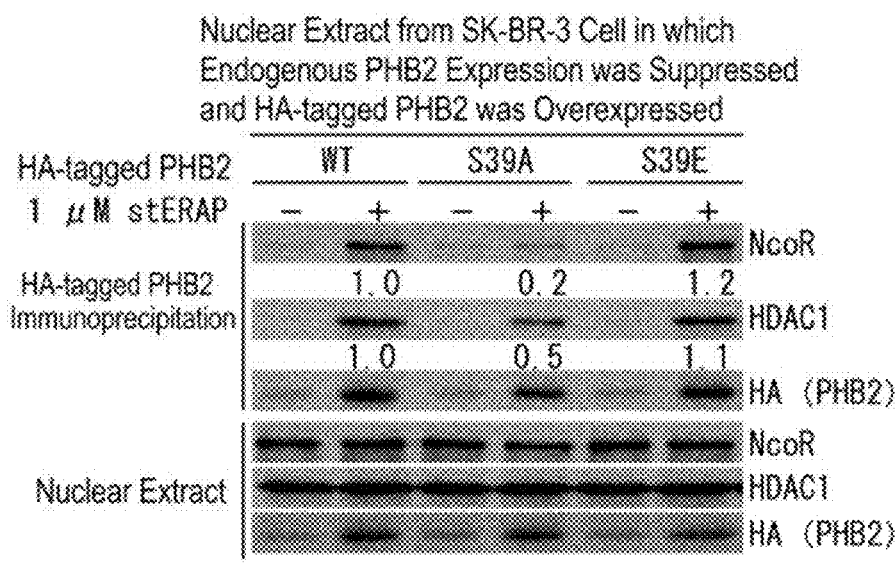

FIG. 19 shows that phosphorylated PHB2 (Ser39) suppresses transcriptional activity in the nucleus. (A) Immunoblots are shown which indicate that transcriptional repressors NcoR and HDAC1 bind to phosphorylated PHB2 (Ser39). SK-BR-3 cells in which PHB2 expression was suppressed by the siRNA method were transfected with the HA-tagged PHB2 construct (WT), the alanine mutant at Ser39 (S39A), and the glutamic acid mutant at Ser39 (S39E), and 48 hours later, these were treated for 24 hours with 1 μM stERAP. The nuclear fractions were isolated by specific gravity centrifugation, then the nuclear extract solutions were subjected to immunoprecipitation using an anti-HA antibody, and immunoblot analyses were performed using the antibodies shown in the drawing. (B) Immunoblots are shown which indicate that phosphorylation of PHB2 (Ser39) could not suppress HER2 signaling. SK-BR-3 cells were treated for 24 hours with 100 μg/mL trastuzumab and 10 nM lapatinib in the presence of 1 μM stERAP, cell lysates thereof were subjected to immunoprecipitation using an anti-HER2 antibody, and immunoblot analyses were performed using the antibodies shown in the drawing.

Figure 20A:
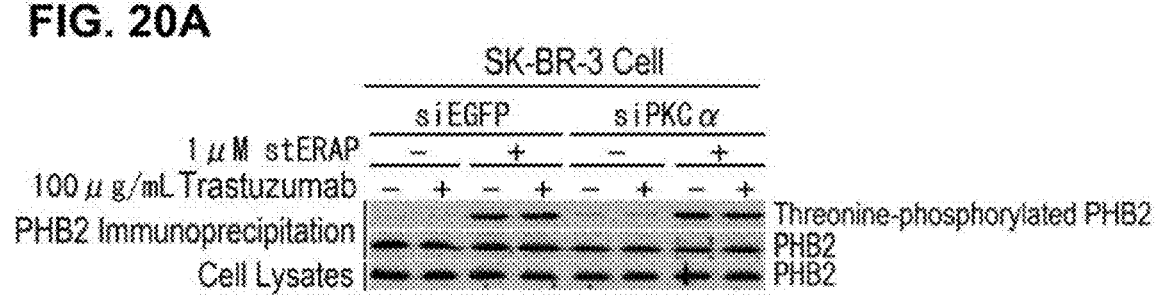

FIG. 20 shows the threonine phosphorylation in PHB2 and activation mechanism therefor. (A) Immunoblots are shown which indicate that threonine phosphorylation of PHB2 is induced PKCα-independently in a HER2-positive breast cancer cell line. SK-BR-3 cells in which PKCα expression was suppressed by the siRNA method were treated for 24 hours with 1 μM stERAP and 100 μg/mL trastuzumab, then cell lysates thereof were subjected to immunoprecipitation using an anti-PHB2 antibody, and immunoblot analyses were performed using the antibodies shown in the drawing. (B) Immunoblots are shown which indicate that PHB2 is threonine phosphorylated by TTK and MK5. SK-BR-3 cells in which TTK, CHK1, and MK5 expressions were suppressed by the siRNA method were treated for 24 hours with 1 μM stERAP, then the cells were lysed and subjected to immunoblot analyses using the antibodies shown in the drawing.

FIG. 21 shows the effects of threonine phosphorylation of PHB2 caused by TTK and MK5, on the HER2 signal. (A, B) Immunoblots are shown which indicate that threonine phosphorylation of PHB2 caused by TTK and MK5 inhibits the HER2-HER3 binding and HER2-Shc binding. SK-BR-3 cells (A) and KPL-4 cells (B) in which TTK, MK5, and CHK1 expressions were suppressed by the siRNA method were treated for 24 hours with 1 μM stERAP, then the cells were lysed and subjected to immunoprecipitation using an anti-HER2 antibody, and immunoblot analyses were performed using the antibodies shown in the drawing. (C) Immunoblots are shown which indicate that inhibition of HER2-HER3 binding and HER2-Shc binding by PHB2 is avoided by a TTK inhibitor. SK-BR-3 cells were treated for 24 hours with 2 μM AZ3146 and 1 μM stERAP, and then cell lysates thereof were subjected to immunoprecipitation using an anti-HER2 antibody, and immunoblot analyses were performed using the antibodies shown in the drawing.

Figure 22A:
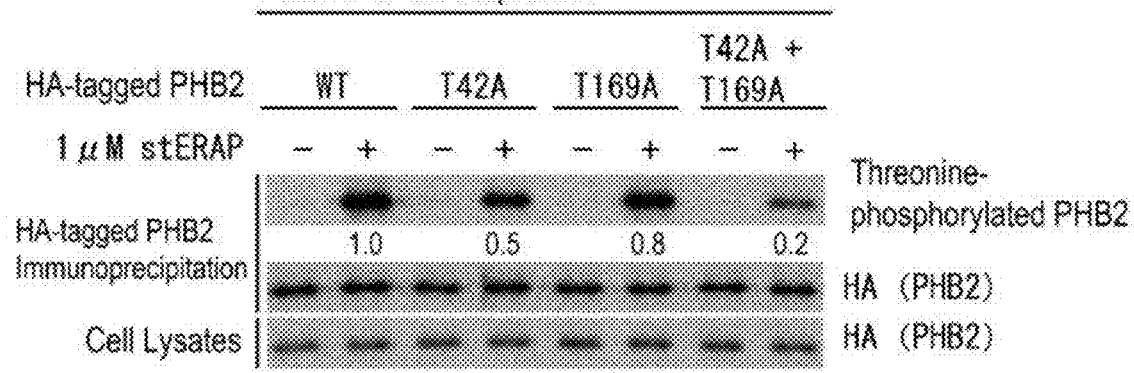
Figure 22B:
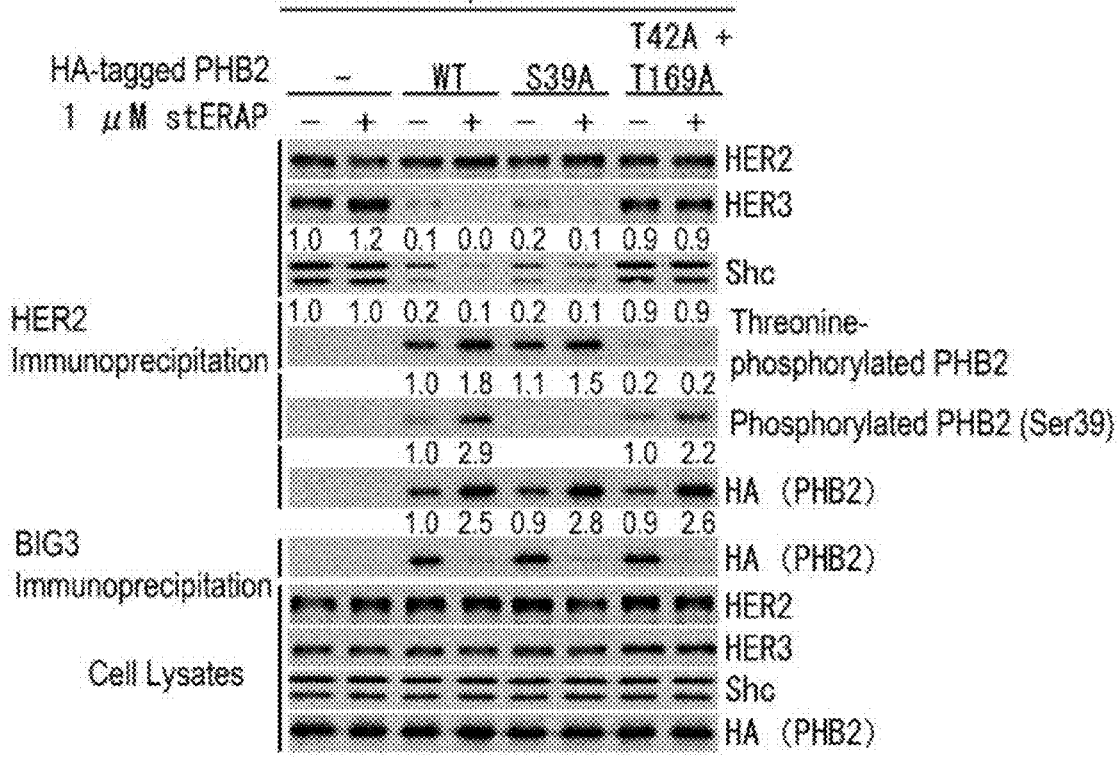

FIGS. 22A-B show identification of the threonine phosphorylation sites in PHB2. (FIG. 22A) Immunoblots are shown which evaluate Thr42 and Thr169 as the threonine phosphorylation sites in PHB2. SK-BR-3 cells in which PHB2 expression was suppressed by the siRNA method were transfected with the HA-tagged PHB2 construct, alanine mutant at Thr42 (T42A), alanine mutant at Thr169 (T169A), and double alanine mutant at Thr42 and Thr169 (T42A+T169A). 48 hours later, these were treated for 24 hours with 1 μM stERAP. The cells were then lysed and subjected to immunoprecipitation using an anti-HA antibody, and immunoblot analyses were performed using the antibodies shown in the drawing. (FIG. 22B) Immunoblots are shown which indicate that phosphorylation of Thr42 and Thr169 in PHB2 inhibits HER2-HER3 binding and HER2-Shc binding. SK-BR-3 cells in which PHB2 expression was suppressed by the siRNA method were transfected with the HA-tagged PHB2 construct, alanine mutant at Thr42, (T42A) alanine mutant at Thr169 (T169A) and double alanine mutant at Thr42 and Thr169 (T42A+T169A). 48 hours later, these were treated for 24 hours with 1 μM stERAP. The cells were then lysed and subjected to immunoprecipitation using an anti-HER2 antibody and an anti-BIG3 antibody, and immunoblot analyses were performed using the antibodies shown in the drawing.

Figure 23A:
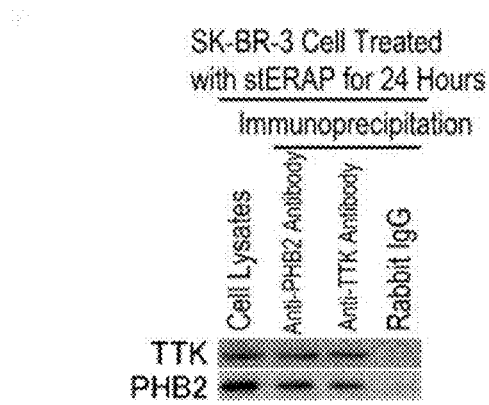

FIG. 23 shows threonine phosphorylation of PHB2 caused by TTK and MK5. (A) Immunoblots are shown which indicate that PHB2 binds to TTK. SK-BR-3 cells were treated for 24 hours with 1 μM stERAP, then the cells were lysed and subjected to immunoprecipitation using an anti-PHB2 antibody, an anti-TTK antibody, and a rabbit IgG antibody, and immunoblot analyses were performed using the antibodies shown in the drawing. (B, C) Immunoblots are shown which used Phos-tag to evaluate threonine phosphorylation of PHB2 by TTK and MK5. Recombinant TTK (B) and recombinant MK5 (C) were reacted with recombinant PHB2 at varied molar ratios with respect to PHB2 at 30° C. for 30 minutes in the presence of ATP. Thereafter, immunoblot analyses by Phos-tag were performed using the antibodies shown in the drawing.

FIG. 24 shows the suppressive effects of stERAP on the growth of HER2-positive breast cancer cell lines. The results of MTT assays evaluating the inhibitory effects of stERAP on the growth of HER2-positive breast cancer cell lines are shown. SK-BR-3 cells, BT-474 cells, and KPL-4 cells were reacted with stERAP for 24 hours. Data represent the mean±SE of three independent experiments (*P<0.05, P<0.01, and *P<0.001).

Figure 25:
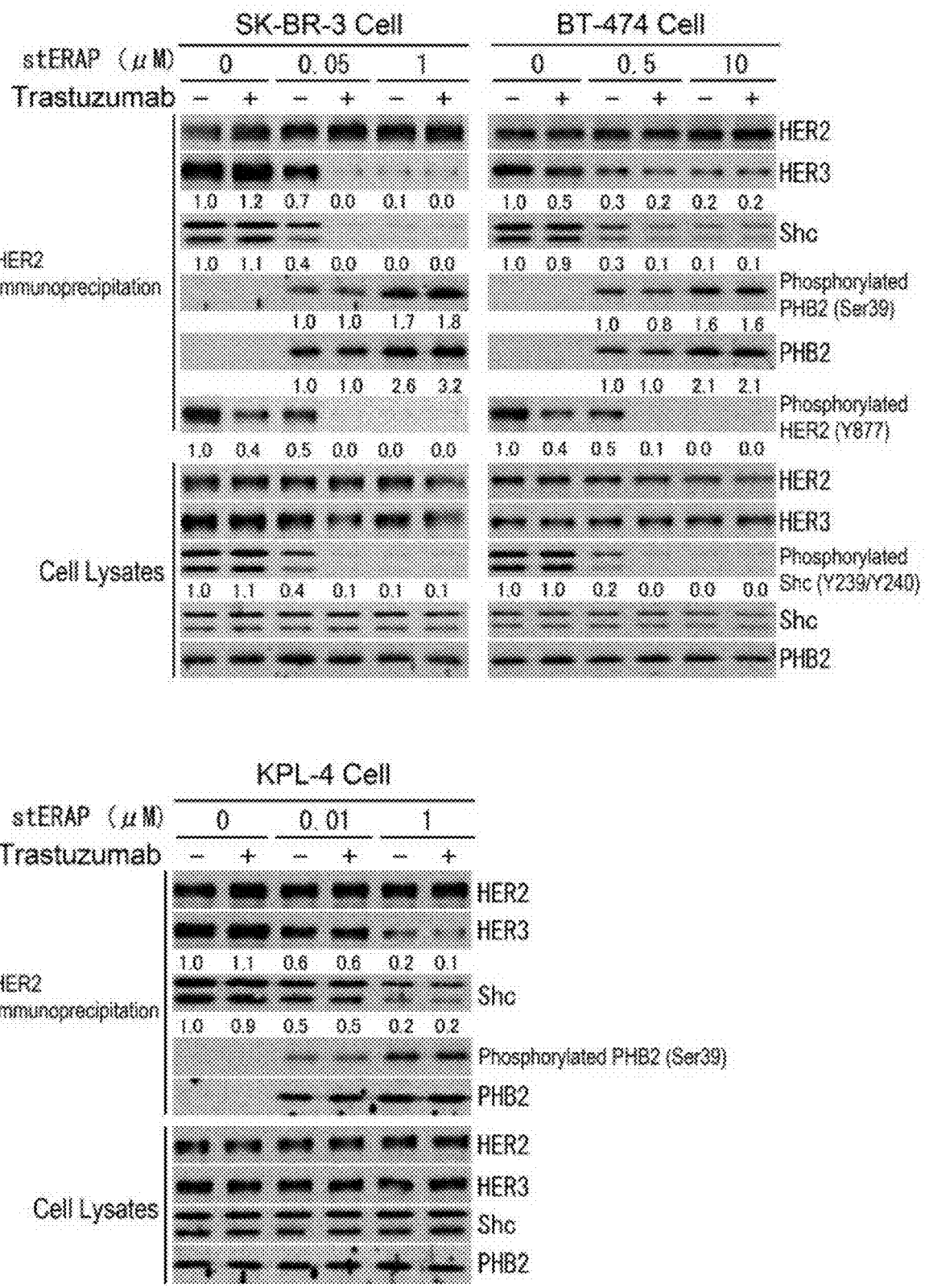

FIG. 25 shows that stERAP inhibits HER2-HER3 interaction and HER2-Shc interaction. Immunoblots are shown which indicate that stERAP inhibits HER2-HER3 interaction and HER2-Shc interaction in HER2-positive breast cancer cell lines. HER2-positive breast cancer cell lines (SK-BR-3 cells, BT-474 cells, and KPL-4 cells) were treated for 24 hours with stERAP at various concentrations and 100 μg/mL trastuzumab, then cell lysates thereof were subjected to immunoprecipitation using an anti-HER2 antibody, and immunoblot analyses were performed using the antibodies shown in the drawing.

Figure 26A:
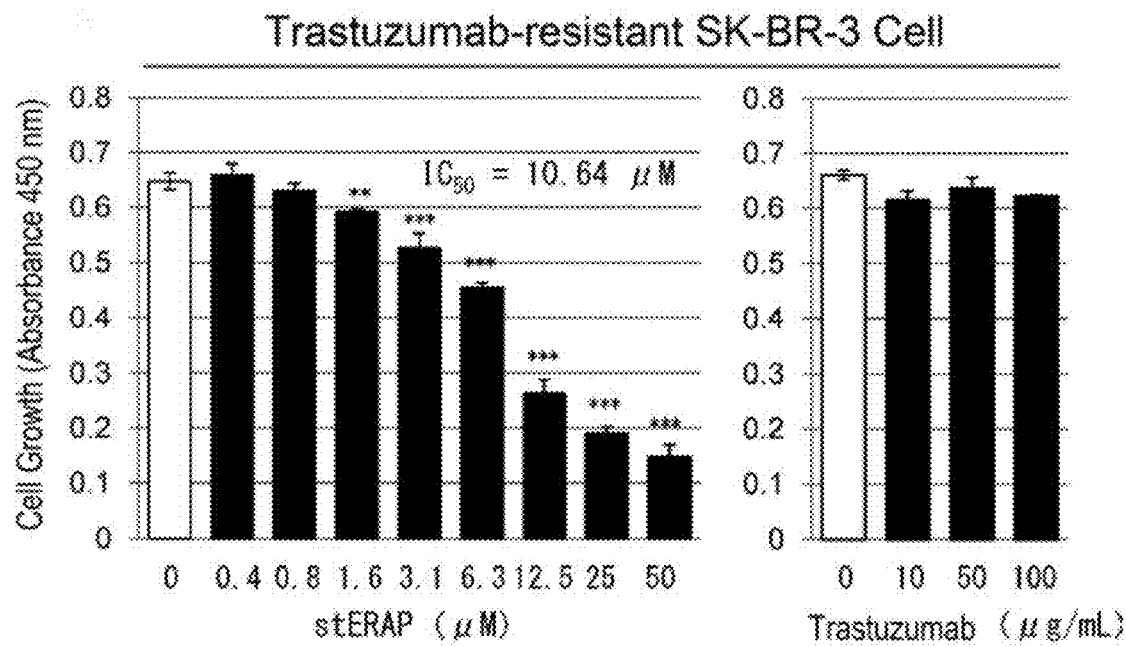

FIG. 26 shows the suppressive effects of stERAP on trastuzumab-resistant HER2-positive breast cancer cell lines. (A) The results of MTT assays are shown, which evaluated the inhibitory effects of stERAP on the growth of trastuzumab-resistant HER2-positive breast cancer cell lines. Trastuzumab-resistant SK-BR-3 cells were reacted for 24 hours with stERAP and trastuzumab. Data represent the mean±SE of three independent experiments (*P<0.05, P<0.01, and *P<0.001). (B) immunoblots are shown which indicate that stERAP inhibits HER2-HER3 interaction and HER2-Shc interaction in a trastuzumab-resistant HER2-positive breast cancer cell line. SK-BR-3 cells and trastuzumab-resistant SK-BR-3 cells were treated for 24 hours with 20 μM stERAP and 100 μg/mL trastuzumab, then cell lysates thereof were subjected to immunoprecipitation using an anti-HER2 antibody, and immunoblot analyses were performed using the antibodies shown in the drawing.

Figure 27:
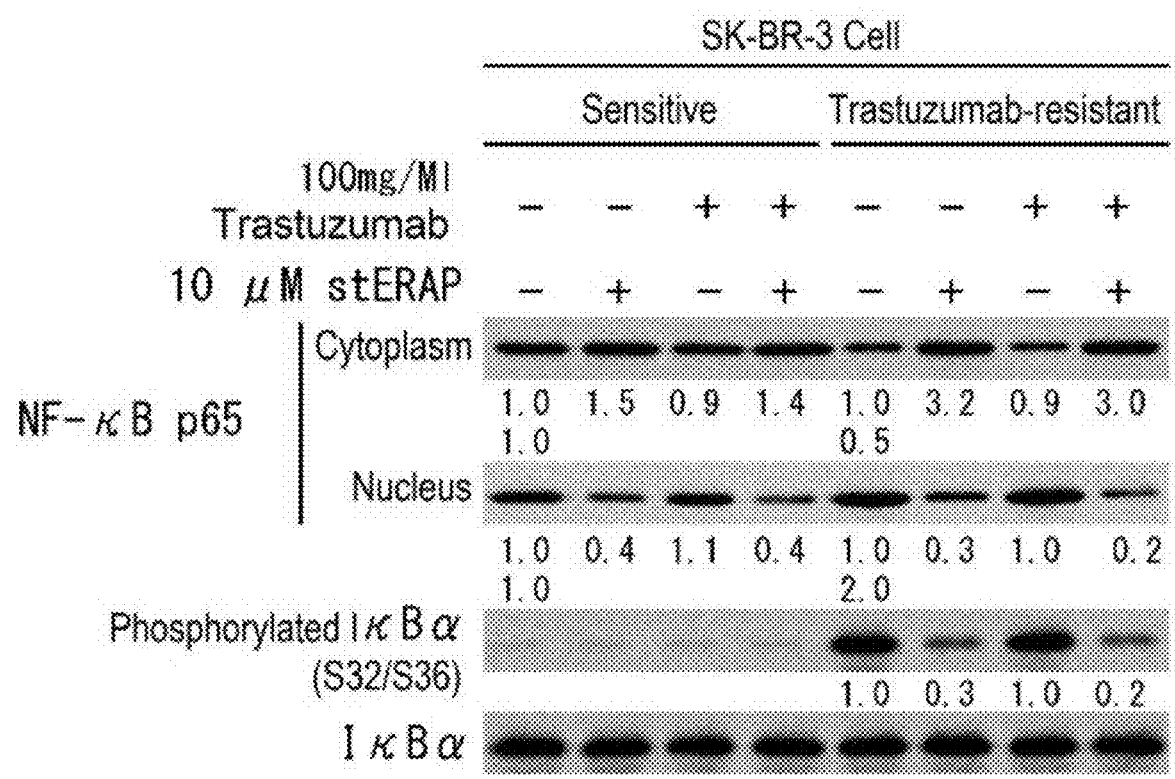

FIG. 27 shows the effects of stERAP on NF-κB signal in trastuzumab-resistant HER2-positive breast cancer cell lines. Immunoblots are shown which indicate that stERAP suppresses nuclear translocation of NF-κB and phosphorylation of IκBα in a trastuzumab-resistant HER2-positive breast cancer cell line. SK-BR-3 cells and trastuzumab-resistant SK-BR-3 cells were treated for 24 hours with 20 μM stERAP and 100 μg/mL trastuzumab, then the cells were lysed, and immunoblot analyses were performed using the antibodies shown in the drawing.

Figure 28:
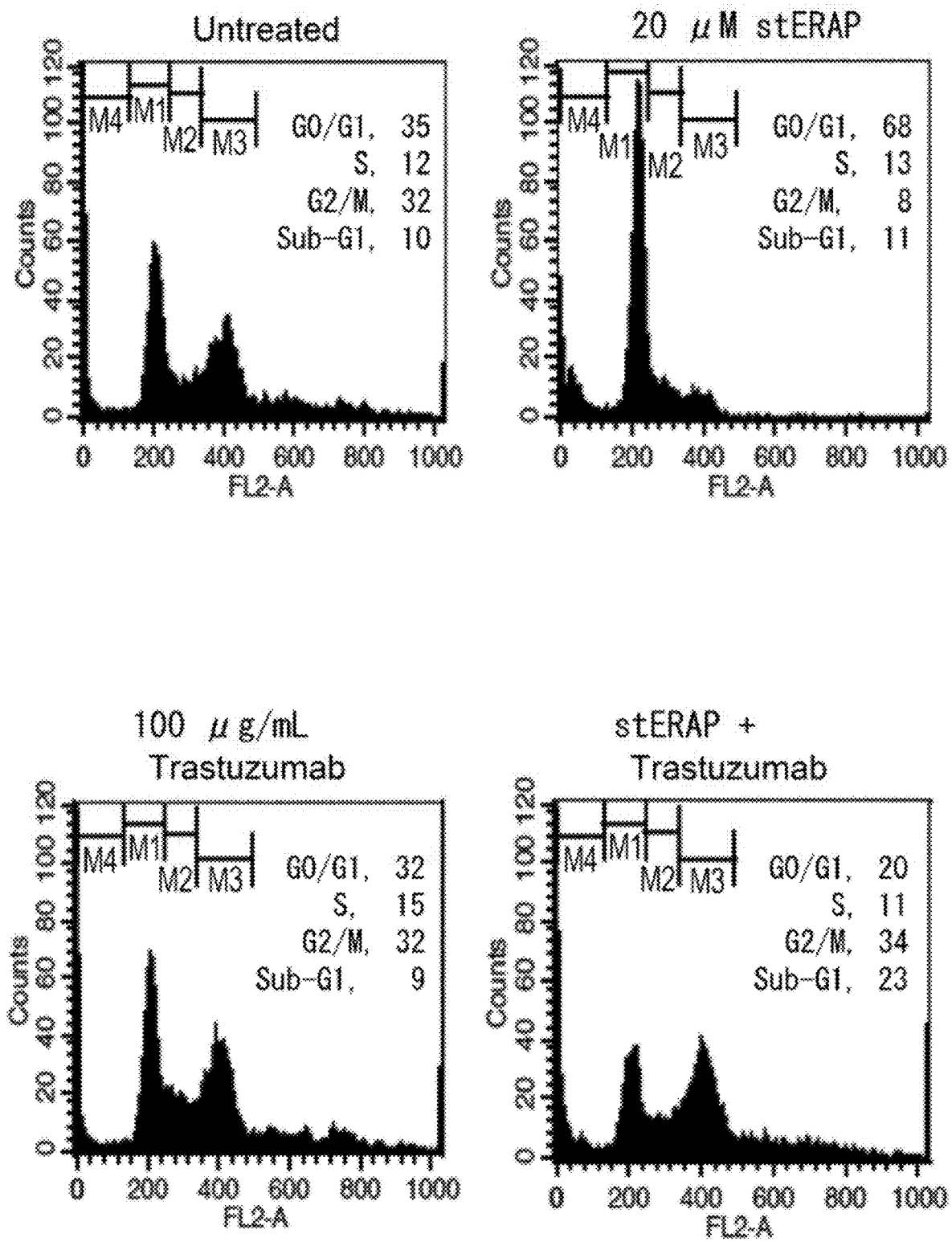

FIG. 28 shows the effects of stERAP on the cell cycle of trastuzumab-resistant HER2-positive breast cancer cell lines. FACS analyses showing the effects of stERAP on the cell cycle are shown. Trastuzumab-resistant SK-BR-3 cells were treated for 24 hours with 20 μM stERAP and 100 μg/mL trastuzumab then the cells were fixed, stained by propidium iodide, and analyzed by flow cytometry.

Figure 29:
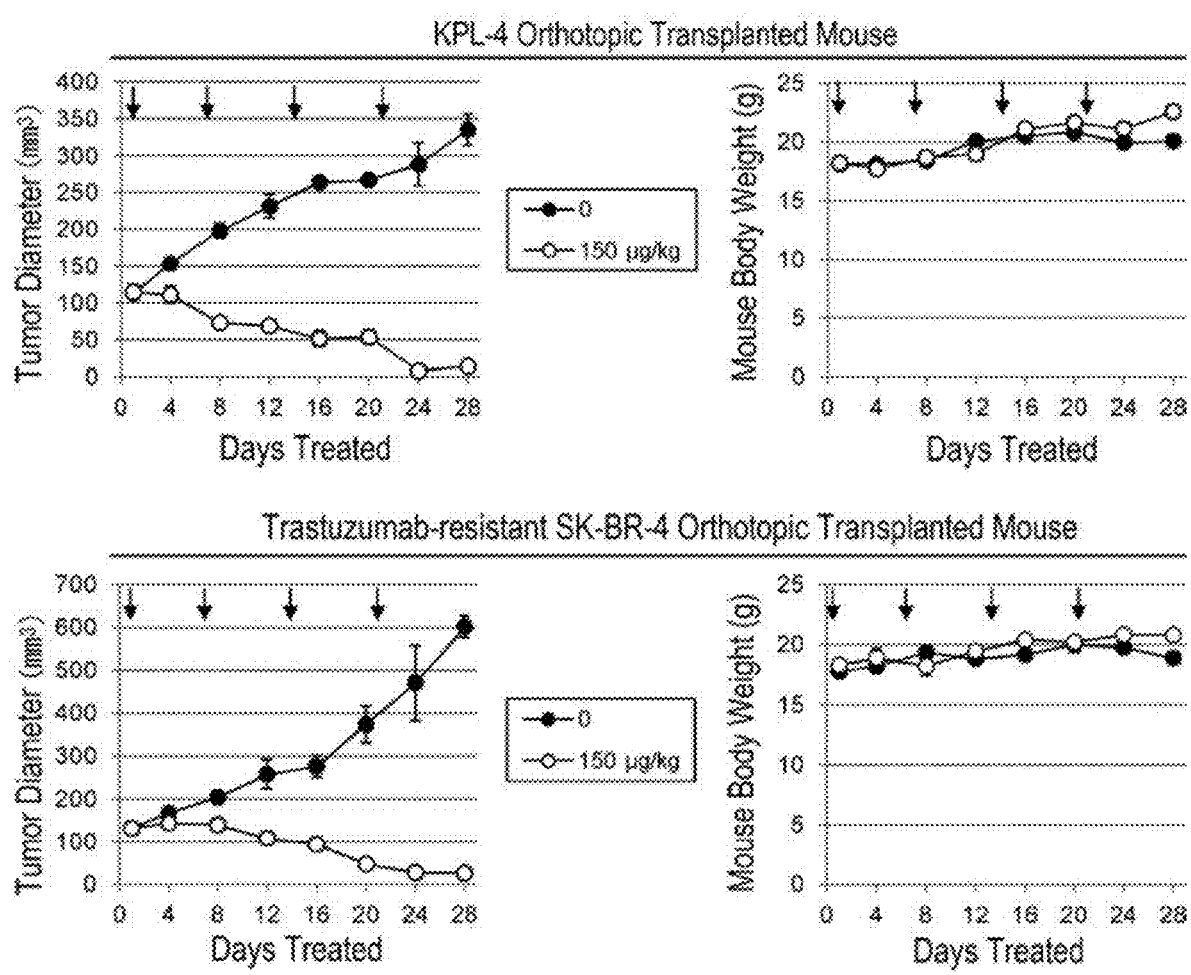

FIG. 29 shows the in vivo antitumor effects of stERAP on trastuzumab-resistant HER2-positive breast cancer cells. The inhibitory effects of stERAP on tumor growth in mouse models subjected to orthotopic transplantation of KPL-4 cells and trastuzumab-resistant SK-BR-3 cells are shown. The left panel shows the change in tumor diameter in the group receiving administration of 150 μg/kg of stERAP every seven days, and the right panel shows the change in mouse body weight. Each symbol in each graph indicates the following: filled circle: untreated; and open circle: 150 μg/kg stERAP. Data on tumor diameter and body weight represent the mean±standard error of each group (n=5, ***P<0.001).

Figure 30:
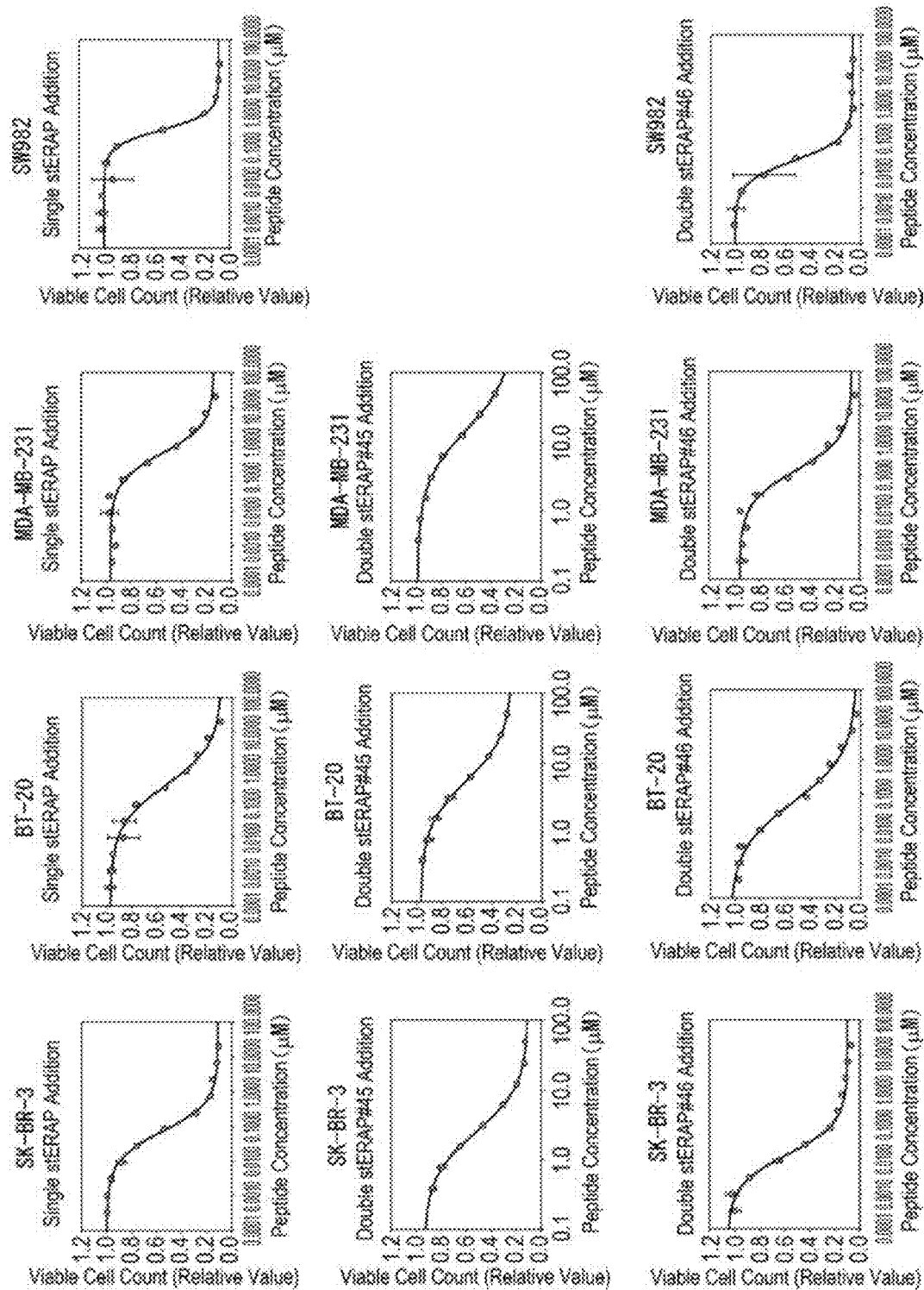

FIG. 30 shows the results of investigating the effects of three types of stERAP (single stERAP, double stERAP #45, and double stERAP #46) on cell growth of three types of breast cancer cell lines (SK-BR-3, BT-20, and MDA-MB-231) and synovial sarcoma cell line SW982. For the single stERAP and double stERAP #46, peptides were added at a total of eleven concentrations prepared by three-fold serial dilution starting from 20 μM. For the double stERAP #45, peptides were added at a total of eight concentrations prepared by two-fold serial dilation starting from 50 μM. The number of viable cells were measured 96 hours after the peptide addition, and relative values thereof were calculated based on the negative control cells without peptide addition and plotted. Experiments using double stERAP #45 on the SW982 cell line were not carried out.

Figure 31A:
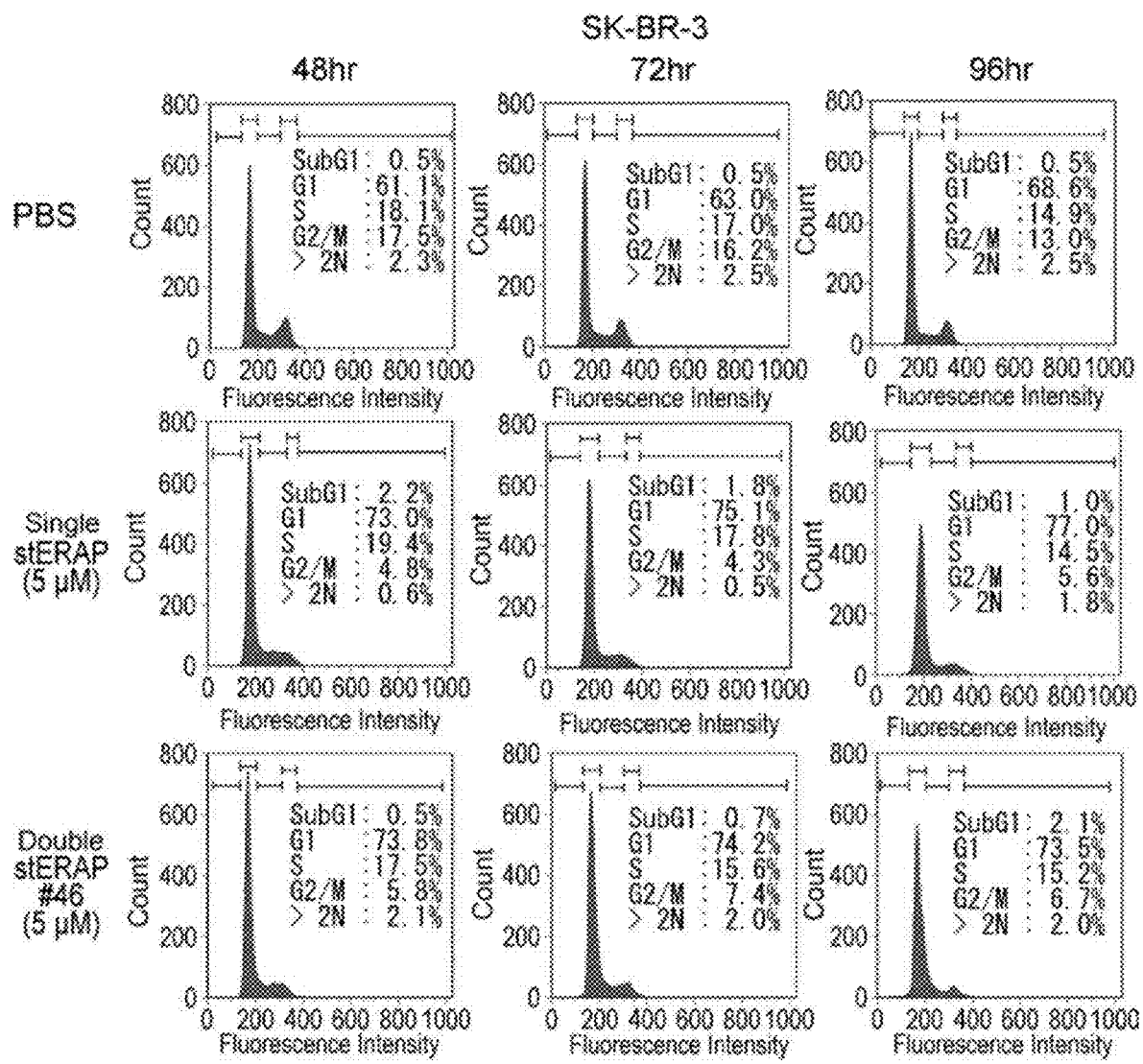
Figure 31B:
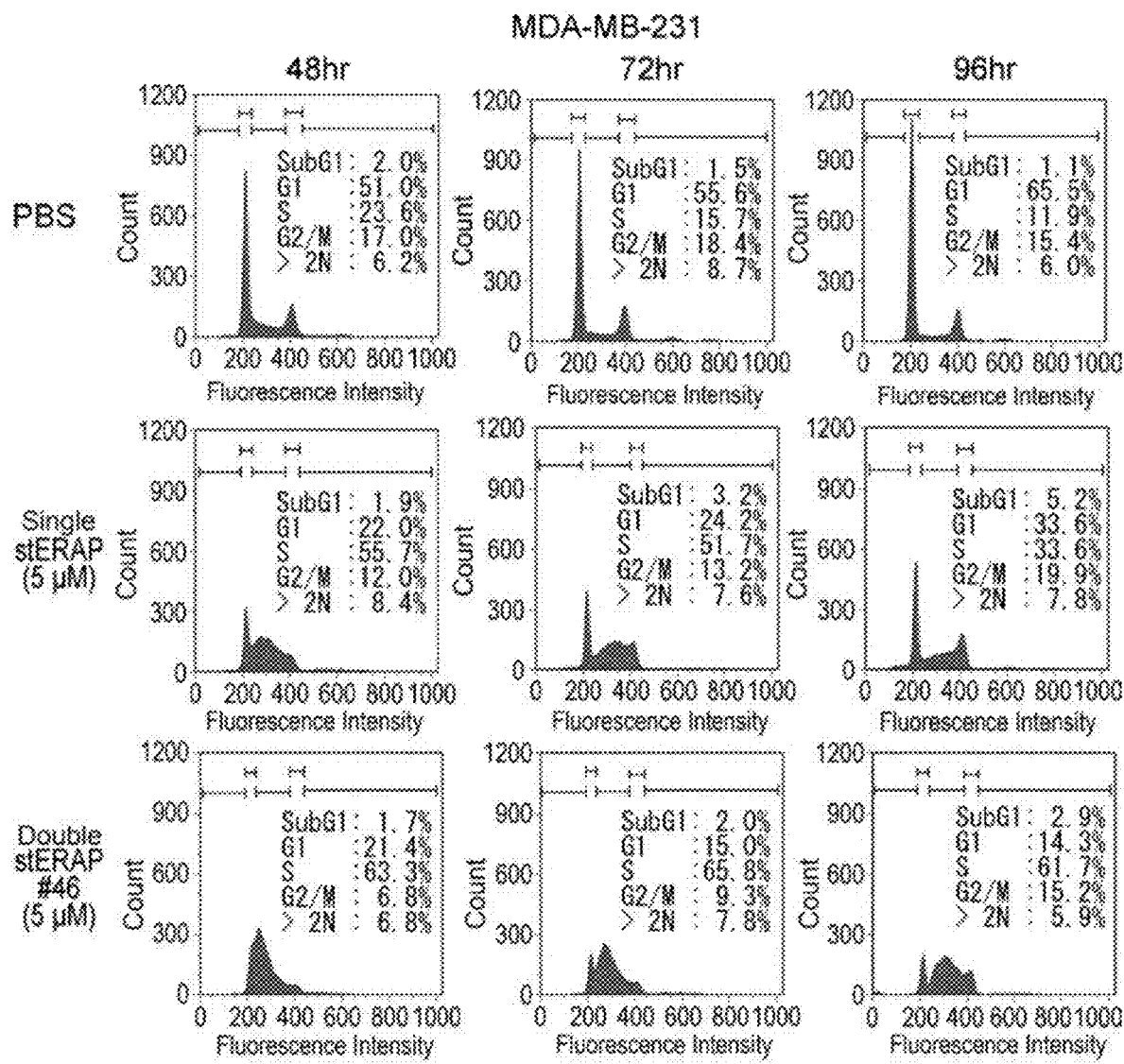

FIGS. 31A-B show the results of investigating the effects of two types of stERAPs (single stERAP and double stERAP #46) on the cell cycle of SK-BR-3 cells (FIG. 31A) and MDA-MB-231 cells (FIG. 31B). Each peptide was added at 5 μM concentration. 96 hours later, the cells were stained with Propidium Iodide (PI). Fluorescence intensity of each cell was measured using a flow-cytometer and histograms were prepared. In the graphs, the percentages of the number of cells at each phase of the cell cycle (Sub G1 phase, G1 phase, S phase, and G2/M phase; >2 N cells) are shown.

DESCRIPTION OF EMBODIMENTS

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Definitions

The words "a", "an", and "the" used herein mean "at least one" unless otherwise specifically indicated.

Herein, unless otherwise specifically indicated, amino acids represented by capital letters indicate L-amino acids. Amino acids represented by lower-case letters indicate D-amino acids. Furthermore, L-amino acids and D-amino acids represented herein may include amino acids in which any of amino group, carboxyl group, and side chains has been modified. Examples of preferred modifications include acetylation of the amino group, amidation of the carboxyl group, tag peptide addition such as FLAG-tagging and HA-tagging, and such.

Herein, numbers indicating the positions of amino acid residues in amino acid sequences have been given with the N-terminal amino acid residue as number 1 and in order toward the C terminus, unless otherwise specifically indicated.

The term "BIG3" used herein refers to brefeldin A-inhibited guanine nucleotide-exchange protein 3. BIG3 forms a complex with PHB2 to inhibit the estrogen-dependent transcriptional activation-suppressing function of PHB2. BIG3 is also referred to as "ARFGEF family member 3 (ARFGEF3)" or "A7322". An example of a representative nucleotide sequence of the human BIG3 gene is shown in SEQ ID NO: 6 (GenBank Accession No. NM_020340.4), and the amino acid sequence encoded by the gene is shown in SEQ ID NO: 7. In the present invention, BIG3 is not limited to that encoded by the aforementioned nucleotide sequence and also encompasses their isoforms and mutants.

The term "PHB2" used herein refers to prohibitin 2. PHB2 binds to estrogen receptors to inhibit estrogen receptor signaling pathways and suppresses estrogen-dependent cell growth. PHB2 is also referred to as "Repressor of Estrogen Activity (REA)". Examples of representative nucleotide sequences of the human PHB2 gene are shown in SEQ ID NO: 8 (GenBank Accession No. NM_001144831.1) and SEQ ID NO: 10 (GenBank Accession No. NM_001267700.1), and the amino acid sequences encoded by the genes are shown in SEQ ID NO: 9 and SEQ ID NO: 11, respectively. In the present invention, PHB2s are not limited to those encoded by the aforementioned nucleotide sequences and also encompass their isoforms and mutants.

The term "PHB2 peptide" used herein refers to a PHB2-derived peptide which inhibits the binding between BIG3 and PHB2. Specifically, it includes the amino acid sequence (YGVRESVFTVE) shown in SEQ ID NO: 17.

The term "estrogen receptor" used herein encompasses both estrogen receptor α (ERα) and estrogen receptor β (ERβ). Estrogen receptors translocate into the nucleus when bound by estrogen, and bind to the enhancer sequence ERE on a DNA to cause transcriptional activation of genes relating to cell growth. This induces estrogen-dependent cell growth. ERα and ERβ are encoded by the ESR1 gene and ESR2 gene, respectively. The nucleotide sequence of a representative human ESR1 gene is shown in SEQ ID NO: 12 (GenBank Accession No. NM_000125.3). Furthermore, the nucleotide sequence of a representative human ESR2 gene is shown in SEQ ID NO: 14 (GenBank Accession No. NM_001437.2). In the present invention, ERα and ERβ are not limited to those encoded by the aforementioned nucleotide sequences and also encompass their isoforms and mutants. In a preferred embodiment of the present invention, the estrogen receptor is ERα.

The term "ERAP" used herein refers to a peptide consisting of the amino acid sequence of SEQ ID NO: 4 or SEQ ID NO: 5. The amino acid sequence of SEQ ID NO: 4 or SEQ ID NO: 5 is a sequence consisting of the 165th to 177th amino acid residues or the 165th to 178th amino acid residues in the amino acid sequence of BIG3 (SEQ ID NO: 7), and contains amino acid residues important for binding with PHB2 (glutamine (Q) at position 165, aspartic acid (D) at position 169, and glutamine (Q) at position 173 in the amino acid sequence of SEQ ID NO: 7). ERAP has an ability to bind to PHB2 and inhibits BIG3 from forming the complex with PHB2 by binding competitively to PHB2.

The term "stapling structure" used herein refers to a structure in which two (a pair of) amino acid residues in an amino acid sequence constituting a peptide are crosslinked. Herein, a peptide in which original amino acid residues are substituted with one or a plurality of stapling structures is referred to as "a stapled peptide". For example, a stapled ERAP (stERAP or stapled ERAP) is a peptide in which at least one pair of amino acid residues in the peptide consisting of the amino acid sequence of SEQ ID NO: 4 or SEQ ID NO: 5 (ERAP) has been substituted with a stapling structure. A short stapled ERAP refers to a peptide in which at least one pair of amino acid residues in a peptide consisting of a partial sequence of the amino acid sequence of SEQ ID NO: 4 or SEQ ID NO: 5 (short ERAP) has been substituted with a stapling structure. Herein, a short stapled ERAP is also written "sh stapled ERAP".

A peptide in which the original amino acid residues are substituted with one stapling structure is referred to as a "single stapled peptide" or a "single crosslinked peptide", and a peptide in which the original amino acid residues are substituted with two stapling structures is referred to as a "double stapled peptide" or a "double crosslinked peptide". For example, a single stapled ERAP (single stERAP, or single stapled ERAP) is a peptide in which one pair of amino acid residues in the peptide consisting of the amino acid sequence of SEQ ID NO: 4 or SEQ ID NO: 5 (ERAP) has been substituted with a stapling structure; and a double stapled ERAP (dsERAP, double stERAP, or double stapled ERAP) is a peptide in which two pairs of amino acid residues in the peptide consisting of the amino acid sequence of SEQ ID NO: 4 or SEQ ID NO: 5 (ERAP) have been substituted with stapling structures.

These stapled peptides can be referred to as peptide derivatives or peptide analogs since a part of their structures has been artificially substituted.

The term "therapy" used herein encompasses alleviation/improvement of at least one symptom caused by a target disease, suppression of progression of the disease, suppression of enlargement of the disease site, and such. For example, "cancer therapy" includes cancer cell growth suppression, suppression of cancer progression, induction of regression/remission of cancer, alleviation/improvement of symptoms accompanying cancer, suppression of cancer metastasis, suppression of postoperative recurrence, and induction of prolonged survival time.

Peptides of the Present Invention

A peptide of the present invention is a peptide comprising an amino acid sequence in which an n pair(s) (n is a natural number) of amino acid residues is substituted with n number of stapling structure(s) in the amino acid sequence of SEQ ID NO: 4 or SEQ ID NO: 5. Here, n is preferably 3 or less, and more preferably 2. Therefore, in the present invention, n pair(s) of amino acid residues normally refer(s) to one to three pairs, or one or two pairs, and preferably two pairs of amino acid residues.

In the peptides of the present invention, the amino acid residues substituted by the stapling structure are not particularly limited; however, since the first amino acid residue (glutamine (Q)), the fifth (aspartic acid (D)), and the ninth (glutamine (Q)) from the N terminus of the amino acid sequence of SEQ ID NO: 4 or SEQ ID NO: 5 are important amino acid residues for binding with PHB2, from the viewpoint of binding affinity for PHB2, they are preferably selected from amino acid residues other than glutamine (Q)

at the first, aspartic acid (D) at the fifth, and glutamine (Q) at the ninth from the N terminus of the amino acid sequence of SEQ ID NO: 4 (QMLSDLTLQLRQR) or SEQ ID NO: 5 (QMLSDLTLQLRQRQ).

For example, of the amino acid residues constituting the peptide, introducing a stapling structure to the leucine residue (L) provides chymotrypsin-resistance. For example, at least two pairs of amino acid residues including at least one L selected from the group consisting of the third, sixth, eighth, and tenth in the amino acid sequence of SEQ ID NO: 4 or 5 are preferred as positions for substitution with stapling structures.

Examples of the amino acid residues substituted by the stapling structure include the following pairs of amino acid residues:

(a) the third (L) and seventh (T) amino acid residues from the N terminus of the amino acid sequence of SEQ ID NO: 4;
(b) the eighth (L) and twelfth (Q) amino acid residues from the N terminus of the amino acid sequence of SEQ ID NO: 4;
(c) the third (L) and seventh (T) amino acid residues from the N terminus of the amino acid sequence of SEQ ID NO: 5; and
(d) the tenth (L) and fourteenth (Q) amino acid residues from the N terminus of the amino acid sequence of SEQ ID NO: 5.

It is particularly preferred that the above-mentioned amino acid residues or (a) and (b), or (c) and (d) are substituted with stapling structures.

In the peptides of the present invention, the stapling structures are not particularly limited. Peptide stapling techniques are known (for example, Blackwell, H. E. et al., Angew. Chem., Int. Ed. 37, 3281-3284 (1994); Aihara, K. et al., Tetrahedron 71, 4183-4191 (2015); and such); therefore, these known stapling techniques can be used to form stapling structures. For example, stapling structures can be formed by synthesizing peptides through solid-phase synthesis or such by incorporating amino acid derivatives carrying a substituent such as an alkenyl group, and then performing an olefin metathesis reaction or an intramolecular amidation reaction between the substituents of the above-mentioned amino acid derivatives. Commercially available amino acid derivatives may be used as amino acid derivatives for forming the stapling structure.

Examples of preferred stapling structures for the peptides of the present invention include structures represented by Formula (I) shown below:

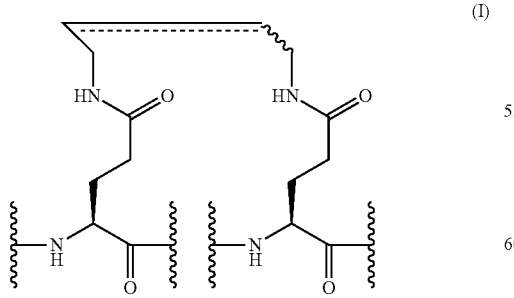

(I)

(wherein the double line drawn by a solid line and a dashed line indicates a single bond or a double bond).

Figure 7:
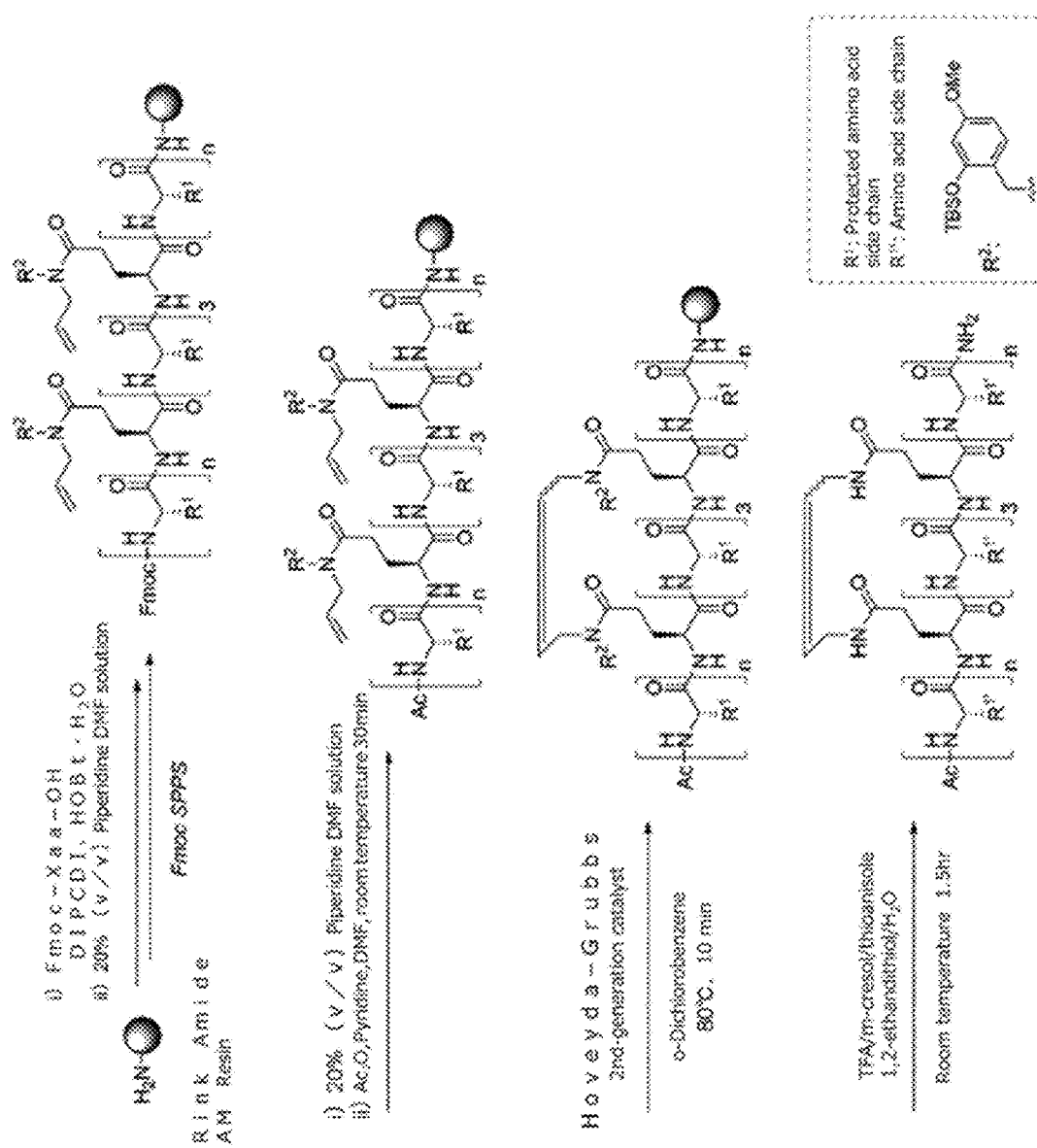

The stapling structure of Formula (I) above can be formed, for example, according to the scheme shown in FIG. 7 (hereinafter, "Scheme (I)"), which is an example where the stapling structure is formed by an olefin metathesis reaction. On the other hand, the scheme shown in FIG. 8 (hereinafter "Scheme (II)") is an example where the stapling structure is formed by an intramolecular amidation reaction.

When thrilling a stapling structure by the olefin metathesis reaction shown in Scheme (I), the amino acid derivative used for stapling may be the glutamine derivative (4-{allyl-[2-(tert-butyl-dimethyl-silanyloxy)-4-methoxy-benzyl]-carbonyl}-2-(9H-fluoren-9-yl-methoxycarbonylamino)-butyric acid) represented by Formula (III) shown below.

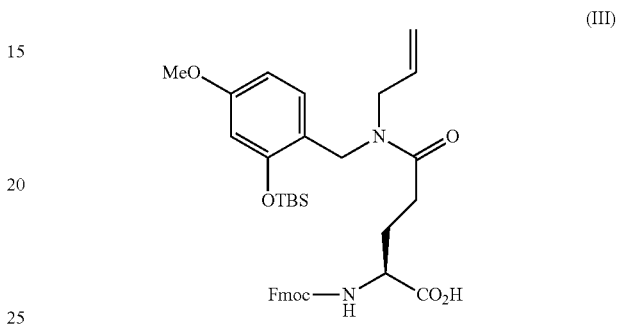

(III)

The glutamine derivative of Formula (III) can be synthesized, for example, according to Scheme (III) shown below (Aihara, K. et al., Tetrahedron 71, 4183-4191 (2015)).

Scheme (III)

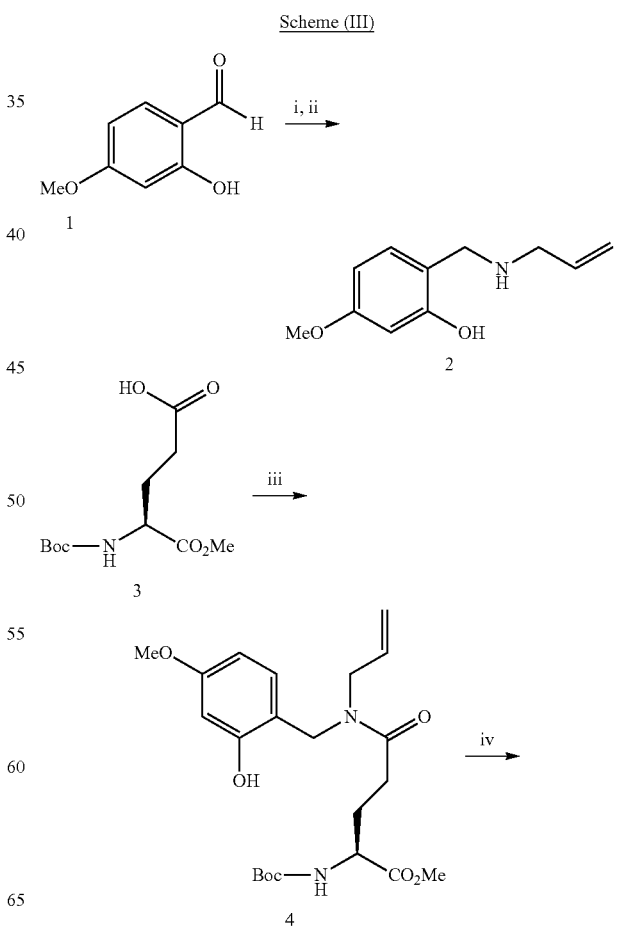

-continued

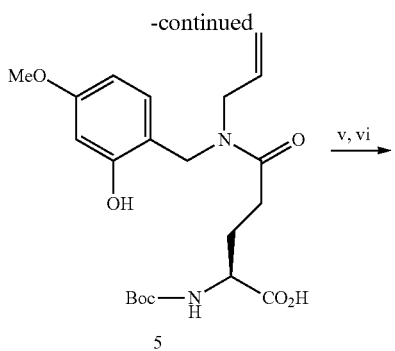

5

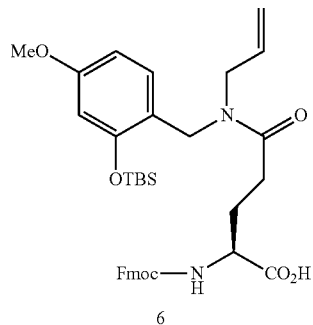

6

In Scheme (III) shown above, (i) to (vi) each indicate the followings: (i) 3-amino-1-propene, AcOH, MgSO₄, CH₂Cl₂; (ii) NaBH₄, MeOH, CH₂Cl₂; (iii) Compound 2, DCC, CH₂Cl₂; (iv) Lioh•H₂O, THF, MeOH, H₂O; (v) TBSOtf, 2,6-lutidine; and (vi) Fmoc-OSu, Na₂CO₃, THF, H₂O.

As shown in Scheme (III), 2-hydroxy-4-methoxybenzaldehyde (Compound 1) is reductively aminated with 3-amino-1-propene to obtain 2-allylaminomethyl-5-methoxy-phenol (Compound 2). Next, Compound 2 is coupled with N-α-(tert-butoxycarbonyl)-L-glutamic acid α-methyl ester (Compound 3) to obtain 4-[allyl-(2-hydroxy-4-methoxy-benzy)carbamoyl]-2-tert-butoxycarbonylamino-butyric acid methyl ester (Compound 4). Next, the methyl ester in Compound 4 is hydrolyzed to obtain 4-[allyl-(2-hydroxy-4-methoxy-benzyl)carbamoyl]-2-tert-butoxycarbonylamino-butyric acid (Compound 5). Furthermore, by substituting the Boc group of Compound 5 with an Fmoc group and protecting the phenol moiety of the Hmb group with TBS, the glutamine derivative of Formula (III) can be obtained. Commercially available reagents can be used for all the reagents necessary to carry out Scheme (III).

On the other hand, synthesis of stapled ERAPs by Scheme (I) can be carried out using the glutamine derivative of the above-mentioned Formula (III), for example, as described below. First, a peptide is synthesized by standard Fmoc solid-phase peptide synthesis, with each amino acid residue of a pair, at a position where one wants to form a stapling structure in the amino acid sequence of SEQ ID NO: 4 or SEQ ID NO: 5, being substituted with the glutamine derivative of Formula (III). Then, after deprotection of the N terminus of the Fmoc-protected peptide followed by acetylation, the acetylated peptide is treated with Hoveyda-Grubbs' second-generation catalyst and an olefin metathesis reaction is carried out. Furthermore, deprotection of acid-labile protecting groups and cleavage of peptides from resin are performed using a cocktail of TFA/m-cresol/thioanisole/1,2-ethanedithiol/H₂O. Following these, stapled ERAPs or sh stapled ERAPs carrying the stapling structure of Formula (I) (the double line drawn by a solid line and a dashed line is a double bond) can be obtained. In the stapled ERAP or sh stapled ERAP synthesized by Scheme (I), the number of amino acid residues interpositioned within the stapling structure is not particularly limited, but normally the preferred number is three residues. More specifically, a structure in which a pair of amino acid residues having three residues positioned in between is substituted with a single stapling structure is a favorable example of a stapling structure in the present invention. A stapling structure having three residues positioned within it is effective for maintaining the α-helical structure of the peptide.

Furthermore, when forming a stapling structure by the intramolecular amidation reaction shown in Scheme (II), the amino acid derivatives used for stapling may be N-α-(9-fluorenylmethoxycarbonyl)-L-glutamic acid γ allyl ester represented by Formula (IV) and (S)-2-((((9H-fluoren-9-yl)methoxy)carbonyl)amino)5-((4-(((allyloxy)carbonyl)amino)butyl) (2,4-dimethoxybenzyl)amino)-5-oxopentanoic acid represented by Formula (V), shown below.

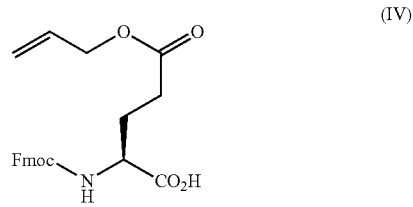

(IV)

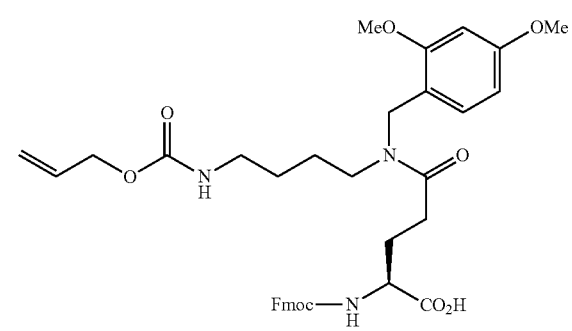

(V)

Figure 6:
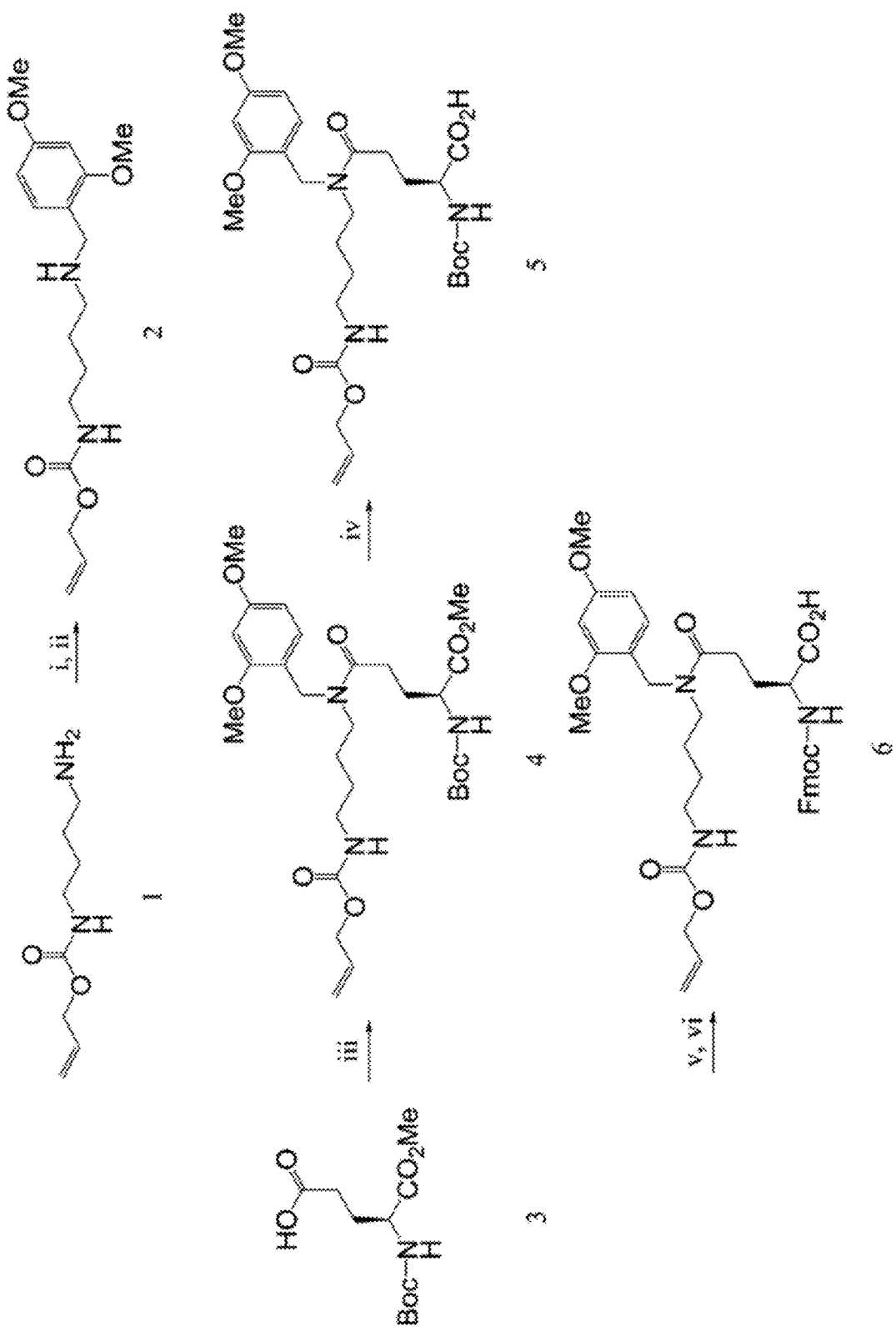
FIGS. 6 to 8 show the schemes for synthesis of a stapled ERAP.

Among the two types of amino acid derivatives described above, a commercially available product may be used for the glutamic acid derivative of Formula (IV). Furthermore, the glutamine derivative of Formula (V) can be synthesized, for example, according to the scheme shown in FIG. 6 (herein below, "Scheme (IV)"). As shown in Scheme (IV), allyl(4-aminobutyl)carbamate (Compound 1) is coupled with 2,4-dimethoxybenzaldehyde to obtain allyl[4-{(2,4-dimethoxybenzyl)amino}butyl]carbamate (Compound 2). Next, Compound 2 is coupled with N-α-(tert-butoxycarbonyl)-L-glutamic acid α methyl ester (Compound 3) to obtain (S)-methyl-5-{(4-[{(allyloxy)carbonyl}amino]butyl) (2,4-dimethoxybenzyl)amino}-2-{(tert-butoxycarbonyl)amino}-5-oxopentanoate (Compound 4). Next, the methyl ester in Compound 4 is hydrolyzed to obtain (S)-5-{(4-[{(allyloxy)carbonyl}amino]butyl) (2,4-dimethoxybenzyl)amino}-2-{(tert-butoxycarbonyl)amino}-5-oxopentanoic acid (Compound 5). Furthermore, by substituting the Boc group of Compound 5 with an Fmoc group, the glutamine derivative of Formula (V) can be obtained. Commercially available reagents can be used for all of the reagents necessary to carry out Scheme (IV).

On the other hand, synthesis of a stapled ERAP by Scheme (II) can be carried out using the glutamic acid derivative of Formula (IV) and the glutamine derivative of Formula (V) above, for example, as described below. First, a peptide is synthesized by standard Fmoc solid-phase peptide synthesis, with each one of the amino acid residues of a pair, at a position where one wants to form a stapling structure in the amino acid sequence of SEQ ID NO: 4 or SEQ ID NO: 5, being substituted with the glutamic acid derivative of Formula (IV) and the glutamine derivative of Formula (V), respectively. Then, the Fmoc-protected peptide is mixed with a solution of tetrakis(triphenylphosphine) palladium (Pd(PPh$_3$)$_4$) in CHCl$_3$/AcOH/N-methylmorpholine to reduce the substituent of the glutamine derivative residue. Next, intramolecular amidation is carried out by using N,N-diisopropylcarbodiimide (DIPCDI) and 1-hydroxy-1H-benzotriazole hydrate (HOBt.H$_2$O) to couple the glutamine derivative residues. Furthermore, deprotection of acid-labile protecting groups and cleavage of peptides from resin are performed using a cocktail of TFA/m-cresol/thioanisole/1,2-ethanedithiol/H$_2$O. Following these, stapled ERAPs or sh stapled ERAPs carrying the stapling structure of Formula (I) (the double line drawn by a solid line and a dashed line is a single bond) can be obtained. In the stapled ERAP or sh stapled ERAP synthesized by Scheme (II), the number of amino acid residues interpositioned within the stapling structure is not particularly limited, but normally the preferred number is three residues.

After introducing the first stapling structure (i.e., the first pair), similar reactions can be repeated to synthesize the peptide chain up to the position where the next stapled structure (i.e., the second pair) is to be introduced. Subsequently, by a second intramolecular crosslinking reaction, the stapling structure for the second pair is yielded. To further increase the number of crosslinking structures, structures of interest can be obtained by repeating similar reactions. Alternatively, two (or more) of peptide fragments to each of which a single stapling structure is introduced may be linked to produce a peptide introduced with two (or more) stapling structures.

Therefore, in a certain embodiment, the two pairs of amino acid residues substituted by stapling structures are at least adjacent to each other, or are independently positioned with one or more amino acid residues interposed inbetween them. More specifically, amino acid residues present within a single stapling structure are normally not substituted by another stapling structure. For example, when introducing stapling structures for two pairs, the number of amino acid residues present between the stapling structures may be, for example, zero (i.e., adjacent), one, two, or three. Considering the conditions such as the above, a peptide having a favorable structure in the present invention includes a peptide in which a pair of amino acid residues at a N-terminal side and, zero to three residues apart from it, a second pair of amino acid residues positioned at a C terminal side in the amino acid sequence of SEQ ID NO: 4 or 5 are each substituted with a stapling structure. Furthermore, by designing such that at least one amino acid residue constituting the amino acid pairs is L, the peptide is expected to become resistant to the actions of chymotrypsin.

Specific structural examples of the peptides of the present invention include structures comprising at least two stapling structures, which are represented by Formula (II) shown below:

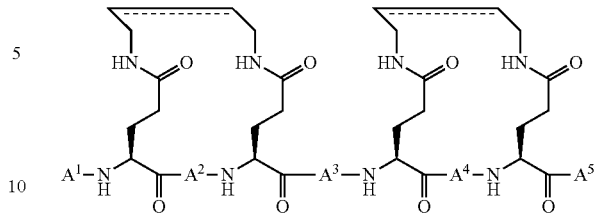

(wherein, the double line drawn by a solid line and a dashed line indicates a single bond or a double bond;
the combination of A$^1$, A$^2$, A$^3$, A$^4$, and A$^5$ is selected from the following:
A$^1$=QM, A$^2$=SDL, A$^3$=-, A$^4$=QLR, and A$^5$=R; and
A$^1$=QM, A$^2$=SDL, A$^3$=LQ, A$^4$=RQR, and A$^5$=OH;
wherein "-" indicates a peptide bond with no additional amino acid residue (that is, two stapling structures are connected); and
"OH" indicates that one end of the above stapling structure constitutes the C terminus of the peptide derivative).

The peptides comprising stapling structures, which are represented by Formula (II) above, may also be referred to as peptides formed by substituting each of the two pairs of amino acid residues (a) and (b) below by the stapling structure of Formula (I) in the peptide consisting of the amino acid sequence of SEQ NO: 4 (QMLSDLTLQLRQR):
    (a) the third (L) and seventh (T) amino acid residues from the N terminus of the amino acid sequence of SEQ ID NO: 4; and
    (b) the eighth (L) and twelfth (Q) amino acid residues from the N terminus of the amino acid sequence of SEQ ID NO: 4.

Alternatively, they are peptides formed by substituting the two pairs of amino acid residues (c) and (d) below by the stapling structure of Formula (I) in the peptide consisting of the amino acid sequence of SEQ ID NO: 5 (QMLSDLTLQLRQRQ):
    (c) the third (L) and seventh (T) amino acid residues from the N terminus of the amino acid sequence of SEQ ID NO: 5; and
    (d) the tenth (L) and fourteenth (Q) amino acid residues from the N terminus of the amino acid sequence of SEQ ID NO: 5.

Among the peptides comprising at least two stapling structures, which are represented by Formula (II), particularly preferred peptides include peptides in which the combination of A$^1$, A$^2$, A$^3$, A$^4$, and A$^5$ in Formula (II) is selected from the following:
A$^1$=QM, A$^2$=SDL, A$^3$=-, A$^4$=QLR, and A$^5$=R; and
A$^1$=QM, A$^2$=SDL, A$^3$=LQ, A$^4$=RQR, and A$^5$=OH;
wherein "-" indicates a peptide bond with no additional amino acid residue (that is, two stapling structures are connected); and
"OH" indicates that one end of the above stapling structure constitutes the C terminus of the peptide derivative);
These peptides correspond to the following peptides:
(i) peptides formed by substituting each of the two pairs of amino acid residues (a) and (b) below by the stapling structure of Formula (I) in the peptide consisting of the amino acid sequence of SEQ ID NO: 4 (QMLSDLTLQLRQR):
    (a) the third (L) and seventh (T) amino acid residues from the N terminus of the amino acid sequence of SEQ ID NO: 4; and (b) the eighth (L) and twelfth (Q) amino acid residues from the N terminus of the amino acid sequence of SEQ ID NO: 4; or (ii) peptides formed by substituting each of the two pairs of amino acid residues (c) and (d) below by the stapling structure of Formula (I) in the peptide consisting of the amino acid sequence of SEQ ID NO: 5 (QMLSDLTLQLRQRQ):

(c) the third (L) and seventh (T) amino acid residues from the N terminus of the amino acid sequence of SEQ ID NO: 5; and (d) the tenth (L) and fourteenth (Q) amino acid residues from the N terminus of the amino acid sequence of SEQ ID NO: 5.

Peptides of the present invention encompass peptides in which either or both of the N-terminal and C-terminal amino acid residues have been modified. The types of modifications are not particularly limited, but those that do not affect the affinity for PHB2 or cell permeability are preferred. Examples of preferred modifications include acetylation of the N-terminal amino acid residue, amidation of the C-terminal amino acid residue, addition of tag peptides such as HA-tag and FLAG-tag, and such. Furthermore, particularly preferred examples of the peptides of the present invention include peptides in which the N-terminal amino acid residue is acetylated and the C-terminal amino acid residue is amidated in the peptide represented by Formula (II) above. Amino acid residues other than the N-terminal and C-terminal amino acid residues are preferably not modified.

The peptides of the present invention are not limited to those composed of L-amino acids and may be peptides including one or more D-amino acids. The composition ratio of L-amino acids and D-amino acids in a peptide is not particularly limited, but for maintaining an α-helical structure, it is preferred that all amino acid residues are of the L-form (hereinafter, "L-form peptide") or all amino acid residues are of the D-form (hereinafter, "D-form peptide"). Therefore, in any one of the above-mentioned peptides of the present invention, peptides in which all amino acid residues have been substituted with D-form amino acid residues are also included as preferred embodiments of the peptides of the present invention. When the peptides of the present invention are D-form peptides, examples of preferred peptides may include peptides in which all amino acid residues in the peptides represented by Formula (II) have been substituted with D-form amino acid residues.

Furthermore, the peptides of the present invention may be retro-inverso forms of any of the above-mentioned peptides of the present invention. A retro-inverso form has an amino acid sequence that is reversed from that of the original peptide, and all amino acid residues are substituted with D-form amino acid residues. More specifically, a retro-inverso form is a D-form peptide having an amino acid sequence that is reversed from that of the original peptide. Therefore, peptides which are retro-inverso forms of any one of the above-mentioned peptides of the present invention are included as preferred embodiments of the peptides of the present invention. When the peptides of the present invention are retro-inverso forms, examples of preferred peptides include peptides which are the retro-inverso forms of the peptides represented by Formula (II).

When the peptides of the present invention are D-form peptides, D-form stapled ERAPs or sh stapled ERAPs can be synthesized by using D-amino acids instead of L-amino acids in methods as described above. In the synthesis of D-form stapled ERAPs or sh stapled ERAPs, D-form amino acid derivatives are used as the amino acid derivatives for forming stapling structures. Some of the D-form amino acid derivatives that can be used for forming stapling structures are commercially available. Therefore, such commercially available D-form amino acid derivatives may be used.

Furthermore, when synthesizing D-form stapled ERAP by Scheme (I) shown in FIG. 7, a D-form optical isomer of the glutamine derivative represented by Formula (III) (hereinafter, "D-glutamine derivative of Formula (III)") may be used as the amino acid derivative for stapling. The D-glutamine derivative of Formula (III) can be synthesized by using N-α-(tert-butoxycarbonyl)-D-glutamic acid α methyl ester instead of N-α-(tert-butoxycarbonyl)-L-glutamic acid α methyl ester (Compound 3) in the above-mentioned Scheme (III). Then, a D-form stapled ERAP can be obtained by synthesizing a D-form peptide through standard Fmoc solid-phase peptide synthesis using D-amino acids, with each amino acid residue of a pair at a position where one wants to form a stapling structure in the amino acid sequence of SEQ ID NO: 4 or SEQ ID NO: 5 being substituted with the D-glutamine derivative of Formula (III), and performing an olefin metathesis reaction according to Scheme (I). When synthesizing the retro-inverso form of a stapled ERAP or a sh stapled ERAP, solid-phase peptide synthesis can be performed based on the reversed amino acid sequence of the amino acid sequence of SEQ ID NO: 4 or 5 or a partial sequence thereof. Likewise the above, in this case too each amino acid residue of a pair, at a position where one wants to form a stapling structure, is substituted with the D-glutamine derivative of Formula (III) and then an olefin metathesis reaction is performed after synthesizing the peptide.

Figure 8:
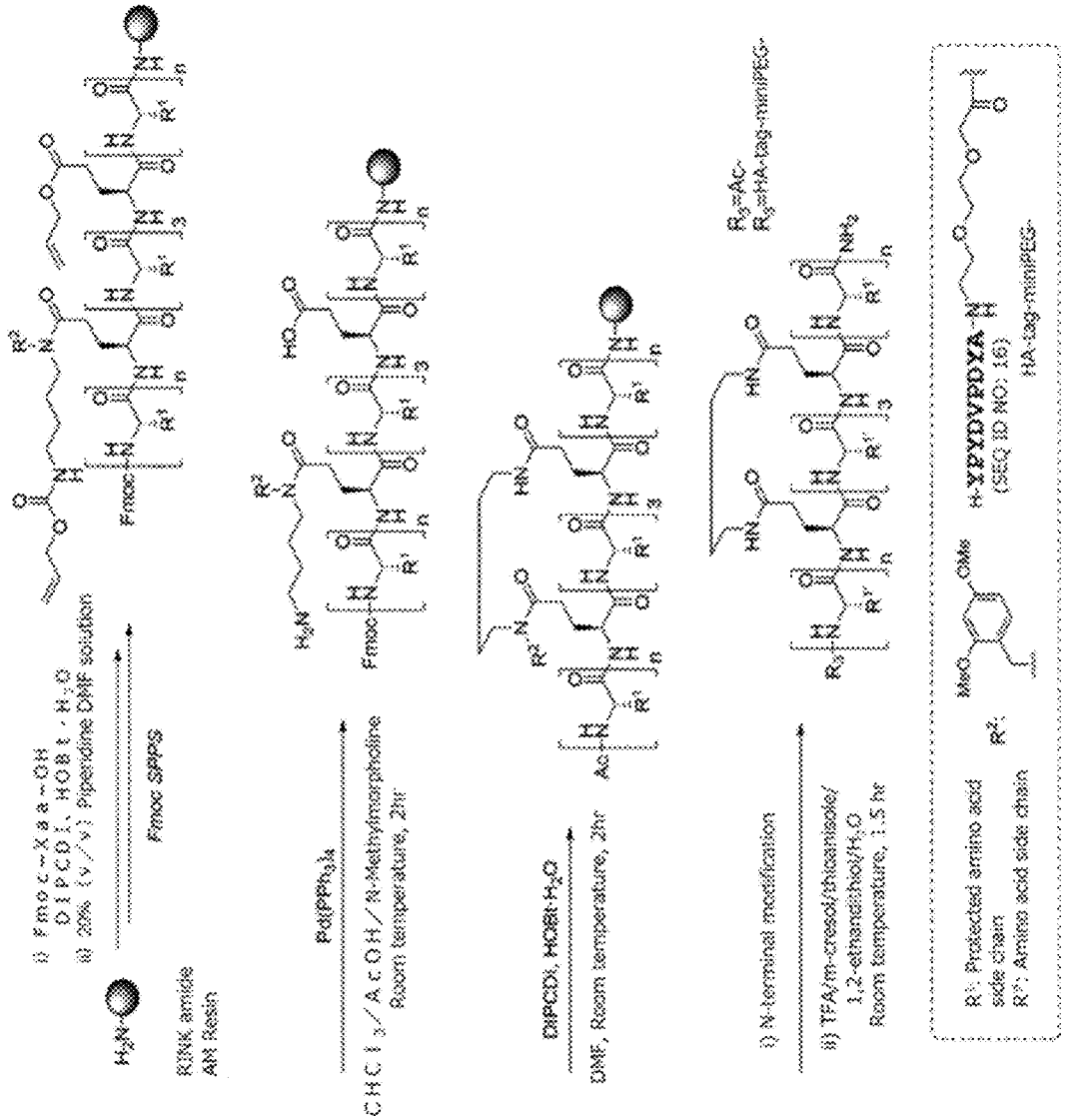

When synthesizing a D-form stapled ERAP by Scheme (II) shown in FIG. 8, the D-form optical isomer of the glutamic acid derivative represented by Formula (IV) (hereinafter, "D-glutamic acid derivative of Formula (IV)") and the D-form optical isomer of the glutamine derivative represented by Formula (V) (hereinafter, "D-glutamine derivative of Formula (V)") can be used as the amino acid derivatives for stapling. Commercially available products can be used for the D-glutamic acid derivative of Formula (IV). The D-glutamine derivative of Formula (V) can be synthesized by using N-α-(tert-butoxycarbonyl)-D-glutamic acid α methyl ester instead of N-α-(teat-butoxycarbonyl)-L-glutamic acid a methyl ester (Compound 3) in Scheme (IV) shown in FIG. 6. Then, a D-form stapled ERAP can be obtained by synthesizing a D-form peptide through standard Fmoc solid-phase peptide synthesis using D-amino acids, with each one of the amino acid residues of a pair at a position where one wants to form a stapling structure in the amino acid sequence of SEQ ID NO: 4 or SEQ ID NO: 5 being substituted with the D-glutamic acid derivative of Formula (IV) and the D-glutamine derivative of Formula (V) respectively, and performing an intramolecular amidation reaction according to Scheme (II). When synthesizing the retro-inverso forms of stapled ERAPs, solid-phase peptide synthesis can be performed based on the reversed amino acid sequence of the amino acid sequence of SEQ ID NO: 4 or SEQ ID NO: 5. Likewise the above, in this case too each amino acid residue of a pair at a position where one wants to form a stapling structure is substituted with the D-glutamic acid derivative of Formula (IV) and the D-glutamine derivative of Formula (V), respectively, and then an intramolecular amidation reaction is performed after synthesizing the peptide.

Peptides of the present invention may also be in the form of salts. The form of salts is not particularly limited, but pharmaceutically acceptable salts are preferred. Herein, the "pharmaceutically acceptable salt" refers to a salt that retains the pharmacological and pharmaceutical efficacy and characteristics of a peptide. Preferred examples of salts include salts with alkali metals (lithium, potassium, sodium and such), salts with alkaline-earth metals (calcium, magnesium and such), salts with other metals (copper, iron, zinc, manganese and such), salts with organic bases, salts with amines, salts with organic acids (acetic acid, formic acid, propionic acid, fumaric acid, maleic acid, succinic acid, tartaric acid, citric acid, malic acid, oxalic acid, benzoic acid, methanesulfonic acid, and such), salts with inorganic acids (hydrochloric acid, phosphoric acid, hydrobromic acid, sulfuric acid, nitric acid and such), and such. These salts can be prepared according to known methods.

Pharmaceutical Compositions

Peptides or salts thereof of the present invention can be formulated as pharmaceutical compositions along with pharmaceutically acceptable carriers.

Peptides of the present invention have a binding ability to PHB2, and competitively inhibit the BIG3-PHB2 interaction. The formation of BIG3-PHB2 complex enhances estrogen-dependent transcriptional activity and induces proliferation of cancer cells. Therefore, peptides of the present invention which suppress the formation of BIG3-PHB2 complex by inhibiting the BIG3-PHB2 interaction are useful as pharmaceutical compositions for cancer therapy in particular.

Enhancement of estrogen-dependent transcriptional activity by the formation of BIG3-PHB2 complex takes place mainly in estrogen receptor-positive cells. Therefore, peptides of the present invention are useful as pharmaceutical compositions for therapy of estrogen receptor-positive cancer in particular. Examples of such estrogen receptor-positive cancer include breast cancer, endometrial cancer, ovarian cancer, prostate cancer (Nelles J L, et al., Expert Rev Endocrinol Metab. 2011 May; 6(3): 437-451), and lung cancer (particularly non-small-cell lung cancer) (Stabile L P, et al., Cancer Res. 2005 Feb. 15; 65(4): 1459-70; Marquez-Garban D C, et al., Steroids. 2007 February; 72(2): 135-43), but are not limited thereto. Cancers to which pharmaceutical compositions of the present invention are applied preferably express BIG3 and PHB2, and estrogen receptor-positive cancers generally express BIG3 and PHB2. Whether a cancer is estrogen receptor-positive can be confirmed by known methods such as ELISA or immunohistochemical staining.

Furthermore, peptides of the present invention have growth suppressive effects on tamoxifen-resistant estrogen receptor-positive cancers as well. Therefore, pharmaceutical compositions of the present invention may also be applied to tamoxifen-resistant estrogen receptor-positive cancers. An example of tamoxifen-resistant estrogen receptor-positive cancers to which pharmaceutical compositions of the present invention will be applied includes tamoxifen-resistant estrogen receptor-positive breast cancer. Therefore, an example of preferred subjects to whom a pharmaceutical composition of the present invention is to be administered includes patients with tamoxifen-refractory estrogen receptor-positive breast cancer.

Furthermore, the peptides of the present invention showed inhibitory effects on the growth of breast cancer cells having a mutation in the estrogen receptor (ESR1). The mutation in ESR1 is considered as one mechanism for the acquisition of resistance to hormone therapy. Furthermore, the peptides of the present invention showed excellent cell growth inhibitory effects in triple-negative breast cancer cells (FIG. 30). Generally, triple-negative refers to breast cancer cells lacking expression of HER2, estrogen receptors, and progesterone receptors, which are targeted factors in major drug therapies. Therefore, triple-negative breast cancers are normally resistant to drug therapy. In addition, the present inventors discovered that the peptides of the present invention have high cell growth inhibitory effects against cells of HER2-positive breast cancer which is generally known as highly malignant breast cancer. Therefore, the peptides of the present invention are useful as pharmaceutical compositions for administration to patients with such treatment-resistant or malignant breast cancers.

More specifically, the present invention provides pharmaceutical compositions comprising a peptide of the present invention, which are for administration to either or both of drug therapy-resistant breast cancer patients and malignant breast cancer. The present invention also relates to peptides of the present invention for use in treatment of either or both of drug therapy-resistant breast cancer patients and malignant breast cancer. Furthermore, the present invention relates to use of the peptides of the present invention in the production of pharmaceutical compositions for treating either or both of drug therapy-resistant breast cancer patients and malignant breast cancer. The present invention also provides methods for treating breast cancer which comprise the steps of selecting patients having either or both of drug therapy-resistant breast cancer and malignant breast cancer, and administering a peptide of the present invention to the selected patients.

Patients with drug therapy resistant breast cancer can be identified by observing the therapeutic outcome after common drug therapy. Specifically, when degeneration of the disease focus is not clearly observed by the treatment, one can know that this cancer is treatment-resistant. A condition where enlargement of the disease focus is prevented is included in the degeneration of the disease focus. Alternatively, markers for predicting the malignancy of breast cancer are known. When such markers are detected, one can know that the patient has highly malignant breast cancer. For example, HER2 is one indicator for malignant breast cancer. Furthermore, triple-negative breast cancer patients are said to have resistance to drug therapies. Triple-negative refers to breast cancers having the features of lacking expression of estrogen receptors and progesterone receptors in addition to the aforementioned HER2. These markers for malignancy and drug therapy resistance can be evaluated quantitatively by immunostaining and gene expression profiling. For example, the marker status is determined to be negative when the expression level is approximately the same as that of a negative control. For the negative control, treatment-resistant cancer cell lines lacking expression of these markers can be used.

Pharmaceutical compositions of the present invention can be produced using known drug formulation techniques by mixing a peptide or a salt thereof of the present invention with a pharmaceutically acceptable carrier. Herein, "pharmaceutically acceptable carrier" refers to an inactive substance to be used as diluents or solvents for drugs. For the pharmaceutically acceptable carriers to be used in pharmaceutical compositions of the present invention, carriers generally used for pharmaceutical products can be appropriately selected according to the dosage form of the pharmaceutical compositions to be prepared.

The dosage forms of the pharmaceutical compositions of the present invention are not particularly limited, and dosage forms generally used for pharmaceutical products such as liquids, tablets, elixirs, capsules, granules, and powders can be selected appropriately. Furthermore, depending on the selected dosage form, additives such as excipients, stabilizers, suspensions, preservatives, surfactants, solubilizing agents, pH adjusters, and aggregation inhibitors can be added appropriately.

Pharmaceutical compositions of the present invention contain a pharmaceutically effective amount of peptides or salts thereof of the present invention. The pharmaceutically effective amount can be selected appropriately according to the dosage form of the pharmaceutical compositions, dosage interval, age, gender, body weight, and body surface area of subjects for administration, type of disease, and such. Examples of the content of peptides or salts thereof of the present invention in pharmaceutical compositions of the present invention include 0.001 mg to 1000 mg, 0.01 mg to 100 mg, 0.1 mg to 30 mg, or 0.1 mg to 10 mg, but are not limited thereto.

Pharmaceutical compositions of the present invention may optionally include other pharmaceutical agents. Examples of other pharmaceutical agents include anti-inflammatory agents, analgesic agents, antipyretics, other therapeutic agents for cancer, and such. Other therapeutic agents for cancer that may be used for pharmaceutical compositions of the present invention are not particularly limited, but when the pharmaceutical compositions are used for estrogen-positive cancers, examples may include hormone therapy agents such as selective ERα modulators (e.g., tamoxifen and raloxifene), ERα down-regulators (e.g., fulvestrant), aromatase inhibitors, LH-RH agonist formulations, and progesterone formulations. These pharmaceutical agents may also be mixed in the form of prodrugs and pharmaceutically acceptable salts.

Pharmaceutical compositions of the present invention can be administered to a subject by appropriately selecting a suitable administration route depending on the dosage form. The administration route is not particularly limited, but examples include oral administration, intradermal, subcutaneous, intramuscular, intraosseous, peritoneal and intravenous injection, and such. Furthermore, while either systemic administration or local administration near the diseased site is possible, local administration is preferred. More specifically, pharmaceutical compositions of the present invention can be administered by means of injection and such to the cancer tissue or to its vicinity. Alternatively, pharmaceutical compositions of the present invention can be administered surgically into the cancer tissue or to its vicinity. Pharmaceutical compositions of the present invention can also be prepared as a controlled-release preparation by combining them with appropriate carriers.

Dosage interval of pharmaceutical compositions of the present invention may also be appropriately selected according to the age, gender, body weight, and body surface area of subjects for administration, the disease type and such, as well as the dosage form, administration route, and such of the pharmaceutical compositions of the present invention. Examples of the dosage interval include every day, every four days, and every seven days, but are not limited thereto.

Dosage or pharmaceutical compositions of the present invention may also be appropriately selected according to the age, gender, body weight, and body surface area of subjects for administration, the disease type and such, as well as the dosage form, administration route, and such of the pharmaceutical compositions of the present invention.

Examples of the dosage of peptides or salts thereof of the present invention include, for example, 0.001 mg/kg/day to 1000 mg/kg/day, 0.005 mg/kg/day to 500 mg/kg/day, 0.01 mg/kg/day to 250 mg/kg/day, but are not limited thereto.

Pharmaceutical compositions of the present invention may be used in combination with other pharmaceuticals depending on the condition of the administration subjects. The pharmaceuticals used in combination are not particularly limited, but when the pharmaceutical compositions are used for estrogen receptor-positive cancers, examples may include hormone therapy agents such as selective ERα modulators (e.g., tamoxifen and raloxifene), ERα down-regulators (e.g., fulvestrant), aromatase inhibitors, LH-RH agonist formulations, and progesterone formulations. Among these hormone therapy agents, particularly preferred examples include tamoxifen and fulvestrant.

When pharmaceutical compositions of the present invention are used for cancer therapy, one may examine whether the cancer to be treated is accompanied by expression of BIG3 and PHB2 before administering the pharmaceutical compositions. Whether BIG3 and PHB2 are expressed in the cancer to be treated can be confirmed by detecting transcription products or translation products of these genes in the samples collected from the subjects. Known methods can be used for detection methods, and for example, methods of detecting transcription products using probes or PCR methods (for example, cDNA microarray method, Northern blotting, and RT-PCR) and methods of detecting translation products using antibodies and such (for example, Western blotting and immunostaining) may be used.

The present invention also provides articles of manufacture or kits that comprise a pharmaceutical composition of the present invention. The articles of manufacture or kits of the present invention can include a container that houses the pharmaceutical composition of the present invention. An example of an appropriate container includes a bottle, a vial or a test tube, but is not limited thereto. The container may be formed of various materials such as glass or plastic. A label may be attached to the container, and the disease or disease state to which the pharmaceutical composition of the present invention should be used may be described in the label. The label may also indicate directions for administration and such.

The articles or manufacture or kits of the present invention may further comprise a second container that houses pharmaceutically acceptable diluents optionally, in addition to the container that houses the pharmaceutical composition of the present invention. The articles of manufacture or kits of the present invention may further comprise the other materials desirable from a commercial standpoint and the user's perspective, such as the other buffers, diluents, filters, injection needles, syringes, and package inserts with instructions for use.

As needed, the pharmaceutical composition of the present invention can be provided in a pack or dispenser device that can contain one or more units of dosage forms containing active ingredients. The pack can include, for example, a metallic foil or a plastic foil such as a blister pack. Instructions for administration can be attached to the pack or dispenser device.

In another embodiment, the present invention provides the following use, methods, and such:

(a) use of a peptide or a salt thereof of the present invention in the production of a pharmaceutical composition for cancer therapy;

(b) a peptide or a salt thereof of the present invention for use in cancer therapy;

(c) a method or process for producing a pharmaceutical composition for cancer therapy, which comprises the step of formulating a peptide or a salt thereof of the present invention with a pharmaceutically acceptable carrier;

(d) a method or process for producing a pharmaceutical composition for cancer therapy, which comprises the step of mixing a peptide or a salt thereof of the present invention with a pharmaceutically acceptable carrier; and (e) a method for cancer therapy, which comprises administering a peptide salt thereof of the present invention to a subject.

Hereinbelow, the present invention is described in more detail with reference to the Examples. Nevertheless, while the following materials, method and Examples may serve to assist one of ordinary skill in making and using certain embodiments of the present invention, there are only intended to illustrate aspects of the present invention and thus in no way to limit the scope of the present invention. One of ordinary skill in the art can use methods and materials similar or equivalent to those described herein in the practice or testing of the present invention.

All prior art documents cited herein are incorporated by reference in the present specification.

EXAMPLE

Example 1

Synthesis of Double Stapled Peptides

Synthesis of Double Stapled ERAP No. 45 (SEQ ID NO: 2) and Stapled ERAP No. 46 (SEQ ID NO: 3)

Peptide chain elongation was performed using the Rink Amide AM Resin (content: 0.62 mmol amine/g) by Fmoc solid-phase peptide synthesis method. Unnatural amino acids Xs ($X^1$=Fmoc-Glu(OAllyl)-OH; $X^2$=Fmoc-Glu(N(DMB)-$CH_2CH_2CH_2CH_2$—NH-Alloc)-OH) were introduced at sites necessary for stapling $QMX^1SDLX^2X^1QLRX^2R$ which is the precursor sequence of double stapled ERAP No. 45 and $QMX^1SDLX^2LQX^1RQRX^2$ which is the precursor sequence of double stapled ERAP No. 46. For natural amino acids, Fmoc-Gln(Trt)-OH, Fmoc-Met-OH, Fmoc-Ser(tBu)-OH, Fmoc-Asp(OtBu)-OH, Fmoc-Leu-OH, and Fmoc-Arg(Pbf)-OH were respectively used at three equivalents relative to the resin. O-benzotriazolyl-N',N',N',N'-tetramethyluronium hexafluorophosphate (HBTU; 0.99 equivalents relative to the amino acid) and N,N-diisopropylethylamine (DIPEA; 2 equivalents relative to the amino acid) in N,N-dimethylformamide (DMF) was used for activation at room temperature for 30 seconds, and this was made to react with the amino groups on the solid resin at room temperature for 2 hours. For unnatural amino acids Xs, the amino acid was used at 1.5 equivalents relative to the resin, and by similarly using HBTU as the activator, this was reacted at room temperature for 2 hours. Cleavage of the Fmoc group was carried out by treatment with a solution of 20% piperidine in DMF at room temperature for ten minutes.

Stapling was performed when a set of $X^1$ and $X^2$ was introduced from the C-terminal side. More specifically, under an Ar atmosphere, allyl and alloc groups were removed from $N^\alpha$-Fmoc-protected peptide resins by adding $Pd(PPh_3)_4$ (3 equivalents) and stirring at room temperature for 12 hours (performed twice) in a mixed solvent of N-methylmorpholine (10 equivalents)/AcOH/$CHCl_3$ (0.5:2:37.5 (v/v)). After removing the protecting groups, the resins were washed using $CHCl_3$, DMF, 1 M sodium dimethyldithiocarbamate/DMF (semicarbazide solution), $CHCl_3$, DMF, and 1 M 1-hydroxybenzotriazole (HOBt).$H_2O$/NMP (only after the second deprotection) in that order. Then, in N-methyl-2-pyrrolidone (NMP), 1 M HOBt.$H_2O$/NMP (10 equivalents) and DIPCI (10 equivalents) were added and this mixture was reacted at room temperature for 24 hours for intramolecular amide bond formation. For the second stapling, a similar method as described above was performed on the $N^\alpha$-acetylated resin after completion of resin elongation. Furthermore, the N terminus was acetylated using $(AcO)_2O$ (10 equivalents relative to the amino acid) and DIPEA (10 equivalents relative to the amino acid).

The resins that have completed amino acid elongation and side chain stapling were treated with TFA/thioanisole/m-cresol/1,2-ethanediol (EDT)/$H_2O$ (80:5:5:5:5 (v/v), 50 μL of deprotection reaction solution for 1 mg of resin) at room temperature for 2 hours to cleave the side-chain protecting groups. The reaction solution was concentrated, then $Et_2O$ was added, and the crude peptide was precipitated. This was washed with $Et_2O$ three times to yield samples for HPLC purification. The conditions for peptide purification and the results from mass spectrometry are as shown below.

Double Stapled ERAP No. 45

Column: Cosmosil $5C_{18}$ (10×250 mm); Solvent:

A 0.1% TFA-$H_2O$, B 0.1% TFA in $CH_3CN$,

B (10%-45% over 30 min) in solvent A;

Flow: 3.0 mL/min; Detect: 220 nm,

Retention time 24.5 min

MS m/z calcd for $C_{76}H_{130}N_{26}O_{23}S$ $[M+2H]^+$ 904.5, found 904.6

Double Stapled ERAP No. 46

Column: Cosmosil $5C_{18}$ (10×250 mm); Solvent:

A 0.1% TFA-$H_2O$,

B 0.1% TFA in $CH_3CN$, B (10%-45% over 30 min) in solvent A;

Flow: 3.0 mL/min; Detect: 220 nm,

Retention time 19.8 min

MS m/z calcd for $C_{81}H_{138}N_{28}O_{25}S$ $[M+2H]^+$ 968.5, Found 968.6

Structures of Unnatural Amino Acids $X^1$ and $X^2$ ($X^1$=Fmoc-Glu(OAllyl)-OH; $X^2$=Fmoc-Glu(N(DMB)-$CH_2CH_2CH_2CH_2$—NH-Alloc)-OH)

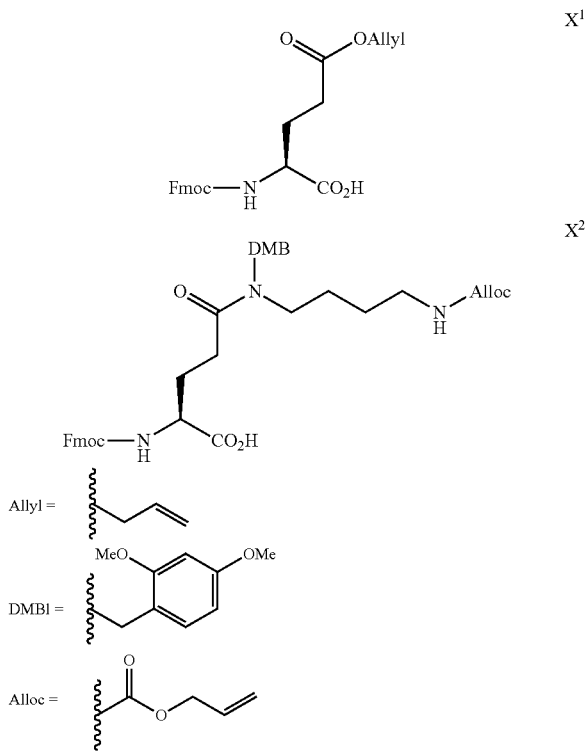

Example 2

Effects of Double Stapled ERAPs on Estrogen-Dependent Breast Cancer Cells

Materials and Methods
Cell Lines and Culturing Conditions

Human breast cancer cell line MCF-7 was purchased from JCRB Cell Bank (Osaka, Japan) and mammary epithelial cell line MCF-10A was purchased from American Type Culture Collection (ATCC, Manassas, Va., USA). Both cell lines were maintained in an appropriate medium under 5% $CO_2$ at 37° C.

For cell growth assays, the respective cells were seeded into 48-well plates ($2\times10^4$ cells/200 µL), and for immunoprecipitation, the respective cells were seeded into 10-cm dishes ($2\times10^6$ cells/10 mL).

MCF-7 cells were seeded in MEM (Thermo Fisher Scientific) supplemented with 10% FBS (Nichirei Biosciences Inc., Tokyo, Japan), 1% Antibiotic/Antimycotic solution (Thermo Fisher Scientific, Waltham, Mass., USA), 0.1 mM NEAA (Thermo Fisher Scientific), 1 mM sodium pyruvate (Thermo Fisher Scientific), and 10 µg/mL insulin (Sigma, St. Louis, Mo., USA). MCF-10A cells were seeded in MEBM (Lonza) supplemented with a Single Quots kit (BPE, hydrocortisone, hEGF, insulin, gentamycin/amphoterin-B) (Lonza, Walkersville, Md., USA) and 100 ng/mL cholera toxin. For 17β-estradiol (estrogen, Sigma) stimulation, the medium for MCF-7 cells was changed to phenol red-free DMEM/F12 (Thermo Fisher Scientific) supplemented with 10% FBS, 1% Antibiotic/Antimycotic solution, 0.1 mM NEAA, 1 mM sodium pyruvate, and 10 µg/mL insulin on the next day after seeding. 24 hours later, the cells were treated with 10 nM estrogen alone or with 10 nM estrogen and a peptide (a single stapled ERAP or a double stapled ERAP).

Cell Growth Assay

Cell growth assays on MCF-7 and MCF-10A were carried out using the Cell Counting Kit-8 (CCK-8) (Dojindo, Kumamoto, Japan). The data are shown by mean±standard deviation of three independent experiments.

Chymotrypsin Resistance

Chymotrypsin resistance was analyzed by adding 1 µg of chymotrypsin (#C7761, Sigma) and 5 µg of double stapled ERAP in a buffer (50 mM Tris-HCl; pH 8.0, 10 mM $CaCl_2$), allowing this to react at 37° C. for 24 hours, and then subjecting the whole amount to high-performance liquid chromatography (HPLC). For the HPLC, a reverse-phase column (Inertsil Peptides C18 250×3.0 mm I.D.; GL Science, Tokyo, Japan) was used, gradient elution was performed using Solution A (0.1% trifluoroacetic acid) and Solution B (0.1% trifluoroacetic acid/acetonitrile) (A/B=90/10 (0-20 min), 90/10-40/60 (20-80 min)) at a flow rate of 0.3 mL/min, and a chromatogram for each double stapled ERAP was obtained by UV detection at 210 nm.

Antibodies and Immunoblot Analyses

For immunoblot analyses, after performing SDS-PAGE, the membranes blotted with proteins were blocked with 4% BlockAce solution (Dainippon Pharmaceutical, Osaka, Japan) for 3 hours and then incubated to react for 12 hours with antibodies against BIG3 (1:1,000) and PHB2 (1:1,000) (Abcam, Cambridge, UK). After allowing interaction with HRP-labeled secondary antibodies (anti-rat IgG-HRP for BIG3, 1:5,000; and anti-rabbit IgG-HRP for PHB2, 1:1,000) (Santa Cruz Biotechnology, Dallas, Tex., USA) for 1 hour, the blots were developed with the Enhanced Chemiluminescence (ECL) system (GE Healthcare, Buckinghamshire, UK) and scanned using the Image Reader LAS-3000 mini (Fujifilm, Tokyo, Japan).

Immunoprecipitation

For immunoprecipitation analysis, cell lysates lysed in a cell lysis buffer (50 mM Tris-HCl; pH 8.0, 150 mM NaCl, 0.1% NP-40, and 0.5% CHAPS; 0.1% protease inhibitor cocktail III) were pre-cleared with a rat IgG antibody and rec-Protein G Sepharose 4B (Thermo Fisher Scientific) at 4° C. for 3 hours. Then, the supernatants were incubated for reaction with 5 µg of an antibody against BIG3 at 4° C. for 12 hours. Next, the antigen-antibody complexes were precipitated using rec-Protein G Sepharose 4B at 4° C. for 1 hour. The immunoprecipitated protein complexes were washed four times with the cell lysis buffer. Then, SDS-PAGE and immunoblot analyses were carried out.

Results

Synthesis of Double Stapled ERAP (See the Method for Synthesizing Double Stapled ERAPs of Example 1)

Stable long-term inhibition of estrogen-dependent tumor growth was possible with single stapled ERAP (SEQ ID NO: 1); however, further enhancement of stability was undertaken by increasing the number of intramolecular crosslinks. The positions for the intramolecular crosslinks were designed to crosslink leucine residues by considering resistance to chymotrypsin, and double stapled ERAPs having, in addition to the crosslinking position for single stapled ERAP (167L and 171T), a crosslink between 172L and 175Q (FIG. 1, double stapled ERAP No. 45) and a crosslink between 174L and 178Q (FIG. 1, double stapled ERAP No. 46) were synthesized.

Figure 2B:
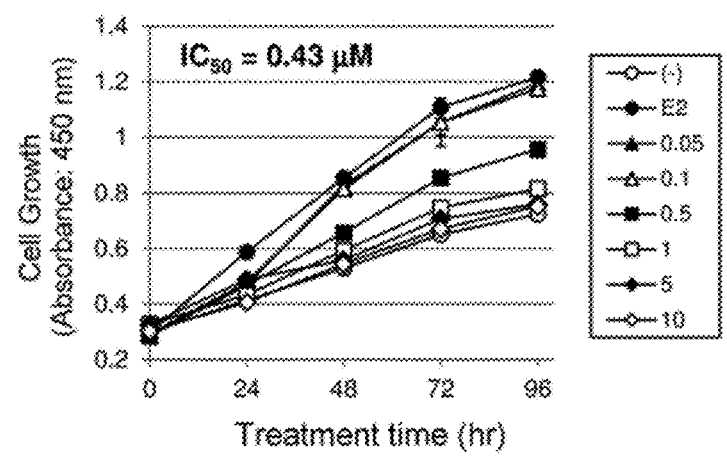
Figure 2C:
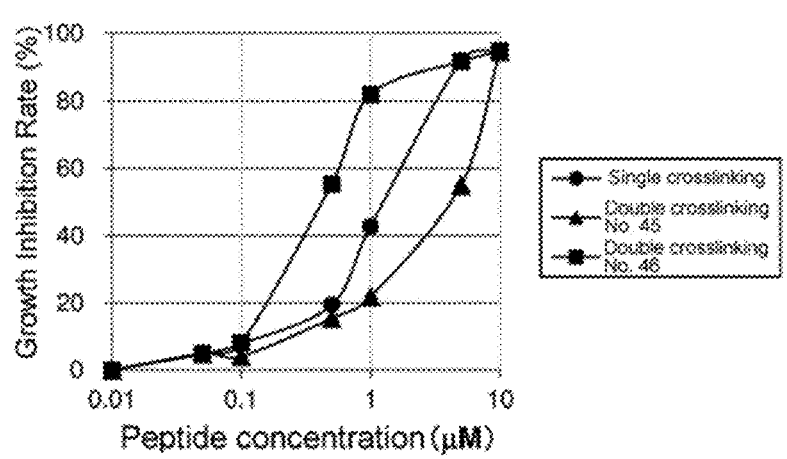

Long-Term Stability of Double Stapled ERAPs on Estrogen-Dependent Growth 96-hour treatment with single stapled ERAP suppressed the growth of estrogen-dependent MCF-7 cells in a concentration-dependent manner, and the $IC_{50}$ was 0.88 µM. Treatment with double stapled ERAP No. 45 at 10 µM for 96 hours sustained almost complete suppressive effects; however, up to 1 µM, estrogen-dependent cell growth could hardly be suppressed, its inhibitory effect was inferior to that of single stapled ERAP ($IC_{50}$=2.32 µM, FIG. 2A). This indicates the possibility that the three-dimensional structure of the continuous stapling has an influence on membrane permeability and such. On the other hand, double stapled ERAP No. 46 was different from double stapled ERAP No. 45 in that its inhibitory effect on estrogen-dependent growth was stronger than that of the single stapled ERAP, and showed 81% inhibition rate even at 1 µM (FIG. 2B, single stapled ERAP: 51% inhibition rate; double stapled ERAP No. 45: 21% inhibition rate), and its $IC_{50}$ was 0.43 µM which is two-fold enhanced than the single stapled ERAP (FIG. 2C).

Chymotrypsin-Resistance of Double Stapled ERAPs

Resistance of double stapled ERAPs No. 45 and No. 46 to treatment with chymotrypsin for 24 hours was examined. Proteolysis by chymotrypsin treatment is indicated by a black arrow in FIGS. 3A-B. The results show that while chymotrypsin treatment of double stapled ERAP No. 45 led to observation of several degradation products (FIG. 3A), chymotrypsin treatment of double stapled ERAP No. 46 hardly showed its degradation (FIG. 3B). Resistance to proteolysis by chymotrypsin treatment suggests that ERAP is resistant to degradation in vivo, and this may be reflected in maintenance of long-term stable inhibitory effects on estrogen-dependent cell growth.

Effects of Double Stapled ERAP on Mammary Epithelial Cell Growth

Figure 4:
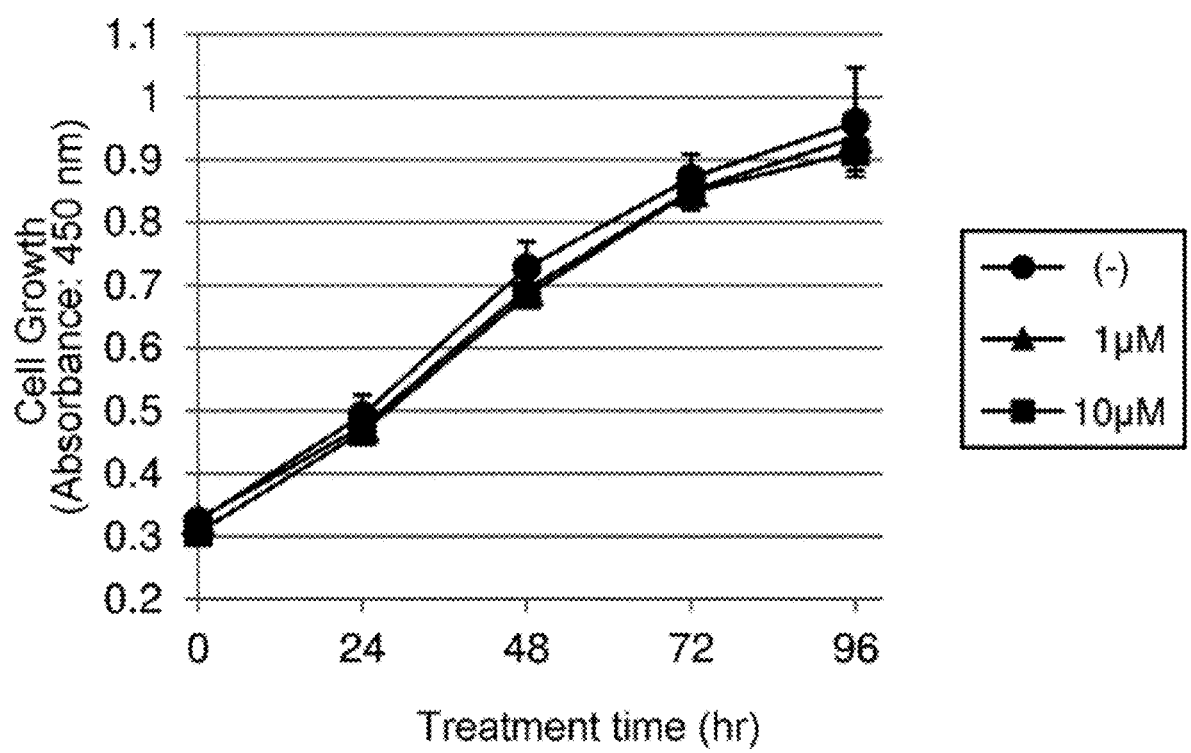
FIG. 4 shows the results of MTT assay which indicate that double stapled ERAP No. 46 has no effect against the growth of mammary epithelial cell line MCF-10A. MCF-10A cells were treated with the double stapled ERAP at the concentrations shown in the drawing up to 96 hours, and cell growth was evaluated every 24 hours.

Using 1 µM and 10 µM double stapled ERAP No. 46, effects on the growth of MCF-10A cells were examined. MCF-10A cell is an ERα-negative and BIG3-negative normal mammary epithelial cell. As a result, while treatment with 1 µM and 10 µM double stapled ERAP No. 46 for 96 hours showed inhibition rates of 79% and 91% on estrogen-dependent cell growth in ERα-positive and BIG3-positive MCF-7 breast cancer cells (FIG. 2B), there were hardly any effects on MCF-10A cell growth up to 10 µM (FIG. 4), and this suggested that the double stapling structure does not become involved in the functions of normal mammary epithelial cells.

Binding Inhibition of the BIG3-PHB2 Interaction by Double Stapled ERAP No. 46

Figure 5A:
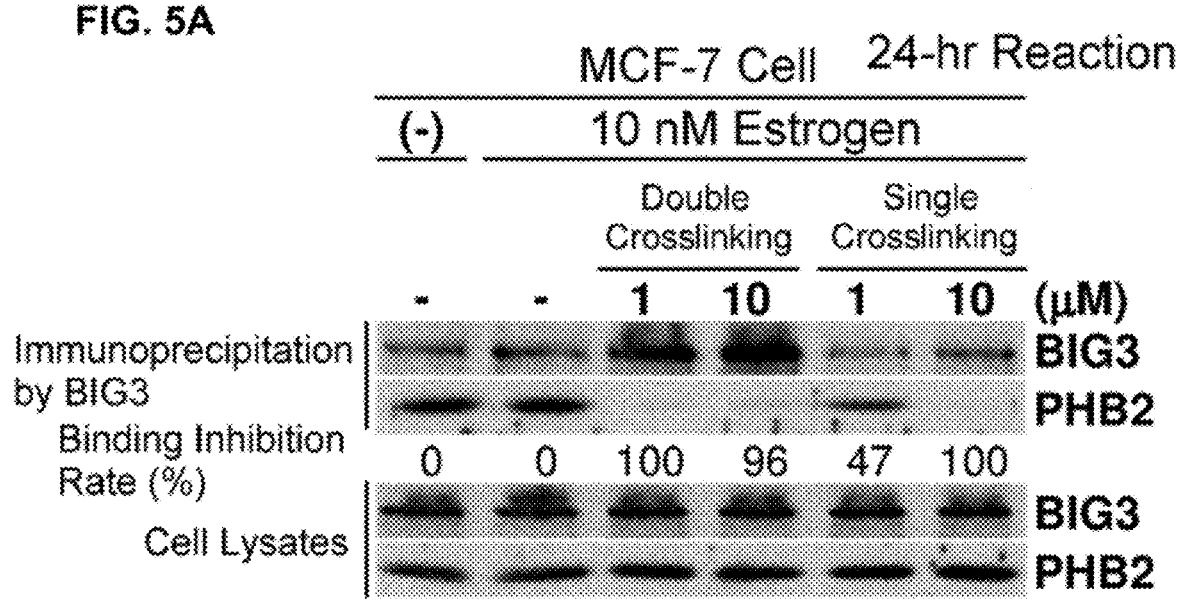
FIG. 5 shows that double stapled ERAP No. 46 inhibits the interaction between BIG3 and PHB2. (A, B) Inhibitory effect of double stapled ERAP No. 46 on BIG3-PHB2 interaction in MCF-7 cells was evaluated by Western blotting. MCF-7 cells were treated with double stapled ERAP No. 46 and single stapled ERAP at 1 µM and 10 µM, and immediately thereafter, stimulated using 10 nM estrogen for 24 hours (A) and for 96 hours (B). Then, the cells were lysed, immunoprecipitation was performed using an anti-BIG3 antibody, and immunoblot analyses were performed using the antibodies indicated in the drawing. The binding inhibition rates are expressed as proportions to the band area for PHB2 in untreated cells which is set as 100.
Figure 5B:
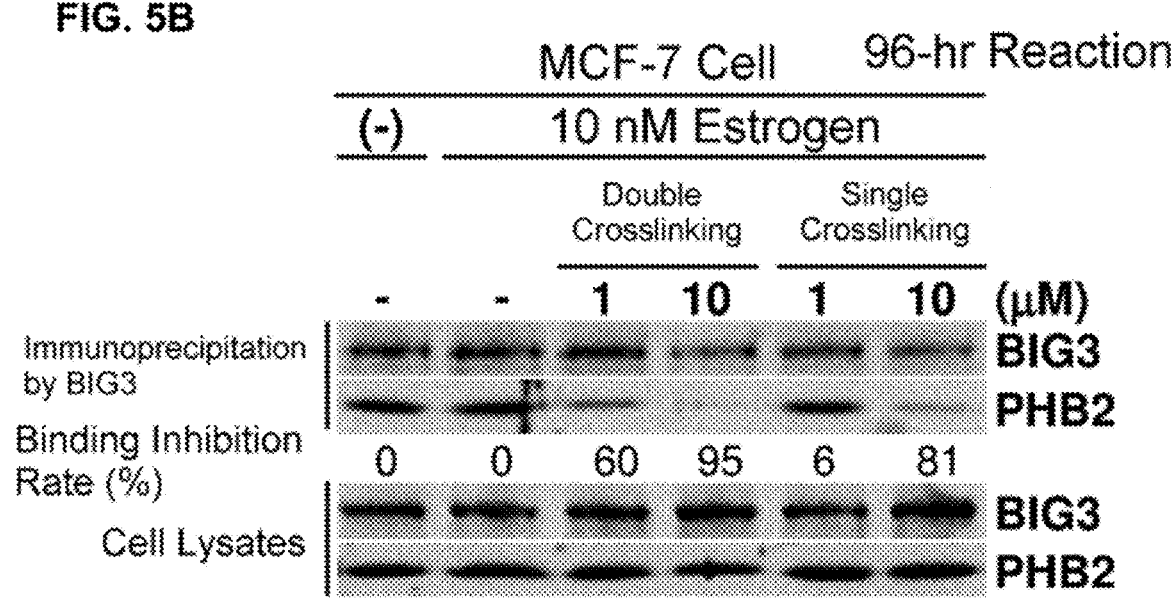

Inhibitory effect on the interaction between BIG3 and PHB2 was examined for treatment with 1 µM and 10 µM double stapled ERAP No. 46 for 24 hours and 96 hours. The results showed that 24-hour treatment with the double stapled ERAP at 1 µM nearly completely inhibited the binding between BIG3 and PHB2 (FIG. 5A); whereas, while 10 µM single stapled ERAP gave nearly complete inhibitory effect, 1 µM single stapled ERAP gave a decreased inhibition rate of 46% (FIG. 5A). Furthermore, treatment for 96 hours yielded inhibition rates of 60% and 95% for double stapled ERAP No. 46 at concentrations of 1 µM and 10 µM, respectively; therefore, while the values were slightly decreased compared to those from treatment for 24 hours (FIG. 5B), strong inhibitory effects were sustained. On the other hand, inhibitory effects were hardly observed for single stapled ERAP at 1 µM, and the inhibition rate was 81% at 10 µM (FIG. 5B). From the above-mentioned facts, double stapled ERAP No. 46 can inhibit the binding between BIG3 and PHB2 at a concentration lower than that of single stapled ERAP, and as a result, it was determined to be able to suppress growth at a lower concentration.

Example 3

Effects of stERAP on ESR1 Mutant Breast Cancer Cells

Materials and Methods
Cell Lines

MCF-7 cells and HEK293T cells were purchased from American Type Culture Collection (ATCC, Manassa, Va., USA). Y537S knock-in MCF-7 cells were provided by Dr. Laki Buluwela (Imperial College London, UK). All cell lines were cultured under conditions recommended by their respective depositors.

Cell Culture

MCF-7 cells were cultured in MEM (Thermo Fisher Scientific) supplemented with 10% FBS (Nichirei Biosciences Inc., Tokyo, Japan), 1% Antibiotic/Antimycotic solution (Thermo Fisher Scientific, Waltham, Mass., USA), 0.1 mM NEAA (Thermo Fisher Scientific), 1 mM sodium pyruvate (Thermo Fisher Scientific), and 10 µg/mL insulin (Sigma, St. Louis, Mo., USA). HEK293T cells were cultured in DMEM (Sigma) supplemented with 10% FBS and 1% antibiotic/antimycotic solution. Y537S knock-in MCF-7 cells were cultured in DMEM (Sigma) supplemented with 10% FBS, 1% antibiotic/antimycotic solution, and 0.1 mM NEAA. The respective cells were seeded into 48-well plates ($2 \times 10^4$ cells/0.2 mL), 6-well plates ($5 \times 10^5$ cells/2 mL), or 10-cm dishes ($2 \times 10^6$ cells/10 mL), incubated under 5% $CO_2$ at 37° C., and treated with an inhibitor such as stERAP 24 hours later.

Compounds and Inhibitors

For the peptide that inhibits the BIG3-PHB2 binding, the single stapled ERAP (stERAP, or stapled ERAP) described in WO 2017/12646 was used. Tamoxifen was purchased from Sigma, fulvestrant was purchased from LKT laboratories (St. Paul, Minn., USA), and everolimus was purchased from Cell Signaling Technology (Danvers, Mass., USA). Staurosporine and wortmannin were provided by OncoTherapy Science, Inc. (Kanagawa, Japan) and Dr. Takuya Sasaki (Tokushima University, Tokushima, Japan).

Western Blot Analyses

Cells were lysed in a lysis buffer (50 mM Tris-HCl: pH 8.0, 150 mM NaCl, 0.1% NP-40, 0.5% CHAPS) containing 0.1% protease inhibitor cocktail III (Calbiochem, San Diego, Calif., USA). The cell lysates were subjected to electrophoresis, transferred to nitrocellulose membranes by blotting. Then, the membranes were blocked with 4% BlockAce solution (Dainippon Pharmaceutical, Osaka, Japan) for 3 hours. The membranes were incubated for 12 hours in the presence of anti-FLAG tag antibody (M2) (Sigma); anti-PHB2 antibody (Abcam, Cambridge, UK); anti-PKCα antibody (H-7) and anti-PI3-kinase p85α (U13) (Santa Cruz Biotechnology, Santa Cruz, Calif., USA); anti-phosphorylated PI3K p85/p55 antibody (Tyr458/Tyr199), anti-phosphorylated PKCα/βII antibody (Thr638/Thr641) (Cell Signaling Technology); anti-ERα antibody (SP1) (Thermo Fisher Scientific); or anti-phosphorylated PHB2 purified antibody (Ser39) (Scrum Inc., Tokyo, Japan). After incubation in the presence of HRP-conjugated secondary antibody (Santa Cruz Biotechnology) for 1 hour, the membranes were developed with an enhanced chemiluminescence system (GE Healthcare, Buckinghamshire, UK). The blots were scanned using the Image Reader LAS-3000 mini (Fujifilm, Tokyo, Japan).

Immunoprecipitation

As described in the "Western Blot Analyses" section, the cells were lysed in a 0.1% NP-40 lysis buffer, and the cell lysates were pre-cleared with Normal IgG and rec-Protein G Sepharose 4B (Thermo Fisher Scientific) at 4° C. for 3 hours. After centrifugation, the supernatants were incubated at 4° C. for 12 hours in the presence of 5 µg of anti-PKCα antibody, anti-ERα antibody, or anti-FLAG-tagged antibody. After adding rec-Protein G Sepharose 4B and incubating at 4° C. for 1 hour, the antigen-antibody complexes were precipitated. The immunoprecipitated protein complexes were washed three times with the lysis buffer and separated by SDS-PAGE. Thereafter, Western blot analyses were carried out.

PKCα (Protein Kinase C Alpha) Activity

PKCα activity was measured by reacting the immunoprecipitates by PKCα with a PHB2 peptide carrying the substrate Ser39 (YGVRE$\underline{S}$VFTVE (SEQ ID NO: 17)) and 0.5 mM ATP in a kinase buffer solution (25 mM Hepes, pH 7.2; 25 mM $MgCl_2$; 5 mM EDTA; 5 mM EGTA; 0.25 mM DTT) at 30° C. for 30 minutes, and using the ADP-Glo kinase assay Kit (Promega, Fitchburg, Wis., USA).

Cell Growth Assay

Cell growth assay was carried out using the Cell Counting Kit-8 (CCK-8; Dojindo, Kumamoto, Japan). The cells were seeded into 48-well plates at $2 \times 10^4$ cells/well and maintained in an incubator (37° C.) in the presence of 5% $CO_2$. At a point as instructed, a ten-fold diluted CCK-8 solution was added, incubated for 30 minutes, and the absorbance at 450 nm was measured to calculate the number of viable cells.

Luciferase Reporter Assay

To perform ERE reporter assay, an ERE reporter (SABiosciences, Frederick, Md., USA) was transfected into MCF-7 cells, and 16 hours after transfection, medium was exchanged to an assay medium (Opti-MEM, 10% FBS, 0.1 mM NEAA, 1 mM Sodium pyruvate, and 10 µg/mL insulin). 8 hours after the medium exchange, cells were treated with estrogen and stERAP for 24 hours. The cell lysates were evaluated for luciferase and Renilla-luciferase activities using the Promega dual luciferase reporter assay (Promega KK, Tokyo, Japan). Considering the transfection efficiency, all data were normalized to the Renilla-luciferase activity.

Statistical Analyses

Student's t-tests were used to determine the statistical significance of the differences among the experimental groups. P<0.05 was considered significant.

Results

ESR1 Mutant Breast Cancer Cell Line Binds to PI3K Estrogen Independently

Figure 9A:
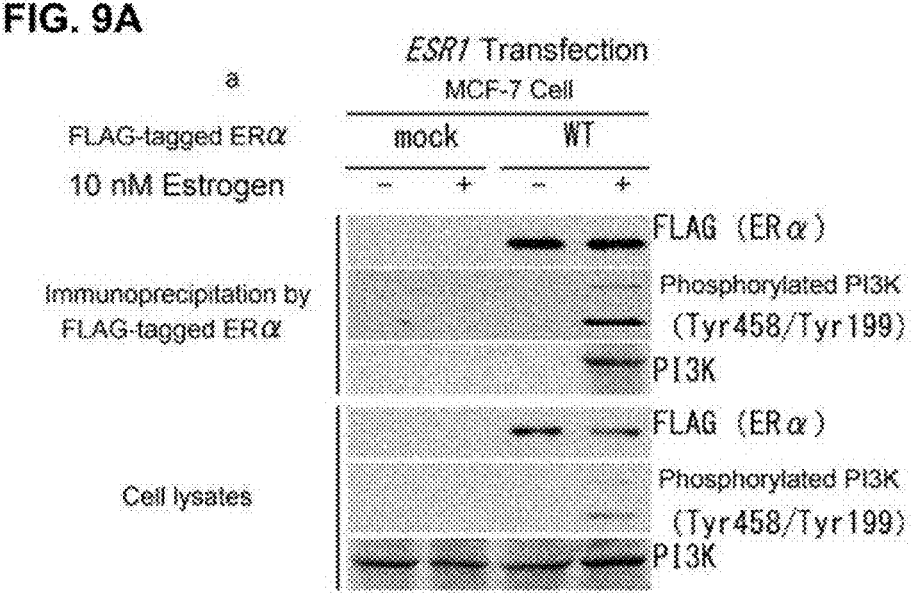
FIG. 9 shows that binding of PI3K occurs estrogen independently in an ESR1 mutant breast cancer cell line. (A) Immunoblots are shown which indicate that ERα binds with PI3K in the presence of estrogen in a breast cancer cell line carrying a wild-type ESR1. MCF-7 cells were transfected with FLAG-tagged ESR1 (WT), cell lysate thereof was subjected to immunoprecipitation using an anti-FLAG antibody, and immunoblot analyses were performed using the antibodies indicated in the drawing. (B) immunoblots are shown which analyzed the phosphorylation of PI3K, PKCα, and PHB2 when MCF-7 cells transfected with the Y537S mutant ESR1 were treated with 10 µM stERAP. MCF-7 cells were transfected with the FLAG-tagged ESR1 mutant (Y537S), lysates of cells treated with 10 µM stERAP for various lengths of time were immunoprecipitated using an anti-ERα antibody, and immunoblot analyses were performed using the antibodies indicated in the drawing.
Figure 9B:
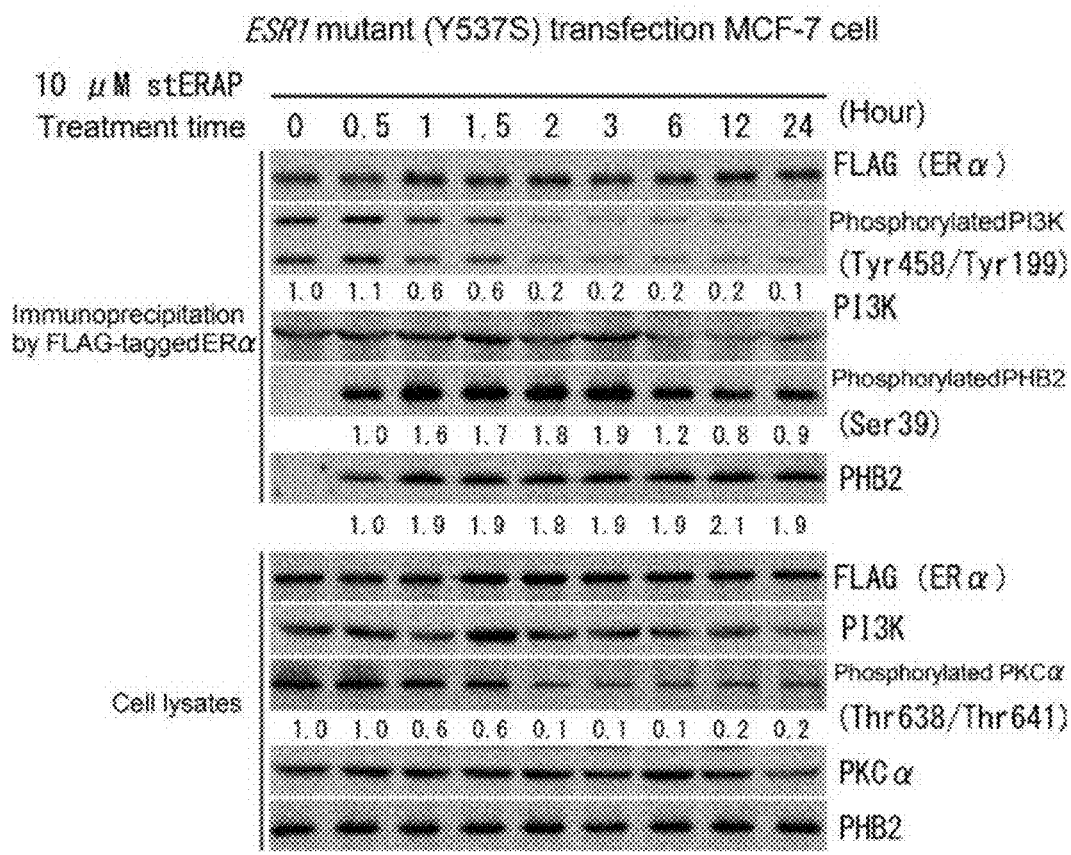

An estrogen receptor (ERα) is expressed in 70% of breast cancers, and most of these cancers are sensitive to ERα inhibition. However, in ERα-positive advanced breast cancers, mutation of the ERα gene (ESR1) is manifested in the ligand-binding domain, such gene mutations are activated in a ligand independent manner, and such cancers are suggested to have the possibility of being resistant to endocrine therapy (Nat. Genet., 45, 1439, 2013; and Nat. Genet., 45, 1446, 2013). Furthermore, in ERα-positive breast cancers, the PI3K (phosphatidylinositol 3-kinase)/AKT (protein kinase B)/mTOR (mammalian target of rapamycin) pathway in addition to the estrogen signal has a very important function, and has been reported to be involved in the mechanism of resistance to endocrine therapy (Cancer Discov. 2011 September, 1(4): 338-51; Nature, e2012 Oct. 4, 490(7418): 61-70; Cancer Lett. 2012 Oct. 1, 323(1): 77-87; Clin. Breast Cancer. 2015 June, 15(3): 197-203). First, whether wildtype (WT) and mutant (Y537S) ESR1 bind to PI3K was examined. As a result, MCF-7 cells transfected with WT did not show any binding between ERα and PI3K in the absence of estrogen treatment; however, in the presence of estrogen, binding between ERα and PI3K, and phosphorylation of PI3K were observed (FIG. 9A). On the other hand, MCF-7 cells transfected with Y537S were different from cells transfected with WT, and even in the absence of estrogen treatment, PI3K bound to Y537S and was phosphorylated, and PKCα activation (phosphorylation of Thr638/Thr641) was observed (FIG. 9B). This suggests the possibility that structural changes due to mutation of ESR1 enable estrogen-independent binding between the ESR1 mutant and PI3K, and cause acquisition of resistance. Furthermore, upon 10 µM stERAP treatment, PHB2 that had dissociated from BIG3 newly bound to Y537S even the absence of estrogen, and while the amount of the bound PHB2 reached a maximum 1 hour after stERAP treatment, thereafter, phosphorylation of PI3K and PKCα decreased (FIG. 9B). Interestingly, phosphorylation of Ser39 of PHB2 was induced immediately after stERAP treatment and maximum phosphorylation intensity was indicated in 3 hours, the intensity thereafter weakened due to decrease in phosphorylated PI3K (negative regulation of the phosphorylated PHB2; FIG. 9B). However, in comparison to the phosphorylation intensities of PI3K and PKCα, phosphorylation of PHB2 (Ser39) maintained a certain level of intensity (FIG. 9B); thus, stERAP was considered to have suppressive effects on the ERα-Y537S resistant cells.

ESR1 Mutant Breast Cancer Cell Line has Estrogen-Independent High PKCα Activity

Since ESR1 mutants bind to PI3K, it is suggested that the mutants activate PKC which is the downstream molecule of PI3K (Biochem. Biophys. Res. Commun., 310, 720, 2004). Furthermore, the present inventors have found that in ERα-positive breast cancers, activation of PKCα mediated by estrogen stimulation phosphorylates Ser39 of PHB2 (Nat. Commun., 8, 15427, 2017); therefore, PKCα activity state in ESR1 mutant breast cancer cell lines was evaluated. In the experiment, HEK293T cells and MCF-7 cells transfected with each ESR1 mutant were treated for 24 hours with PKCα inhibitor staurosporine, and immunoprecipitated with an anti-PKCα antibody. Then, PKCα activities were measured using the PHB2 peptide carrying Ser39 (YGVRE SVFTVE (SEQ ID NO: 17)) as the substrate. As a result, while ESR1 mutant cells showed remarkable PKCα activity compared to mock and WT (FIG. 10A), staurosporine treatment nearly completely suppressed this activity (FIG. 10A), suggesting the possibility that the PKCα activity in ESR1 mutant cells is derived from PI3K.

Figure 10B:
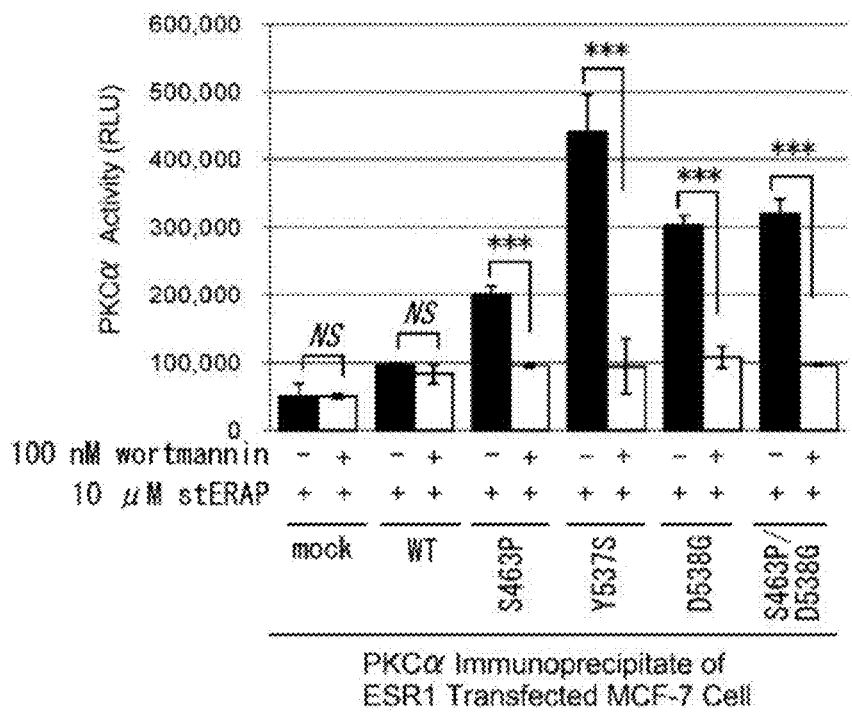
FIG. 10 shows that ESR1 mutant breast cancer cell lines have estrogen-independent high PKCα activity. (A) The PKCα activities of breast cancer cell lines transfected with an ESR1 mutant are shown. HEK293T cells and MCF-7 cells transfected with each ESR1 mutant were treated for 24 hours with PKCα inhibitor staurosporine and then subjected to immunoprecipitation using an anti-PKCα antibody, and PKCα activities were measured using the PHB2 peptide carrying Ser39 (YGVRE$\underline{S}$VFTVE (SEQ ID NO: 17)) as the substrate. The immunoprecipitates of PKCα were subjected to immunoblot analyses using the antibody indicated in the drawing. Data represent the mean±standard error of three independent experiments (***P<0.001).
Figure 10C:
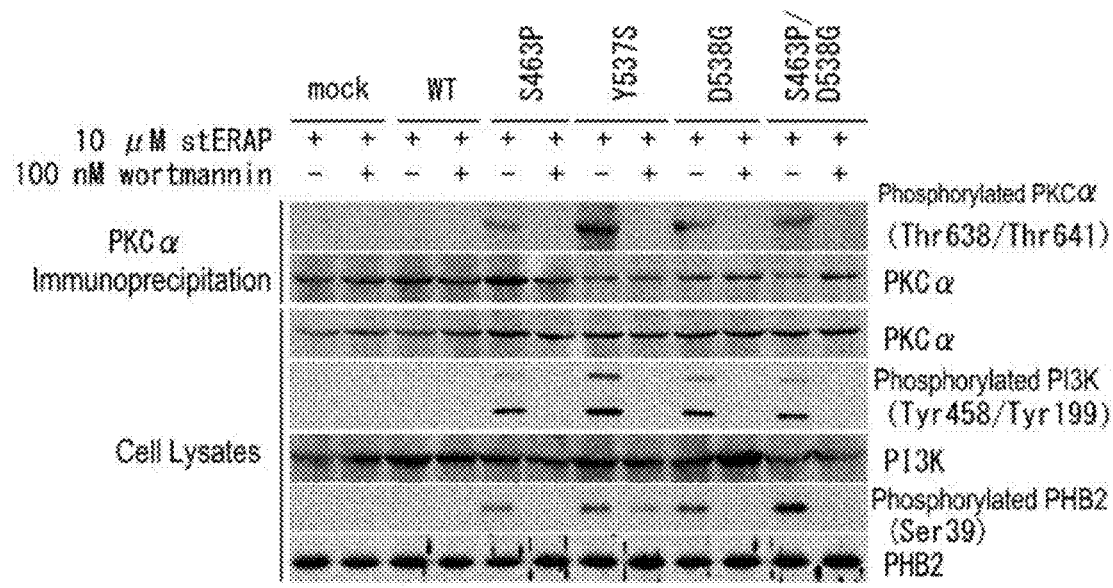

Therefore, PKCα activity and phosphorylated PI3K, when MCF-7 cells transfected with various ESR1 mutants were treated for 24 hours with PI3K inhibitor wortmannin, were evaluated. As a result, the PKCα activities of the cells transfected with various ESR1 mutants were significantly suppressed by wortmannin treatment (FIG. 10B). Furthermore, in cells transfected with an ESR1 mutant, phosphorylation of PKCα and PI3K were remarkably induced than that in the WT. However, since each of these phosphorylations were nearly completely inhibited by wortmannin (FIG. 10C), activation of PKCα was suggested to be present downstream of PI3K. Furthermore, the PKCα activity and the intensity of phosphorylated PKCα in each ESR1 mutant cell line nearly correlated with each other, and the Y537S-transfected cell line showed the highest activation and phosphorylation of PKCα.

Effects of Combined Use of stERAP and an Anti-Estrogen Agent on the Growth of an ESR1 Mutant Breast Cancer Cell Line Effects of combined use of stERAP with art existing hormone agent (tamoxifen or fulvestrant) or a molecularly-targeted drug (everolimus which is a mTOR inhibitor) on the growth MCF-7 cells made to overexpress an ESR1 mutant, were examined in a 96-hour reaction. In the experiment, transfection of each ESR1 mutant in the absence of estrogen was followed by treatment with 10 µM stERAP, 1 µM tamoxifen, 2 µM fulvestrant, and 0.5 µM everolimus. As a result, 96-hour treatment with stERAP alone significantly suppressed the growth of ESR1 mutant-transfected cells, and in particular, inhibition rate of 49% was indicated by the Y537S mutant (FIG. 11). Furthermore, combined use of tamoxifen, fulvestrant, and everolimus was able to synergistically suppress the cell growth of the ESR1 mutants, and showed inhibition rates of 80% or more for the growth of all mutant cell lines (FIG. 11).

Inhibitory Effects of stERAP on Growth of ESR1 Mutant Breast Cancer Cell Line in the Presence of Estrogen stERAP treatment in the absence of estrogen showed 40% to 50% inhibition rate on the growth of a cell line transfected with an ESR1 mutant (FIG. 11); therefore, whether the inhibitory effects of stERAP in the presence of estrogen will be enhanced was examined. As a result, treatment with stERAP alone in the absence of estrogen hardly suppressed the cell growth of mock and WT, whereas inhibition rates of 24%, 44%, 39%, and 40% were indicated for the cell growth of the S463P, Y537S, D538G, and S463P/D538G mutants, respectively (FIG. 12). On the other hand, stERAP treatment in the presence of estrogen could nearly completely suppress estrogen-stimulated growth in mock and WT, and in each of the ESR1 mutants, co-presence of estrogen at 1 nM or higher caused synergistic enhancement of the inhibitory effects of stERAP, and inhibition rates of 62%, 80%, 75%, and 77% were indicated for the S463P, Y537S, D538G, and S463P/D538G mutants, respectively (FIG. 12). Furthermore, in the co-presence of 10 nM estrogen, the inhibition rates were found to be enhanced, and the inhibition rates were 76%, 82%, 84%, and 83%, respectively (FIG. 12). Here, the possibility was considered that addition of an estrogen signal increased the sites of action of stERAP, and synergistic inhibitory effects were induced.

Inhibitory Effects of stERAP on ERα Transcriptional Activity in ESR1 Mutant Breast Cancer Cell Lines Inhibitory effects of stERAP on ERα transcriptional activity in ESR1 mutants (S463P, Y537S, D538G, and S463P+D538G) were examined. In the experiment MCF-7 cells transfected with ERE-luciferase and each of the FLAG-tagged ESR1 mutants were treated for 24 hours with stERAP in the presence of estrogen at various concentrations (0.1 nM, 1 nM, or 10 nM), and the resulting ERE-luciferase activities (ERα transcriptional activities) were measured. As a result, in cells transfected with WT FLAG-tagged ERα, ERE-luciferase activity increased in a concentration-dependent manner when estrogen concentration was 0.1 nM or higher; however, this activity was nearly completely suppressed by stERAP treatment (FIG. 13). On the other hand, in cells transfected with each ESR1 mutant, ERE-luciferase activity was remarkably induced even in the absence of estrogen (S463P: 2.3-fold; Y537S: 7.5-fold; D538G: 5.0-fold; and S463P/D538G: 6.6-fold), and in particular, cells transfected with Y537S showed induction of activity at the same level as 10 nM estrogen stimulation of WT-transfected cells (FIG. 13). Furthermore, similarly to estrogen stimulation of the WT case, stERAP could remarkably suppress ERE-luciferase activities under any of the conditions.

Inhibitor Effects of stERAP on Growth of Y537S Knocked-In MCF-7 Cells

MCF-7 cells knocked-in with Y537S of ESR1 were used to examine the effects of a 24-hour stERAP treatment on cell growth. As a result, stERAP treatment suppressed cell growth in a concentration-dependent manner even in the absence of estrogen, showed significant inhibitory effects at 10 µM (FIG. 14), and the $IC_{50}$ (50% inhibitory concentration was 1.57 µM. Furthermore, in the presence of estrogen, addition of the estrogen signal significantly enhanced the inhibition rate by stERAP, and the $IC_{50}$ was 0.78 µM.

Example 4

Effects of stERAP on Trastuzumab-Resistant HER2-Positive Breast Cancer Cells

Materials and Methods
Cell Lines

Human breast cancer cell lines (MCF-7, BT-474, and SK-BR-3) were purchased from American Type Culture Collection (ATCC, Rockville, Md., USA). KPL-4 was provided by Dr. Junichi Karebayashi (Kawasaki Medical School, Okayama, Japan) based on a Material Transfer Agreement, and trastuzumab-resistant SK-BR-3 was provided by Dr. Hirotaka Kanzaki (Okayama University, Okayama, Japan). All cell lines were cultured under conditions recommended by their respective depositors.

Cell Culture

SK-BR-3 cells were cultured in McCoy'A (Thermo Fisher Scientific) supplemented with 10% PBS (Nichirei Biosciences Inc., Tokyo, Japan) and 1% antibiotic/antimycotic solution (Thermo Fisher Scientific, Fremont, Calif., USA), and KPL-4 cells, BT-474 cells, and trastuzumab-resistant SK-BR-3 cells were cultured in DMEM (Sigma, St. Louis, Mo., USA) supplemented with 10% PBS and 1% antibiotic/antimycotic solution. The cells were seeded into 48-well plates ($2 \times 10^4$ cells/0.2 mL), 6-well plates ($5 \times 10$ cells/2 mL), or 10-cm dishes ($2 \times 10^6$ cells/10 mL), incubated under 5% $CO_2$ at 37° C., and 24 hours later, treated with an inhibitor such as stERAP.

Compounds and Inhibitors

For the peptide inhibiting the BIG3-PHB2 binding, the single stapled ERAP (stERAP) described in WO 2013/018690 was used. Recombinant PHB2 was purchased from Abnova (Taipei, Taiwan), recombinant TTK and recombinant MK5 were purchased from SignalChem (Richmond, Canada), and TTK inhibitor AZ3146 was purchased from Santa Cruz Biotechnology.

Western Blot Analyses

Cells were lysed in a lysis buffer (50 mM Tris-HCl: pH 8.0, 150 mM NaCl, 0.1% NP-40, 0.5% CHAPS) containing 0.1% protease inhibitor cocktail III (Calbiochem, San Diego, Calif., USA). The cell lysates were electrophorased, transferred to nitrocellulose membranes by blotting, and then the membranes were blocked with 4% BlockAce solution (Dainippon Pharmaceutical, Osaka, Japan) for 3 hours. The membranes were incubated for 12 hours in the presence of anti-BIG3 purified antibody (anti-hA7322 (His13), Sigma); anti-HA tag antibody (3F10, Roche, Mannheim, Germany); anti-PHB2 antibody, and anti-NcoR antibody (Abcam, Cambridge, UK); anti-PKAα cat antibody (C-20), anti-PKCα antibody (H-7), anti-PP1Cα antibody (FL-18), and anti-HDAC1 antibody (H-51) (Santa Cruz Biotechnology, Santa Cruz, Calif., USA); anti-HER2 antibody (Merck, Darmstadt, Germany); anti-HER3 antibody (1B2E) anti-TTK antibody (D-8), anti-MK5 antibody (D70A10), anti-CHK1 antibody (G-4), anti-phosphorylated Shc (Y239/Y240), anti-p38 antibody, anti-phosphorylated p38 antibody (T180/Y182), anti-NF-κB p65 antibody, anti-IκB antibody (L35A5), and anti-phosphorylated IκB antibody (S32/S36, 5A5) (Cell Signaling Technology, Danvers, Mass., USA); anti-Shc antibody (BD, Franklin Lakes, N.J., USA); anti-phosphorylated PHB2 purified antibody (Ser39), anti-phosphorylated BIG3 purified antibody (Ser305), and anti-phosphorylated BIG3 antibody (Ser1208, Scrum Inc., Tokyo, Japan); and anti-phosphorylated threonine antibody (Thermo Fisher Scientific). After incubation in the presence of HRP-conjugated secondary antibody (Santa Cruz Biotechnology) for 1 hour, the membranes were developed with an enhanced chemiluminescence system (GE Healthcare, Buckinghamshire, UK). The blots were scanned using the Image Reader LAS-3000 mini (Fujifilm, Tokyo, Japan).

Phos-tag SDS-PAGE

Phos-tag SDS-PAGE was carried out using precast Super-Sep gels (50 µM phos-tag acrylamide and 100 µM $ZnCl_2$, Wako Pure Chemical, Osaka, Japan) to evaluate the direct phosphorylation of PHB2 by a kinase. WIDE-VIEW Prestained Protein Size Marker (Wako Pure Chemical) was used as the molecular marker. Phosphorylation efficiencies were calculated from the ratio of the phosphorylated PHB2 band with respect to the total PHB2 band.

Immunoprecipitation

As mentioned in the "Western Blot Analyses" section, the cells were lysed in a 0.1% NP-40 lysis buffer, and the cell lysates were pre-cleared with Normal IgG and rec-Protein G Sepharose 4B (Thermo Fisher Scientific) at 4° C. for 3 hours. After centrifugation, the supernatants were incubated at 4° C. for 12 hours in the presence of 5 μg of anti-BIG3 antibody, anti-PHB2 antibody, anti-HER2 antibody, anti-PKCα antibody, and anti-HA tag antibody. Then upon adding rec-Protein G Sepharose 4B and incubating at 4° C. for 1 hour, the antigen-antibody complexes were precipitated. The immunoprecipitated protein complexes were washed three times with the lysis buffer, and separation was performed by SDS-PAGE. Thereafter, Western blot analyses were carried out.

In Vivo Tumor Growth Inhibition

KPL-4 cell suspensions and trastuzumab-resistant SK-BR-3 cell suspensions (1×10$^7$ cells/mouse) were mixed with an equal volume of Matrigel (BD) and injected into the mammary fat pads of 5-week-old female BALB/c nude mice (Charles River Laboratories, Tokyo, Japan). The mice were reared in a pathogen-free isolation facility with a 12-hour light/dark cycle and were fed rodent chow and water ad libitum. The tumors were grown over one week until they reached sizes of approximately 100 mm$^3$ [calculated as ½×(width×length)]. The mice were then randomized into each of the experiment groups (five heads/group). stERAP treatment involved administration of 150 μg/kg to mice by tail vein injection every seven days. The tumor volume was measured with calipers every four days for four weeks. All the experiments were performed in accordance with the guidelines of the animal facility at Tokushima University.

Kinase Reaction

The activities of protein kinase A (PKA) and protein kinase C alpha (PKCα) were measured by reacting the immunoprecipitates of BIG3 and PKCα with a synthetic substrate CREBtide (KRREILSRRPSYR) and 0.5 mM ATP in a kinase buffer (25 mM Hepes, pH 7.2, 25 mM MgCl$_2$, 5 mM EDTA, 5 mM EGTA, 0.25 mM DTT) at 30° C. for 30 minutes, and by using an ADP-Glo kinase assay Kit (Promega, Fitchburg, Wis., USA).

PP1Cα Activity

The phosphatase activity of PP1Cα was determined using the Protein Phosphatase Assay Kit (AnaSpec, Fremont, Calif., USA). After cell lysates were incubated with a substrate (p-Nitrophenyl phosphate) at room temperature for 60 minutes, the reaction was stopped and the absorbance at 405 nm was measured. PP1Cα activity (μmole/min) was defined as the amount of enzyme needed to catalyze 1 μmole of substrate per minute.

Cell Growth Assay

Cell growth assay was carried out using the Cell Counting Kit-8 (CCK-8, Dojindo, Kumamoto, Japan). Cells were harvested, plated into 48-well plates at 2×10$^4$ cells/well, and maintained in an incubator (37° C.) in the presence of 5% CO$_2$. At the point as instructed, a ten-fold diluted CCK-8 solution was added, this was incubated for 30 minutes, and the absorbance at 450 nm was measured to calculate the number of viable cells.

Real-Time PCR

The expression of BIG3 was evaluated by real-time PCR. Total RNA was extracted from each of the cells using NucleoSpin RNA (Macherey-Nagel, Germany), and this was reverse transcribed to cDNA using Superscript II reverse transcriptase (Thermo Fisher Scientific), oligo dT primer (Thermo Fisher Scientific), and 25 mM dNTP Mixture (Thermo Fisher Scientific). cDNA analyses were performed by real-time PCR on the 7500 Real Time PCR System (Thermo Fisher Scientific) using SYBR Premix Ex Taq (Thermo Fisher Scientific). Each sample was normalized to the mRNA content of β2-MG. The primers used for the amplification are as follows:

```
BIG3:
                                        (SEQ ID NO: 18)
    5'-CTTGACAAGGCCTTTGGAGT-3'
    and (SEQ ID NO: 19)
    5'-CAATATGCTTTTCCCGCTTT-3';
    and β2-MG:
                                        (SEQ ID NO: 20)
    5'-AACTTAGAGGTGGGGAGCAG-3'
    and (SEQ ID NO: 21)
    5'CACAACCATGCCTTACTTTATC-3'.
```

Isolation of Cytoplasm and Nucleus

The cytoplasmic fractions and nuclear fractions were isolated using NE-PER nuclear and cytoplasmic extraction reagent (Thermo Fisher Scientific).

Cell Cycle

Cells were fixed using cold 70% ethanol, stained using 20 μg/mL propidium iodide (Sigma) and 1 mg/mL ribonuclease A (Sigma), and analyzed by FACS Calibur (BD, Franklin Lakes, N.J., USA). Cell cycle profiles were evaluated using CellQuest software (BD, Franklin Lakes, N.J., USA).

Statistical Analysis

Student's t-tests were used to determine the statistical significance of the differences among the experimental groups. $P<0.05$ was considered significant.

Results

BIG3 in HER2-Positive Breast Cancer Cell Lines Function as AKAP

The present inventors have reported in WO 2013/018690 and in Nat. Commun. 2017 May 30; 8: 15427 that BIG3 functions as an A kinase anchor protein (AKAP) in estrogen receptor (ERα)-positive breast cancer cells. This time, the present inventors examined whether BIG3 functions as AKAP in human epidermal growth factor receptor 2 (HER2)-positive breast cancer cell lines as well. First, BIG3 expressions in HER2-positive breast cancer cell lines were evaluated by real-time PCR. As a result, each of the HER2-positive breast cancer cell lines (BT-474 cells, SK-BR-3 cells, and KPL-4 cells) showed remarkable enhancement of BIG3 expression (FIG. 15A), and expression higher than in ERα-positive breast cancer MCF-7 cells was shown.

Accordingly, the inventors considered the possibility that BIG3 may function as AKAP in HER2-positive breast cancer cells as in ERα-positive breast cancer cells. As a result, in HER2-positive breast cancer cell lines SK-BR-3 cells and KPL-4 cells, PKA, PP1Cα, and PHB2 were found to bind strongly to the immunoprecipitates of BIG3 (FIG. 15B), and the possibility was considered that BIG3 may function as AKAP in HER2-positive breast cancer cells as well, by forming complexes with PKA and protein phosphatase.

Next, to evaluate the mechanism of BIG3 activation in HER2-positive breast cancer cells, whether PKA and PP1Cα exist downstream of the HER2 signal and Epidermal Growth Factor Receptor (EGFR) signal was investigated by examining the effects of BIG3 on PKA activity and PP1Cα activity using the HER2 inhibitor trastuzumab and the EGFR inhibitor lapatinib. As a result, treatment of the immunoprecipitates of BIG3 with the PKA inhibitor H-89 and trastuzumab showed inhibition rates of 100% and 88%, respectively, for PKA activity and inhibition rates of 96% and 88%, respectively, for PP1Cα activity (FIG. 15C). On the other hand, since lapatinib treatment showed decrease in PKA activity and PP1Cα activity by only about 15% (FIG. 15C), BIG3 was suggested to be activated via HER2 signaling.

Mechanism of BIG3 Activation in HER2-Positive Breast Cancer Cell Lines

Since phosphorylation of Ser305 and Ser1208 is necessary for the activation of BIG3 (Nat. Commun., 8, 15427, 2017), phosphorylation of BIG3 HER2-positive breast cancer cells was examined. As a result, each of the phosphorylations (at Ser305 and at Ser1208) of BIG3 were found to be constitutively induced in SK-BR-3 cells and KPL-4 cells (FIG. 16), and BIG3 was considered to be constantly activated in HER2-positive breast cancer cells. On the other hand, when effects by PKA inhibitor H-89, HER2 inhibitor trastuzumab, and EGFR inhibitor lapatinib were examined, each of the phosphorylations (at Ser305 and at Ser1208) of BIG3 activated in SK-BR-3 cells and KPL-4 cells were nearly completely suppressed by treatment with H-89 and trastuzumab whereas lapatinib treatment was not so involved in the suppression of BIG3 phosphorylation (FIG. 16). This suggested that BIG3 may be activated via PKA derived from HER2 signaling.

BIG3 in HER2-Positive Breast Cancer Cell Lines Regulates the Inhibitory Activity of PHB2

Figure 17A:
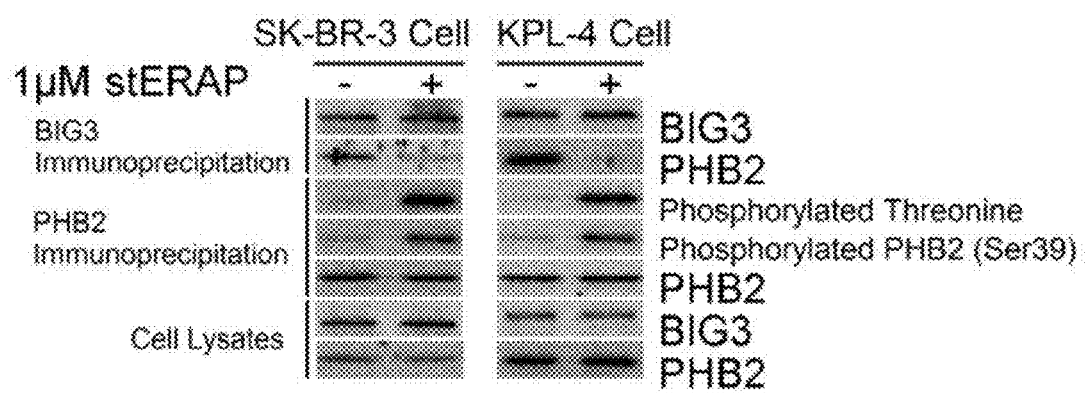

So far, the present inventors have elucidated that phosphorylation of BIG3 activated by PKA enhances the phosphatase activity of PP1Cα, and that by dephosphorylating the phosphorylated Ser39 of the cancer suppressor PHB2 (Prohibitin 2) which is bound to BIG3, which is the regulation unit of PP1Cα, the phosphorylation is greatly involved in the growth of breast cancer cells (Nat. Commun., 8, 15427, 2017). Furthermore, the present inventors designed ERAPs which are dominant negative peptides targeting the BIG3-PHB2 interaction (Nat. Commun., 4, 2443, 2013), undertook biological improvements so that they will exhibit long-term stability and have high sensitivity to inhibition of BIG3-PHB2 interactions, and produced stapled ERAPs (stERAPs) (Sci. Rep., 7, 1821, 2017). Actually, when stERAP was administered to breast cancer cell lines, binding between BIG3 and PHB2 was completely inhibited, and PHB2 dissociated from BIG3 was rapidly phosphorylated at its Ser39, and showed its suppressive activity (Sci. Rep., 7, 1821, 2017). Then, the effects of stERAP on BIG3 and PHB2 in HER2-positive breast cancer cells were investigated. As a result, when SK-BR-3 cells and KPL-4 cells were treated with stERAP, the interaction between BIG3 and PHB2 was observed to be nearly completely inhibited (FIG. 17A). Furthermore, phosphorylation of Ser39 and threonine in PHB2 which dissociated from BIG3 as a result of stERAP treatment was found to be induced rapidly (FIG. 17A), and BIG3 was suggested to regulate the phosphorylation (suppressive activation) of PHB2.

Figure 17B:
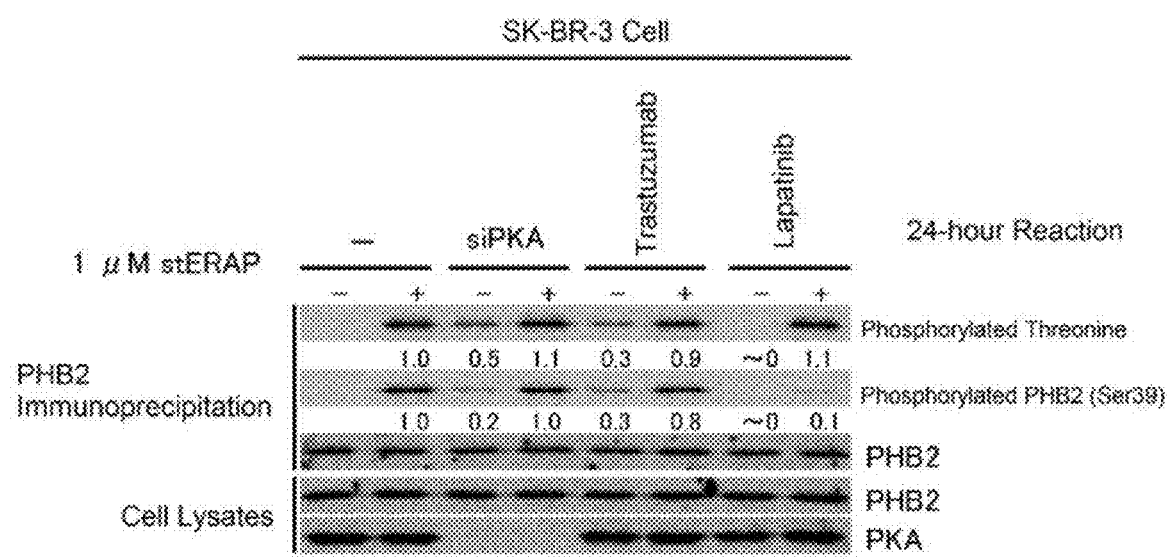

Next, the mechanism of PHB2 activation in HER2-positive breast cancer cells was evaluated. The experiments were performed by examining suppression of PKA expression by the siRNA method to suppress activation of BIG3, and phosphorylation of PHB2 using the HER2 inhibitor trastuzumab and the EGFR inhibitor lapatinib. As a result, decreasing trend in phosphorylation of PHB2 (Ser39) was hardly observed by the siPKA treatment and trastuzumab treatment; however, the phosphorylation was nearly completely suppressed by the lapatinib treatment (FIG. 17B). Therefore, phosphorylation of PHB2 (Ser39) was considered to be mainly due to EGFR signaling.

On the other hand, since threonine phosphorylation in PHB2 was independent of HER2 signaling and EGFR signaling (FIG. 17B), an activation mechanism completely different from that of Ser39 phosphorylation was considered to exist.

PKCα-Dependent Phosphorylation of PHB2 (Ser39)

Figure 18A:
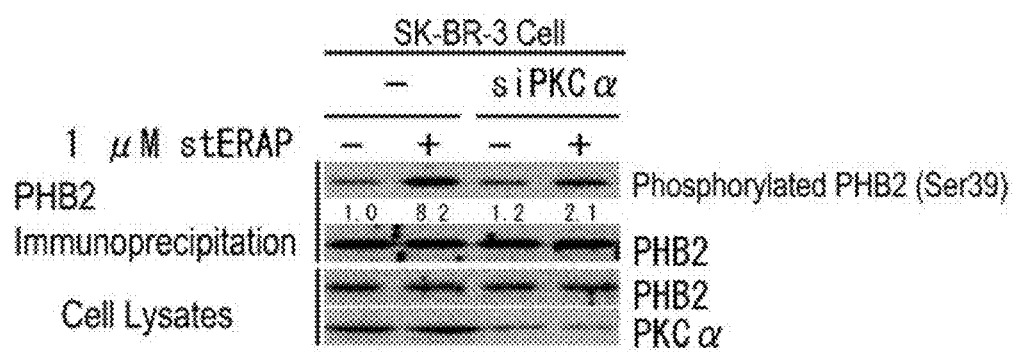
Figure 18B:
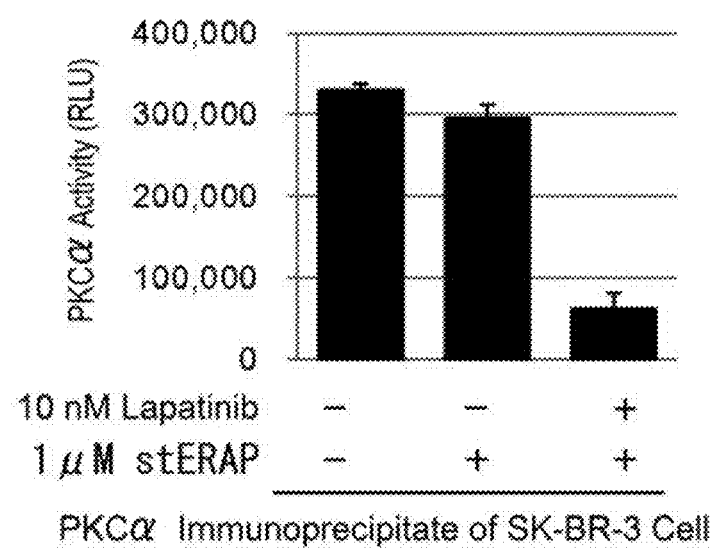

To date, since the present inventors have found that PKCα phosphorylates Ser39 of PHB2 in ERα-positive breast cancer (Nat. Commun., 8, 15427, 2017), the effects of suppressing PKCα expression by the siRNA method on the phosphorylation of PHB2 (Ser39) were examined. As a result, phosphorylation of PHB2 (Ser39) induced by stERAP treatment was remarkably suppressed by siPKCα treatment (FIG. 18A). Furthermore, since PKCα activity of the immunoprecipitates of PKC≠ SK-BR-3 cells showed activity inhibition of approximately 80% by lapatinib treatment (FIG. 18B), PHB2 (Ser39) was suggested to be phosphorylated via PKCα activation caused by EGFR signaling.

Phosphorylated PHB2 (Ser39) Suppressed Transcriptional Activity in the Nucleus

Involvement of PHB2 (Ser39) phosphorylation in suppression of transcriptional activity was evaluated using the phosphorylated mutant of PHB2. In the experiment, SK-BR-3 cells in which PHB2 expression has been suppressed by the siRNA method were transfected with HA-tagged PHB2 construct and the alanine mutant at Ser39 (S39A). 48 hours later, this was treated with stERAP for 24 hours. The nuclear fractions were isolated and immunoprecipitated with an HA antibody. As a result, the HA-tagged PHB2 that had translocated into the nucleus by stERAP treatment showed remarkable binding between transcriptional repressors NcoR and HDAC1 (FIG. 19A), suggesting that transcriptional activity may be suppressed. On the other hand, since binding of NcoR and HDAC1 to HA-tagged S39A was attenuated in S39A-transfected cells (FIG. 19A; reduction rate of 82% for NcoR and for HDAC1), serine phosphorylation of PHB2, particularly Ser39 phosphorylation, was suggested to be greatly involved in the suppression of transcriptional activity. Furthermore, when the effects of Ser39 phosphorylation on suppression of transcriptional activity was examined using the phosphomimetic S39E, the cells transfected with the mock-phosphorylated S39E bound strongly to NcoR and HDAC1 as in WT (FIG. 19A), and phosphorylation of Ser39 in PHB2 was considered to be important for suppression of transcriptional activity.

Figure 19B:
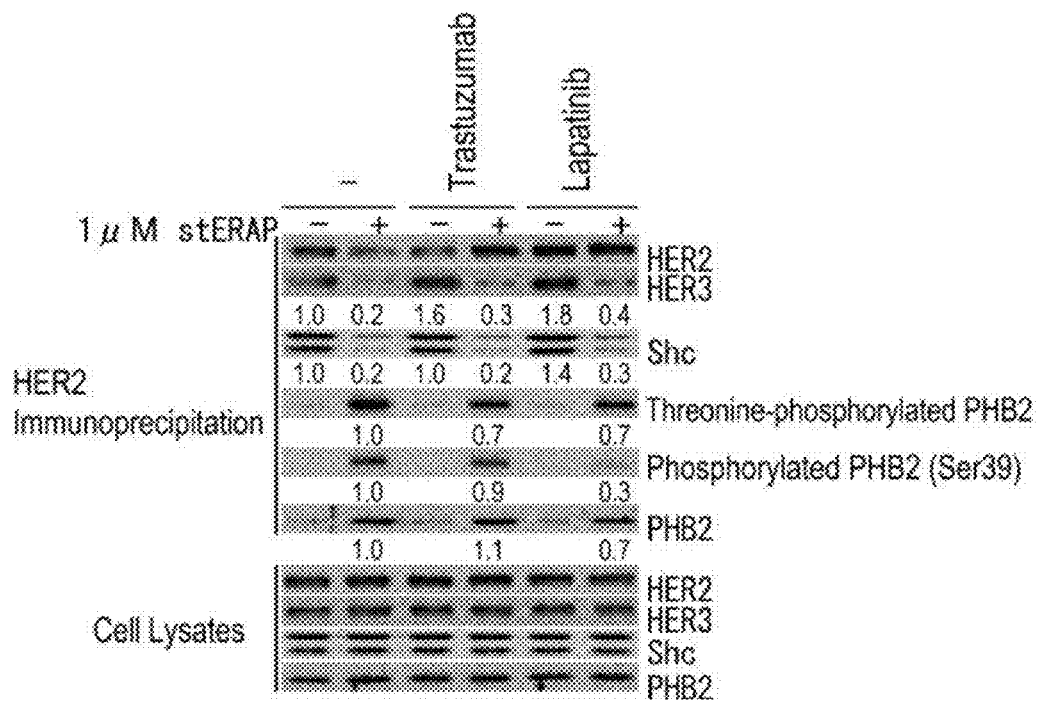

Next, the effects of phosphorylation of PHB2 (Ser39) on the HER2-HER3 and HER2-Shc interactions were examined. As a result, Ser39 of PHB2 which had dissociated from BIG3 by treatment with stERAP alone was found to be phosphorylated, and by binding to HER2, it was shown to inhibit the interactions between HER2 and HER3 and between HER2 and Shc by 83% in both cases (FIG. 19B). On the other hand, while lapatinib treatment in the presence of stERAP hardly showed PHB2 (Ser39) phosphorylation, as described above (FIG. 17B), HER2-HER3 and HER2-Shc interactions could be remarkably inhibited to 62% and 74%, respectively, and PHB2 (Ser39) phosphorylation was considered not to affect suppression of HER2 signaling. On the other hand, PHB2 was observed to also induce threonine phosphorylation by stERAP treatment (FIG. 19B). Since this phosphorylation was independent of HER2 signaling and EGFR signaling (FIG. 17B and FIG. 19B), this suggested the possibility that threonine phosphorylation of PHB2 is greatly involved in suppression of HER2 signaling.

Threonine Phosphorylation of PHB2 and its Activation Mechanism

The activation mechanism of threonine phosphorylation of PHB2 was examined. First, PHB2 threonine phosphorylation was evaluated when PKCα expression was suppressed by the siRNA method, assuming involvement of PKCα in a similar manner to Ser39 phosphorylation. PHB2 threonine phosphorylation induced by stERAP treatment was strongly maintained even in cells subjected to trastuzumab treatment and siPKCα treatment (FIG. 20A), suggesting that PHB2 threonine phosphorylation is activated by a kinase(s) other than PKCα.

PHB2 dissociated from BIG3 due to stERAP treatment was suggested to induce threonine phosphorylation in addition to phosphorylation of Ser39 (FIG. 17B and FIG. 19B); therefore, the PHB2 threonine phosphorylation sites were predicted using a public database. As a result, by NetPhos 3.1 (http://www.cbs.dtu.dk/services/NetPhos/), Thr155 and Thr169 showed high scores (0.849 and 0.992, respectively; Table 1A). While they were both present in the inhibitory domain of the ERα transcriptional activity of PHB2 (19-49 aa and 150-174 aa; Proc. Natl. Acad. Sci. USA, 96, 6947, 1999), there suggested the possibility that Thr169 may be phosphorylated by a kinase other than PKC.

TABLE 1

Threonine phosphorylation sites of PHB2 and kinases by public databases

A
Predicted sites of threonine phosphorylation in PHB2 (NetPhos 3.1)

| Target site | Score | Kinase |
|---|---|---|
| T169 | 0.992 | — |
| T155 | 0.849 | PKC |
| T194 | 0.738 | — |
| T94 | 0.617 | PKC |
| T42 | 0.526 | CKI |
| T62 | 0.476 | CaM-II |
| T185 | 0.476 | cdc2 |
| T21 | 0.457 | CaM-II |
| T288 | 0.455 | GSK3 |
| T274 | 0.452 | CaM-II |
| T263 | 0.444 | GSK3 |
| T266 | 0.425 | GSK3 |

B
Kinase predicted sites on threonine phosphorylation in PHB2 (GPS 3.0)

| Phosphorylated site | Kinase | Score |
|---|---|---|
| T42 | TTK | 62.64 |
| T194 | GRK | 14.28 |
| T185 | MAPK2K2 | 12.00 |
| T169 | CHK1 | 11.55 |
| T62 | TAOK1 | 11.00 |
| T169 | MK5 | 10.63 |
| T288 | GRK1 | 10.62 |
| T266 | PIM1 | 10.15 |
| T155 | MAP2K2 | 9.00 |
| T263 | MAP4K4 | 9.00 |
| T21 | VRK2 | 8.50 |
| T274 | AMPKA1 | 7.75 |
| T94 | AAK1 | 5.00 |

Next, when kinases involved in the phosphorylation of the threonine residue of PHB2 were predicted using the Group-based Prediction System (GPS3.0; http://gps.biocuckoo.org/), TKK showed a remarkably high score (62.64) compared to the other kinases with respect to Thr42 phosphorylation (Table 1B). From the above-mentioned prediction results, Thr42 and Thr169 of PHB2 were predicted to be the threonine phosphorylation sites, and the present inventors focused on TTK as the kinase for Thr42 and CHK1 and MK5 as the kinases for Thr169.

Figure 20B:
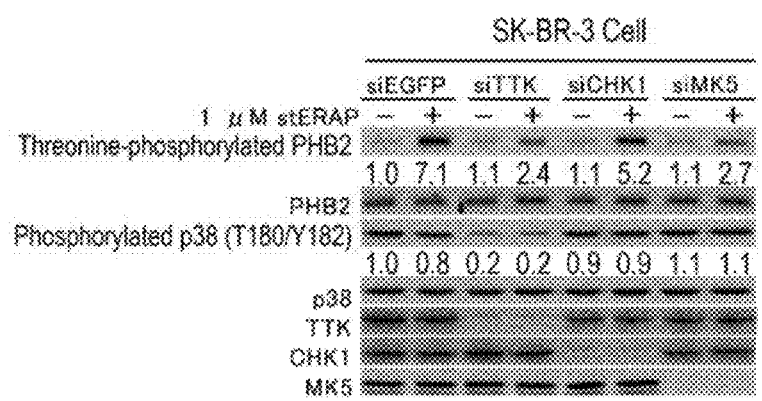

Then, PHB2 threonine phosphorylation was evaluated when stERAP treatment was performed by suppressing TTK, CHK1, and MK5 expressions by the siRNA method. As a result, when PHB2 threonine phosphorylation induced by stERAP treatment was subjected to siTTK treatment and siMK5 treatment, inhibitory effects of 79% and 74% were shown, respectively (FIG. 20B). Furthermore, while siCHK1 treatment showed an inhibition rate of 33% for threonine phosphorylation of PHB2, TTK and MK5 were determined to be greatly involved in the threonine phosphorylation of PHB2.

Since it has been reported that p38 is a substrate of TTK (JP 4647456 B2), the relationship between TTK and p38 was investigated. Interestingly, p38 phosphorylation was suppressed to approximately 25% by siTTK treatment (FIG. 20B), suggesting that p38 is present downstream of TTK. Furthermore, since p38 activates MK5 (Cell Signal, 22, 1185, 2010), this suggested the presence of a pathway in which MK5 is activated via p38 activated by TTK. From the above-mentioned results, it was considered that TTK regulates the phosphorylation of Thr42 and Thr169 in PHB2, and that MK5 is involved in the phosphorylation of Thr169.

Effects of Threonine Phosphorylation of PHB2 by TTK and MK5 on HER2 Signaling

To investigate the effects of TTK, MK5, and CHK1 on the HER2-HER3 and HER2-Shc interactions, the expression of each of them were suppressed by siRNA, and then immunoprecipitation was performed with a HER2 antibody. As a result, when SK-BR-3 cells were treated with 1 μM stERAP, binding of HER3 and Shc to HER2 were inhibited by 93% and 90%, respectively; whereas this binding inhibition was avoided when TTK expression and MK5 expression were suppressed (FIG. 21A; siTTK: inhibition rates of 23% and 9%, respectively; siMK5: inhibition rates of 48% and 31%, respectively). Furthermore, suppression of TTK expression and MK5 expression suppressed the threonine phosphorylation of PHB2 caused by stERAP treatment by 87% and 46%, respectively (FIG. 21A). Since similar results were also obtained from other HER2-positive breast cancer cell line KPL-4 cells (FIG. 21B), it was considered that threonine phosphorylation of PHB2 by TTK and MK5 is important for the regulation of the HER2 signaling cascade. On the other hand, since suppression of CHK1 expression in SK-BR-3 cells and KPL-4 cells could not avoid the inhibition of HER2-HER3 binding and HER2-Shc binding caused by stERAP treatment, CHK1 was considered to be hardly involved in HER2 signaling.

Next, by using the TTK inhibitor AZ3146, effects on threonine phosphorylation of PHB2 and HER2 signaling were examined. As a result, while treatment with stERAP alone could reproduce the remarkable inhibition of HER2-HER3 and HER2-Shc interactions (inhibition rates of 96% and 91%, respectively), AZ3146 nearly completely canceled the inhibitory effects (FIG. 20C). Furthermore, since AZ3146 inhibited the threonine phosphorylation of PHB2 to 23% (FIG. 20C), this suggested that threonine phosphorylation of PHB2 caused by TTK activation is involved in the inhibition of HER2 signaling.

Identification of the Threonine Phosphorylation Sites of PHB2

Whether the threonine phosphorylation sites of PHB2 are Thr42 and Thr169 was examined. In the experiment, SK-BR-3 cells in which the expression of endogenous PHB2 was suppressed by the siRNA method were transfected with the HA-tagged PHB2 construct (WT), alanine mutant at Thr42 (T42A), alanine mutant at Thr169 (T169A), and double alanine mutant at Thr42 and at Thr169 (T42A+T169A), and after treatment with stERAP for 24 hours, the cells were immunoprecipitated using an anti-HA antibody. As a result, threonine phosphorylation of PHB2 induced by stERAP treatment in WT-transfected cells was observed to be attenuated by 50% and 20% in the T42A and T169A mutants, respectively, and 76% of threonine phosphorylation was suppressed in the T42A+T169A double mutant (FIG. 22A).

Next, the effects of each of the phosphorylations at Thr42 and Thr169 of PHB2 on the suppression of HER2 signaling were examined. In the experiment, SK-BR-3 cells in which the expression of endogenous PHB2 was suppressed by the siRNA method were transfected with each HA-tagged PHB2 (wild type (WT), alanine mutant at Ser39 (S39A), and double alanine mutant at Thr42 and at Thr169 (T42A+T169A)), and after treatment with stERAP for 24 hours, the cells were immunoprecipitated using an anti-HER2 antibody and an anti-BIG3 antibody. As a result, while each HA-tagged PHB2 bound directly to HER2 even without stERAP treatment, stERAP treatment nearly completely inhibited the binding between BIG3 and each HA-tagged PHB2 (FIG. 22B, immunoprecipitants of BIG3), and since the amount of HA-tagged PHB2 bound to HER2 increased accordingly, it was judged that under stERAP treatment, conditions where HA-tagged PHB2 does not bind to BIG3 is established.

Therefore, under this condition, the effects of each HA-tagged PHB2 on the HER2-HER3 and HER2-Shc interactions were examined. PHB2-WT bound to HER2 nearly completely inhibited the HER2-HER3 and HER2-Shc interactions (FIG. 22B; inhibition rates of 98% for HER2-HER3 and 93% for HER2-Shc); whereas the binding with HER3 and Shc were inhibited by 95% and 85%, respectively, in the PHB2-S39A mutant (FIG. 22B), and the inhibitory effect was approximately the same as that in WT. On the other hand, in the T42A+T169A threonine double mutant, even though Ser39 of PHB2 was phosphorylated, the suppressive function of PHB2 was remarkably lost (inhibition rates of 15% for HER2-HER3 and 15% for HER2-Shc), suggesting that the suppressive function of PHB2 on HER2 signaling is greatly involved in the respective phosphorylation of Thr42 and Thr169.

Threonine Phosphorylation of PHB2 Caused by TTK and MK5

Whether TTK and PHB2 bind was examined by immunoprecipitating SK-BR-3 cells treated for 24 hours with stERAP using an anti-TTK antibody and an anti-PHB2 antibody. As a result, immunoprecipitations with both antibodies showed that TTK and PHB2 strongly interact (FIG. 23A), suggesting that TTK directly phosphorylates PHB2.

Figure 23B:
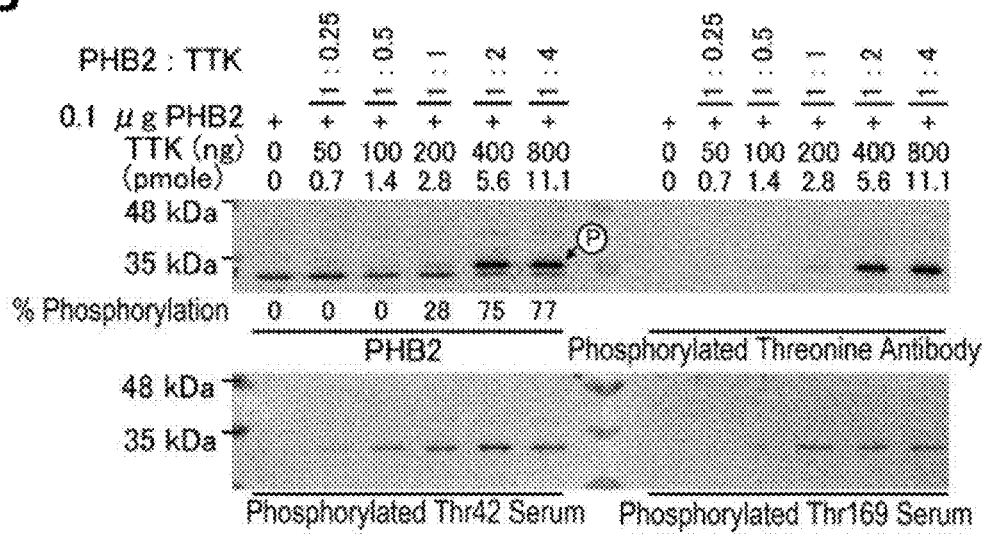

Next, the possibility that TTK and MK5 directly threonine-phosphorylate PHB2 was evaluated by SDS-PAGE which uses Phos-tag. In the experiment, recombinant PHB2 and recombinant TTK or recombinant MK5 were reacted in the presence of ATP at 30° C. for 30 minutes, and then subjected to Phos-tag SDS-PAGE. As a result, while a phosphorylation band was slightly observed (28% phosphorylation) when the molar ratio between recombinant TTK and PHB2 was 1:1, when the molar ratio was PHB2:TTK=1:2 or greater, a band for 75% phosphorylation was clearly detected (FIG. 23B). When immunoblotting was performed using an anti-phosphorylated threonine antibody, phosphorylation bands were found at nearly the same positions (FIG. 23B). Furthermore, when immune serum against phosphorylated Thr42 and phosphorylated Thr169 were immunoblotted, phosphorylated Thr42 was detected with high sensitivity, but depending on the molar ratios of PHB2 and TTK, each phosphorylation band was observed clearly (FIG. 23B), suggesting the possibility that TTK can directly phosphorylate Thr42 and Thr169 of PHB2.

Figure 23C:
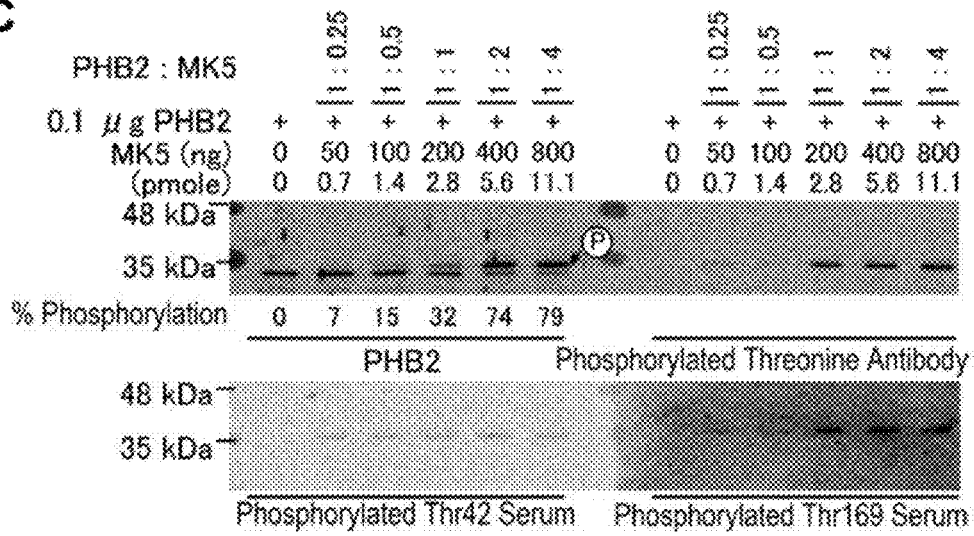

Regarding recombinant MK5, a phosphorylation band was slightly observed (6.5% phosphorylation) starting from molar ratio of PHB2:MK5=1:0.25, the phosphorylation efficiency increased depending on the molar ratio, and at a molar ratio of PHB2:MK=1:2 or more, a band for 75% phosphorylation was detected, and this band was at the same position as in the immunoblot of anti-phosphorylated threonine antibody (FIG. 23C). Furthermore, when immune serum was immunoblotted similarly to the method described above, serum of phosphorylated Thr42 slightly reacted, and phosphorylated Thr169 serum showed nearly the same phosphorylation manner as the anti-phosphorylated threonine antibody, and this strongly suggested that in PHB2, Thr169 is the site of phosphorylation by MK5.

Inhibitory Effects of stERAP on the Growth of HER2-Positive Breast Cancer Cell Lines The growth suppressive effects of stERAP on HER2-positive breast cancer cell lines were examined (FIG. 24). As a result, stERAP showed dose-dependent inhibitory effects on the growth of each of the HER2-positive breast cancer cell lines (SK-BR-3 cells, BT-474 cells, and KPL-4 cells), and the $IC_{50}$ (50% inhibition concentration) for the cell lines were 0.054 µM, 0.58 µM, and 0.02 µM, respectively. Furthermore, since SK-BR-3 cells and KPL-4 cells are estrogen receptor (ERα)-negative, stERAP was found to show remarkable growth suppressive effects in HER2-positive breast cancer cells and in ERα-negative cells as long as cells express BIG3.

stERAP Inhibits the HER2-HER3 and HER2-Shc Interactions

Using the $IC_{50}$ and complete inhibition concentration of stERAP for the growth of each of the HER2-positive breast cancer cell lines (SK-BR-3 cell: 0.05 µM and 1 µM; BT-474 cell: 0.5 µM and 10 µM; and KPL-4 cell: 0.01 µM and 1 µM, respectively), effects on the HER2-HER3 and HER2-Shc interactions in each cell line and effects of combined use with trastuzumab were examined. As a result, trastuzumab could hardly inhibit the binding of HER2 to HER3 and Shc whereas treatment with stERAP alone achieved strong inhibitory effects (FIG. 25), and at the complete inhibition concentration against cell growth, HER2-HER3 and HER2-Shc interactions could be inhibited nearly completely. Furthermore, when trastuzumab was used in combination with stERAP at its $IC_{50}$, dramatic enhancements in inhibition rates were observed (FIG. 25).

Furthermore, stERAP treatment showed similar inhibitory effects on the phosphorylation of HER2 (Y877) and the phosphorylation of Shc (Y239/Y240) (FIG. 25). In addition, although stERAP treatment induced the binding level of PHB2 to HER2 in a concentration-dependent manner, combined use with trastuzumab did not change the binding level of PHB2 (FIG. 25).

Inhibitory Effects of stERAP on Trastuzumab-Resistant HER2-Positive Breast Cancer Cell Lines Growth inhibitory effects of stERAP on trastuzumab-resistant SK-BR-3 cell were examined. As a result, administration of trastuzumab alone could not suppress the growth of trastuzumab-resistant SK-BR-3 cells at all whereas stERAP treatment showed dose-dependent suppressive effects on the growth of trastuzumab-resistant SK-BR-3 cells. Compared to the $IC_{50}$ (0.054 µM, FIG. 24) for trastuzumab-sensitive SK-BR-3 cells, the $IC_{50}$ was 10.64 µM which was higher (FIG. 26A), but regardless of whether the cells are resistant or sensitive, stERAP was found to have significant suppressive effects.

Figure 26B:
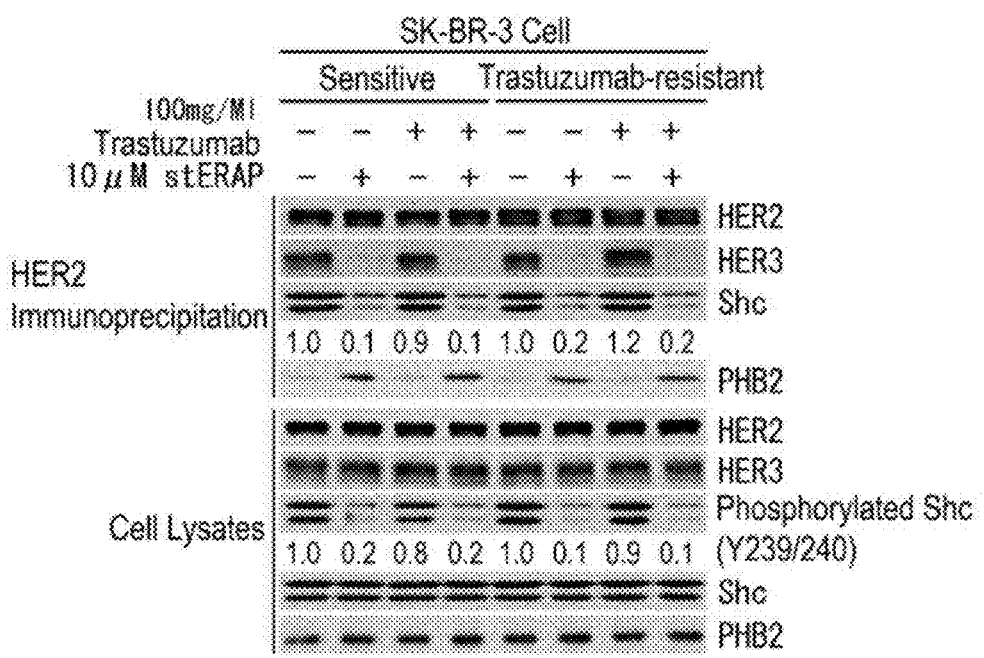

Next, effects of stERAP on the binding of the HER2-HER3 heterodimer and HER2-Shc in trastuzumab-resistant SK-BR-3 cells were examined. As a result, stERAP could nearly completely inhibit the binding of HER2-HER3 and HER2-Shc and the phosphorylation of Shc (Y239/Y240) in the sensitive and resistant cell lines (FIG. 26B). Furthermore, PHB2 which dissociated from BIG3 by stERAP treatment was observed to bind to HER2, and PHB2 was suggested to be involved in the inhibition of HER2-HER3 and HER2-Shc complexes. On the other hand, treatment with Herceptin alone hardly affected the binding of HER2-HER3 and HER2-Shc.

Effects of stERAP on NF-κB Signaling in Trastuzumab-Resistant HER2-Positive Breast Cancer Cell Lines It has been reported the possibility that activation of NF-κB signaling in HER2-positive breast cancer cells causes resistance to chemoradiotherapy (Anticancer Res., 26, 4235, 2006; Breast Cancer Res., 13, 221, 2011). Therefore, the effects of stERAP on NF-κB signaling in HER2-positive breast cancer cell lines were examined. As a result, compared to the parent SK-BR-3 cell line cells, a lot of NF-κB p65 was found to translocate into the nucleus in trastuzumab-resistant SK-BR-3 cells, and this signal was suggested to be involved in the resistance against trastuzumab treatment (FIG. 27). On the other hand, administration of stERAP remarkably inhibited the nuclear translocation of NF-κB p65 in trastuzumab-resistant SK-BR-3 cells (FIG. 27). Furthermore, stERAP was found to regulate the nuclear translocation of NF-κB p65 by nearly completely inhibiting the phosphorylation of IκBα which is activated only in trastuzumab-resistant SK-BR-3 cells (FIG. 27). The above result suggests that stERAP can avoid resistance to trastuzumab treatment by suppressing phosphorylation of IκBα and nuclear translocation of NF-κB p65.

Effects of stERAP on the Cell Cycle of a Trastuzumab-Resistant HER2-Positive Breast Cancer Cell Line (FIG. 28)

Effects of stERAP administration on the cell cycle of trastuzumab-resistant SK-BR-3 cells were examined. As a result, the cell cycle of trastuzumab-resistant SK-BR-3 cells had remarkably progressed to the G2/M phase, and although administration of trastuzumab could hardly arrest the cell cycle, administration of stERAP alone was found to arrest the cell cycle at the G0/G1 phase. Furthermore, when 20 µM stERAP and 100 µg/mL trastuzumab were used in combination, cells at the sub-G1 phase remarkably increased, and cell death was observed. The above result revealed that stERAP induces cytostatic effects by inducing G1 phase arrest and promotes cell death when used in combination with trastuzumab which has a different action mechanism.

In Vivo Antitumor Effects of stERAP on Trastuzumab-Resistant HER2-Positive Breast Cancer Cells (FIG. 29)

In vivo antitumor effects by stERAP were examined. KPL-4 and trastuzumab-resistant SK-BR-3 cells were orthotopically transplanted into the mammary glands of BALB/c nude mouse. When the tumor reached approximately 100 mm$^3$, stERAP administration through the tail vein was initiated, and then stERAP was administered every seven days thereafter, and the antitumor effects were investigated. As a result, while the KPL-4 tumor and the trastuzumab-resistant SK-BR-3 tumor grew over time, immediately after administration of stERAP at 150 µg/kg, the tumor size showed a decreasing trend, significant inhibitory effects were sustained even when administered every seven days, and tumor reduction was observed 28 days later. No toxicity and no significant body weight decrease due to stERAP administration were observed. Therefore, from a therapeutic viewpoint, excellent therapeutic index is suggested.

Example 5

Effects of Double stERAPs

Materials and Methods
Cell Lines and Culture Conditions

Three types of human breast cancer cell lines SK-BR-3, BT-20, and MDA-MB-231, and a human synovial sarcoma cell line SW982 were purchased from American Type Culture Collection (ATCC, Manassas, Va., USA).

SK-BR-3 cells were cultured using McCoy's 5A medium (Thermo Fisher Scientific, Waltham, Mass., USA), BT-20 cells were cultured using EMEM medium (Thermo Fisher Scientific) under 5% $CO_2$ at 37° C. MDA-MB-231 cells and SW982 cells were cultured using Leibovitz's L-15 medium (Thermo Fisher Scientific) at 37° C. without $CO_2$ concentration control. All media were used by supplementing 10% FBS (Thermo Fisher Scientific) and a 1% antibiotic/antimycotic solution (Wako Pure Chemical, Osaka, Japan).

Cell Growth Assay

SK-BR-3 cells, BT-20 cells, and MDA-MB-231 cells were seeded into 48-well plates at 1×10$^4$ cells/200 µL in each well, and SW982 cells were seeded into 48-well plates at 0.5×10$^4$ cells/200 µL in each well. 48 hours later, the medium in each well was exchanged to a medium supplemented with a peptide (single stERAP and double stERAP #46: three-fold serial dilution from 20 µM, double stERAP #45: two-fold serial dilution starting from 50 µM), and after culturing for another 96 hours, the level of cell growth was measured using the Cell Counting Kit-8 (Dojindo, Kumamoto, Japan). Data were obtained from three independent experiments, a graph (mean±standard deviation) was produced using a graphing and data analyzing software SigmaPlot (Systat Software, San Jose, Calif., USA), and the 50% inhibition concentration ($IC_{50}$) of the peptide against cell growth was calculated.

Cell Cycle Analysis

SK-BR-3 cells and MDA-MB-231 cells were seeded respectively at 5×10$^5$ cells/10 cm dish. 72 hours later, the medium was exchanged to a fresh medium supplemented with 5 µM peptide; cells were collected by trypsin treatment 48 hours, 72 hours, and 96 hours later; and the cells were fixed at −20° C. overnight or longer by adding 70% ethanol solution. The solution for the cell suspension was exchanged from 70% ethanol to Propidium Iodide (PI)/RNase Staining Solution (Cell Signaling Technologies, Danvers, Mass., USA), and after allowing the reaction to take place at room temperature in the dark for 15 minutes, the cell aggregates were removed using a cell strainer (BD biosciences, Franklin Lakes, N.J., USA). Next, the ratio of cell cycle phases for each cell sample was analyzed using FACS array (BD biosciences) and the analysis software FlowJo (FLOWJO LCC, Ashland, Oreg., USA).

Results
Growth Inhibitory Effects of stERAPs on Breast Cancer Cell Lines and a Synovial Sarcoma Cell Line The effects of three types of stERAPs on cell growth of three types of breast cancer cell lines (SK-BR-3, BT-20, and MDA-MB-231) and synovial sarcoma cell line SW982 were investigated. As a result, as shown in FIG. 30, concentration-dependent inhibitory effects on cell growth by each stERAP were observed in all cell lines. Furthermore, the 50% inhibition concentration (IC$_{50}$) for each peptide is shown in Table 2. Among the three types of peptides, double stERAP #46 had the highest growth inhibitory effects and strong growth inhibitory effects were observed in the highly malignant triple negative breast cancer-derived cell lines (BT-20 and MDA-MB-231) and synovial sarcoma-derived cell line SW982.

Effects of stERAPs on the Cell Cycle of Breast Cancer Cell Lines (SK-BR-3 and MDA-MB-231)

The effects of two types of peptides (single stERAP and double stERAP #46) having remarkable cytostatic effects on the cell cycles of two types of breast cancer cell lines (SK-BR-3 and MDA-MB-231) were examined by flow cytometry analyses. As a result, as shown in FIG. 31A, in SK-BR-3 cells, for both peptides, addition of peptide led to decrease in the number of cells at the G2/M phase and increase in the number of cells at the G1 phase, in comparison to a negative control in which phosphate-buffered saline (PBS) was added to cells. Accordingly, a G1-phase cell cycle arrest was observed. This effect was maintained even at 96 hours after peptide addition. On the other hand, in MDA-MB-231 cells, as shown in FIG. 31B, decrease in the number of G1-phase cells and increase in the number of S-phase cells were observed, S phase cell cycle arrest was observed, and these effects were maintained even 96 hours after peptide addition. These results suggest the possibility that the cytostatic effects of the two types of peptides (single stERAP and double stERAP #46) induce about cell cycle arrest.

TABLE 2

| 50% Cell growth inhibition concentration of stERAP peptides IC$_{50}$, μM) | | | | |
|---|---|---|---|---|
| Peptide | MDA-MB-231 | BT-20 | SK-BR-3 | SW 982 |
| Single stERAP | 0.597 | 0.36 | 0.09 | 0.274 |
| Double stERAP #45 | 23.7 | 8.6 | 2.8 | Not performed |
| Double stERAP #46 | 0.143 | 0.074 | 0.02 | 0.026 |

INDUSTRIAL APPLICABILITY

The present invention provides peptides having longer lasting inhibitory effects on the BIG3-PHB2 interaction. Pharmaceutical compositions comprising a peptide of the present invention or a salt thereof can be used to treat cancer, and particularly estrogen receptor-positive cancers and estrogen receptor-negative breast cancers and prostate cancers.

The invention claimed is:

1. A peptide comprising an amino acid sequence in which at least two pairs of amino acid residues are substituted with the same number of stapling structures in the amino acid sequence of SEQ ID NO: 4 or SEQ ID NO: 5, or a salt thereof,
wherein the two pairs of amino acid residues are either (a) and (b), or (c) and (d) below:
(a) the third and seventh amino acid residues from the N terminus of the amino acid sequence of SEQ ID NO: 4; and
(b) the eighth and twelfth amino acid residues from the N terminus of the amino acid sequence of SEQ ID NO: 4, or
(c) the third and seventh amino acid residues from the N terminus of the amino acid sequence of SEQ ID NO: 5; and
(d) the tenth and fourteenth amino acid residues from the N terminus of the amino acid sequence of SEQ ID NO: 5.

2. The peptide or the salt thereof of claim 1, wherein two pairs of amino acid residues are substituted with two stapling structures.

3. The peptide or the salt thereof of claim 1, wherein the stapling structure is represented by Formula (I) below:

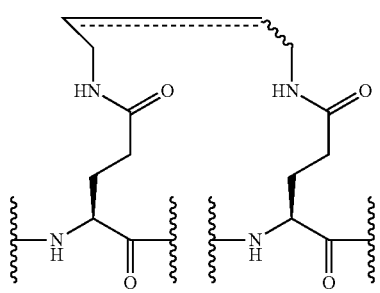

(I)

(wherein, the double line drawn by a solid line and a dashed line indicates a single bond or a double bond).

4. The peptide or the salt thereof of claim 3, wherein the stapling structure is represented by Formula (II) below:

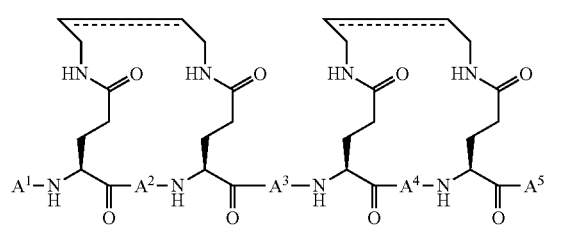

(II)

(wherein, the double line drawn by a solid line and a dashed line indicates a single bond or a double bond; the combination of $A^1$, $A^2$, $A^3$, $A^4$, and $A^5$ is selected from the following:
$A^1$=QM, $A^2$=SDL, $A^3$=-, $A^4$=QLR, and $A^5$=R; and
$A^1$=QM, $A^2$=SDL, $A^3$=LQ, $A^4$=RQR, and $A^5$=OH;
wherein "-" indicates a peptide bond with no additional amino acid residue (that is, two stapling structures are connected); and "OH" indicates that one end of the above stapling structure constitutes the C terminus of the peptide derivative).

5. The peptide or the salt thereof of claim 1, wherein either one or both of N-terminal and C-terminal amino acid residues have been modified.

6. The peptide or the salt thereof of claim 5, wherein either one or both of N-terminal and C-terminal amino acid residues have been modified by any one or a combination of acetylation, amidation, and HA tagging.

7. The peptide or the salt thereof of claim 6, wherein the N-terminal amino acid residue is acetylated and the C-terminal amino acid residue is amidated.

8. The peptide or the salt thereof of claim 1, wherein all the amino acid residues have been substituted with D-form amino acid residues.

9. A peptide which is a retro-inverso form of a peptide comprising an amino acid sequence in which at least two pairs of amino acid residues are substituted with the same number of stapling structures in the amino acid sequence of SEQ ID NO: 4 or SEQ ID NO: 5, or a salt thereof,
wherein the two pairs of amino acid residues are (a) and (b) below:

(a) the third and seventh amino acid residues from the N terminus of the amino acid sequence of SEQ ID NO: 4; and
(b) the eighth and twelfth amino acid residues from the N terminus of the amino acid sequence of SEQ ID NO: 4, or wherein the two pairs of amino acid residues are (c) and (d) below:
(c) the third and seventh amino acid residues from the N terminus of the amino acid sequence of SEQ ID NO: 5; and
(d) the tenth and fourteenth amino acid residues from the N terminus of the amino acid sequence of SEQ ID NO: 5.

10. A pharmaceutical composition comprising the peptide or the salt thereof of claim 1 and a pharmaceutically acceptable carrier.

11. The pharmaceutical composition of claim 10, which is for cancer therapy.

12. The pharmaceutical composition of claim 11, wherein the cancer is breast cancer or prostate cancer.

13. The pharmaceutical composition of claim 11, wherein the cancer is estrogen receptor-positive cancer.

* * * * *